(12) United States Patent
Ali et al.

(10) Patent No.: US 7,781,426 B2
(45) Date of Patent: Aug. 24, 2010

(54) CETP INHIBITORS

(75) Inventors: Amjad Ali, Freehold, NJ (US); Zhijian Lu, Clinton, NJ (US); Peter J. Sinclair, Scotch Plains, NJ (US); Gayle E. Taylor, Jersey City, NJ (US); Christopher F. Thompson, Clark, NJ (US); Cameron J. Smith, Lawrenceville, NJ (US); Adrian A. Dowst, Hoboken, NJ (US); Yi-Heng Chen, Whippany, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 7 days.

(21) Appl. No.: 12/087,184

(22) PCT Filed: Dec. 29, 2006

(86) PCT No.: PCT/US2006/049505

§ 371 (c)(1),
(2), (4) Date: Jun. 26, 2008

(87) PCT Pub. No.: WO2007/081571

PCT Pub. Date: Jul. 19, 2007

(65) Prior Publication Data

US 2009/0075979 A1    Mar. 19, 2009

Related U.S. Application Data

(60) Provisional application No. 60/755,251, filed on Dec. 30, 2005.

(51) Int. Cl.
| | |
|---|---|
| A61K 31/422 | (2006.01) |
| A61K 31/5377 | (2006.01) |
| A61K 31/541 | (2006.01) |
| A61K 31/496 | (2006.01) |
| A61K 31/443 | (2006.01) |
| A61K 31/4525 | (2006.01) |
| A61K 31/55 | (2006.01) |
| C07D 403/02 | (2006.01) |
| C07D 413/02 | (2006.01) |
| C07D 417/02 | (2006.01) |
| C07D 401/02 | (2006.01) |

(52) U.S. Cl. .................. 514/217.1; 514/376; 514/236.8; 514/227.8; 514/254.02; 514/340; 514/326; 548/230; 544/137; 544/60; 544/369; 546/271.4; 546/209; 540/603

(58) Field of Classification Search ............. 514/217.1, 514/227.8, 236.8, 254.02, 326, 340, 376; 540/603; 544/60, 137; 546/209, 271.4; 548/230
See application file for complete search history.

(56) References Cited

U.S. PATENT DOCUMENTS

| | | |
|---|---|---|
| 5,559,246 A | 9/1996 | Macor |
| 5,747,501 A | 5/1998 | Macor |
| 2006/0040999 A1 | 2/2006 | Ali et al. |

FOREIGN PATENT DOCUMENTS

| | | |
|---|---|---|
| WO | WO 2006/090792 | 8/2006 |
| WO | WO 2007/067593 | 6/2007 |

*Primary Examiner*—Kamal A Saeed
*Assistant Examiner*—Samantha L Shterengarts
(74) *Attorney, Agent, or Firm*—Mark R. Daniel; James L. McGinnis

(57) ABSTRACT

Compounds having the structure of Formula (I), including pharmaceutically acceptable salts of the compounds, are CETP inhibitors, and are useful for raising HDL-cholesterol, reducing LDL-cholesterol, and for treating or preventing atherosclerosis. In the compounds of Formula (I), B or $R^2$ is a phenyl group which has an ortho amine or aminomethyl substituent which is further substituted, and the other of B or $R^2$ is also a cyclic group.

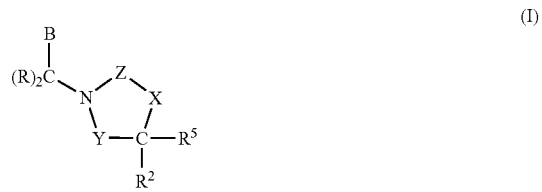

(I)

12 Claims, No Drawings

CETP INHIBITORS

CROSS REFERENCE TO RELATED APPLICATIONS

This application is a U.S. National Phase application under 35 U.S.C. §371 of PCT Application No. PCT/US2006/049505, filed Dec. 29, 2006, which claims priority under 35 U.S.C. §119(e) from U.S. Application No. 60/755,251, filed Dec. 30, 2005.

FIELD OF THE INVENTION

This invention relates to a class of chemical compounds that inhibit cholesterol ester transfer protein (CETP) and therefore have utility in raising HDL-C, lowering LDL-C, and in the treatment and prevention of atherosclerosis.

BACKGROUND OF THE INVENTION

Atherosclerosis and its clinical consequences, coronary heart disease (CHD), stroke and peripheral vascular disease, represent a truly enormous burden to the health care systems of the industrialized world. In the United States alone, approximately 13 million patients have been diagnosed with CHD, and greater than one half million deaths are attributed to CHD each year. Further, this toll is expected to grow over the next quarter century as an epidemic in obesity and diabetes continues to grow.

It has long been recognized that in mammals, variations in circulating lipoprotein profiles correlate with the risk of atherosclerosis and CHD. The clinical success of HMG-CoA Reductase inhibitors, especially the statins, in reducing coronary events is based on the reduction of circulating Low Density Lipoprotein cholesterol (LDL-C), levels of which correlate directly with increased risk for atherosclerosis. More recently, epidemiologic studies have demonstrated an inverse relationship between High Density Lipoprotein cholesterol (HDL-C) levels and atherosclerosis, leading to the conclusion that low serum HDL-C levels are associated with an increased risk for CHD.

Metabolic control of lipoprotein levels is a complex and dynamic process involving many factors. One important metabolic control in man is the cholesteryl ester transfer protein (CETP), a plasma glycoprotein that catalyzes the movement of cholesteryl esters from HDL to the apoB containing lipoproteins, especially VLDL (see Hesler, C. B., et. al. (1987) *Purification and characterization of human plasma cholesteryl ester transfer protein. J. Biol. Chem.* 262(5), 2275-2282)). Under physiological conditions, the net reaction is a heteroexchange in which CETP carries triglyceride to HDL from the apoB lipoproteins and transports cholesterol ester from HDL to the apoBliprotein.

In humans, CETP plays a role in reverse cholesterol transport, the process whereby cholesterol is returned to the liver from peripheral tissues. Intriguingly, many animals do not possess CETP, including animals that have high HDL levels and are known to be resistant to coronary heart disease, such as rodents (see Guyard-Dangremont, V., et. al., (1998) *Phospholipid and cholesteryl ester transfer activities in plasma from 14 vertebrate species. Relation to atherogenesis susceptibility, Comp. Biochem. Physiol. B Biochem. Mol. Biol.* 120 (3), 517-525). Numerous epidemiologic studies correlating the effects of natural variation in CETP activity with respect to coronary heart disease risk have been performed, including studies on a small number of known human null mutations (see Hirano, K.-I., Yamashita, S, and Matsuzawa, Y. (2000) *Pros and cons of inhibiting cholesteryl ester transfer protein, Curr. Opin. Lipidol.* 11(6), 589-596). These studies have clearly demonstrated an inverse correlation between plasma HDL-C concentration and CETP activity (see Inazu, A., et. al. (2000) *Cholesteryl ester transfer protein and atherosclerosis, Curr. Opin. Lipidol.* 11(4), 389-396), leading to the hypothesis that pharmacologic inhibition of CETP lipid transfer activity may be beneficial to humans by increasing levels of HDL-C while lowering those of LDL.

Despite the significant therapeutic advance that statins such as simvastatin (ZOCOR®) represent, statins only achieve a risk reduction of approximately one-third in the treatment and prevention of atherosclerosis and ensuing atherosclerotic disease events. Currently, few pharmacologic therapies are available that favorably raise circulating levels of HDL-C. Certain statins and some fibrates offer modest HDL-C gains. Niacin, which provides the most effective therapy for raising HDL-C that has been clinically documented, suffers from patient compliance issues, due in part to side effects such as flushing. An agent that safely and effectively raises HDL cholesterol levels can answer a significant, but as yet unmet medical need by offering a means of pharmacologic therapy that can significantly improve circulating lipid profiles through a mechanism that is complementary to existing therapies.

New classes of chemical compounds that inhibit CETP are being investigated at several pharmaceutical companies or are in clinical trials. No CETP inhibitors are currently being marketed. Clinical trials of torcetrapib were terminated because of an increase in mortality in patients who were taking torcetrapib in an outcomes study. New compounds are needed so that one or more pharmaceutical compounds can be found that are safe and effective. The novel compounds described herein are very potent CETP inhibitors.

SUMMARY OF THE INVENTION

Compounds having Formula I, including pharmaceutically acceptable salts of the compounds, are CETP inhibitors, having the utilities described below:

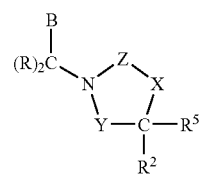

I

In the compounds of Formula I:

Y is selected from the group consisting of —C(=O)— and —(CRR$^1$)—;

X is selected from the group consisting of —O—, —NH—, and —N(C$_1$-C$_5$alkyl)-;

Z is selected from the group consisting of —C(=O)—, —S(O)$_2$—, and —C(=N—R$^9$)—, wherein R$^9$ is selected from the group consisting of H, —CN, and C$_1$-C$_5$alkyl optionally substituted with 1-11 halogens;

R and R$^1$ are each independently selected from the group consisting of H, —C$_1$-C$_5$ alkyl, and halogen, wherein —C$_1$-C$_5$ alkyl is optionally substituted with 1-11 halogens;

R$^5$ is selected from the group consisting of H, —OH, —C$_1$-C$_5$ alkyl, and halogen, wherein —C$_1$-C$_5$ alkyl is optionally substituted with 1-11 halogens;

B and $R^2$ are each selected from the group consisting of $A^1$ and $A^2$, wherein $A^1$ has the structure:

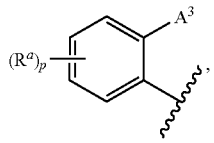

wherein one of the =CH— groups of the phenyl ring of $A^1$ that are optionally unsubstituted may optionally be replaced by =N—, so that $A^1$ comprises a a pyridine ring;

Wherein one of B and $R^2$ is $A^1$, and the other of B and $R^2$ is $A^2$, so that the compound of Formula I comprises one group $A^1$ and one group $A^2$;

$A^3$ is —$(CR^{10}R^{11})_q NR^7 R^8$;

$A^2$ is selected from the group consisting of:
(a) an aromatic ring selected from phenyl and naphthyl;
(b) a phenyl ring fused to a 5-7 membered non-aromatic cycloalkyl ring, which optionally comprises 1-2 double bonds;
(c) a 5-6-membered heterocyclic ring having 1-4 heteroatoms independently selected from N, S, O, and —N(O)—, and optionally also comprising 1-3 double bonds and a carbonyl group;
(d) a benzoheterocyclic ring comprising a phenyl ring fused to a 5-6-membered heterocyclic ring having 1-2 heteroatoms independently selected from O, N, and S and optionally 1-2 double bonds; and
(e) a —$C_3$-$C_8$ cycloalkyl ring optionally having 1-3 double bonds;

wherein $A^2$ is optionally substituted with 1-5 substituent groups independently selected from $R^a$;

Each $R^a$ is independently selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —$OC_1$-$C_6$alkyl, —$OC_2$-$C_6$ alkenyl, —$OC_2$-$C_6$ alkynyl, —$OC_3$-$C_8$ cycloalkyl optionally having 1-3 double bonds, —$C(=O)C_1$-$C_6$alkyl, —$C(=O)C_3$-$C_8$ cycloalkyl, —$C(=O)H$, —$CO_2H$, —$CO_2C_1$-$C_6$alkyl, —$C(=O)SC_1$-$C_6$alkyl, —OH, —$NR^3R^4$, —$C(=O)NR^3R^4$, —$NR^3C(=O)OC_1$-$C_6$ alkyl, —$NR^3C(=O)NR^3R^4$, —$S(O)_xC_1$-$C_6$ alkyl, —$S(O)_yNR^3R^4$, —$NR^3S(O)_yNR^3R^4$, halogen, —CN, —$NO_2$, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which $R^a$ is attached is a carbon atom, wherein said heterocyclic ring is optionally substituted with 1-5 substituent groups independently selected from halogen, —$C_1$-$C_3$ alkyl, and —$OC_1$-$C_3$ alkyl, wherein —$C_1$-$C_3$ alkyl and —$OC_1$-$C_3$ alkyl are optionally substituted with 1-7 halogens;

wherein for compounds in which $R^a$ is selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —$OC_1$-$C_6$alkyl, —$OC_2$-$C_6$ alkenyl, —$OC_2$-$C_6$ alkynyl, —$OC_3$-$C_8$ cycloalkyl optionally having 1-3 double bonds, —$C(=O)C_1$-$C_6$alkyl, —$C(=O)C_3$-$C_8$ cycloalkyl, —$CO_2C_1$-$C_6$alkyl, —$C(=O)SC_1$-$C_6$alkyl, —$NR^3C(=O)OC_1$-$C_6$ alkyl, and —$S(O)_xC_1$-$C_6$ alkyl, $R^a$ is optionally substituted with 1-15 halogens and is optionally also substituted with 1-3 substituent groups independently selected from (a) —OH, (b) —CN, (c) —$NR^3R^4$, (d) —$C_3$-$C_8$ cycloalkyl optionally having 1-3 double bonds and optionally substituted with 1-15 halogens, (e) —$OC_1$-$C_4$alkyl optionally substituted with 1-9 halogens and optionally also substituted with 1-2 substituent groups independently selected from $OC_1$-$C_2$ alkyl and phenyl, (f) —$OC_3$-$C_8$ cycloalkyl optionally having 1-3 double bonds and optionally substituted with 1-15 halogens, (g) —$CO_2H$, (h) —$C(=O)CH_3$, (i) —$CO_2C_1$-$C_4$alkyl which is optionally substituted with 1-9 halogens, and (i) phenyl which is optionally substituted with 1-3 groups independently selected from halogen, —$CH_3$, —$CF_3$, —$OCH_3$, and —$OCF_3$;

p is an integer from 0-4;
q is 0 or 1;
x is 0, 1, or 2;
y is 1 or 2;

$R^3$ and $R^4$ are each independently selected from H, —$C_1$-$C_5$ alkyl, —$C(=O)C_1$-$C_5$ alkyl and —$S(O)_yC_1$-$C_5$ alkyl, wherein —$C_1$-$C_5$ alkyl in all instances is optionally substituted with 1-11 halogens;

$R^7$ and $R^8$ are each independently selected from the group consisting of H, —$C_1$-$C_6$ alkyl, —$C_2$-$C_6$ alkenyl, —$C_2$-$C_6$ alkynyl, —$C(=O)C_1$-$C_6$alkyl, —$CO_2H$, —$CO_2C_1$-$C_6$alkyl, —$C_3$-$C_8$ cycloalkyl which optionally comprises 1-2 double bonds, —$C(=O)C_3$-$C_8$ cycloalkyl which optionally comprises 1-2 double bonds, —$C(=O)$phenyl, —$C(=O)NR^3R^4$, —$S(O)_2C_1$-$C_6$ alkyl, and —$S(O)_2NR^3R^4$, wherein —$C_1$-$C_6$ alkyl in all instances is optionally substituted with 1-11 halogens and is optionally also substituted with 1-2 substituents independently selected from —$CO_2H$, —$CO_2C_1$-$C_6$alkyl which is optionally substituted with 1-11 halogens, —$NR^3R^4$, —OH, —$C(=O)H$—, a 5-7 membered heterocycle comprising 1-3 heteroatoms independently selected from N, O and S, —$C_3$-$C_8$ cycloalkyl, and phenyl, wherein said —$C_3$-$C_8$ cycloalkyl and phenyl groups are optionally substituted with (a) 1-5 substituents independently selected from (i) halogen, (ii) —$C_1$-$C_3$ alkyl optionally substituted with 1-5 halogens, and (iii) —$OC_1$-$C_3$ alkyl optionally substituted with 1-5 halogens, and (b) optionally also 1-2 groups independently selected from —$CO_2H$, —$CO_2C_1$-$C_4$alkyl, —$CH_2CO_2H$, —$CO_2CO_2C_1$-$C_4$alkyl, —$CH_2CH_2CO_2H$, —$CH_2CH_2CO_2C_1$-$C_4$alkyl, —$NR^3R^4$, —CN, —$NO_2$, —$C(=O)NR^3R^4$, —$CH_2C(=O)NR^3R^4$, —$S(O)_2C_1$-$C_3$ alkyl, and —$C_1$-$C_5$ alkyl substituted with 1-2 groups independently selected from —$NR^3R^4$, —OH, —$C(=O)H$—, and a 5-7 membered heterocycle comprising 1-3 heteroatoms independently selected from N, O and S, and optionally also 1-5 halogens; wherein said 5-7 membered heterocycle in all uses as a substituent on —$C_1$-$C_6$ alkyl is optionally substituted with 1-5 substituents independently selected from halogen, —$C_1$-$C_3$ alkyl and —$OC_1$-$C_3$ alkyl, said —$C_1$-$C_3$ alkyl and —$OC_1$-$C_3$ alkyl being optionally substituted with 1-7 halogens;

wherein when $R^7$ or $R^8$ is —$C_3$-$C_8$ cycloalkyl which optionally comprises 1-2 double bonds, then said —$C_3$-$C_8$ cycloalkyl which optionally comprises 1-2 double bonds is optionally substituted with (a) 1-5 substituents independently selected from halogen, —$C_1$-$C_3$ alkyl optionally substituted with 1-5 halogen, and —$OC_1$-$C_3$ alkyl optionally substituted with 1-5 halogens, and (b) optionally also 1 group selected from —$CO_2H$, —$CO_2C_1$-$C_4$alkyl, —$CH_2CO_2H$, —$CH_2CO_2C_1$-$C_4$alkyl, —$CH_2CH_2CO_2H$, —$CH_2CH_2CO_2C_1$-$C_4$alkyl, —$C(=O)NR^3R^4$, —$CH_2C(=O)NR^3R^4$, —$CH_2CH_2C(=O)NR^3R^4$, —CN, —$NO_2$, and —$S(O)_2C_1$-$C_3$ alkyl;

and when $R^7$ or $R^8$ is $C(=O)$phenyl or —$C(=O)C_3$-$C_8$ cycloalkyl which optionally comprises 1-2 double bonds, said phenyl or cycloalkyl which optionally comprises 1-2 double bonds is optionally substituted with (a) 1-5 substituents independently selected from halogen, —$C_1$-$C_3$ alkyl optionally substituted with 1-5 halogens, and —$OC_1$-$C_3$ alkyl optionally substituted with 1-5 halogens, and (b) optionally also 1 group selected from —$CO_2H$, —$CO_2C_1$-$C_4$alkyl, —$CH_2CO_2H$, —$CH_2CO_2C_1$-$C_4$alkyl, —$CH_2CH_2CO_2H$, —$CH_2CH_2CO_2C_1$-$C_4$alkyl, —C(=O)$NR^3R^4$, —$CH_2C$(=O)$NR^3R^4$, —$CH_2CH_2C$(=O)$NR^3R^4$, —CN, —$NO_2$, and —$S(O)_2C_1$-$C_3$ alkyl;

wherein alternatively $R^7$ and $R^8$ are joined to form a monocyclic 5-7-membered heterocycle optionally having 1-2 heteroatoms independently selected from N, O and $S(O)_x$ in addition to the N to which $R^7$ and $R^8$ are connected or a bicyclic or tricyclic heterocycle having 5-16 atoms and optionally having 1-5 heteroatoms independently selected from N, O and $S(O)_x$ in addition to the N to which $R^7$ and $R^8$ are connected, said heterocycle being saturated, partly unsaturated or aromatic, said heterocycle being optionally substituted with (a) 1-5 substituent groups independently selected from halogen, —$C_1$-$C_3$ alkyl optionally substituted with 1-5 halogens, and —$OC_1$-$C_3$ alkyl optionally substituted with 1-5 halogens, and (b) optionally 1 substituent selected from —$CO_2H$, —$CO_2C_1$-$C_4$alkyl, —$CH_2CO_2H$, —$CH_2CO_2C_1$-$C_4$alkyl, —$CH_2CH_2CO_2H$, and —$CH_2CH_2CO_2C_1$-$C_4$alkyl; and $R^{10}$ and $R^{11}$ are each independently selected from the group consisting of H and —$C_1$-$C_5$ alkyl, wherein —$C_1$-$C_5$ alkyl is optionally substituted with 1-11 halogens.

In the compounds of Formula I and in subsequent compounds, alkyl, alkenyl, and alkynyl groups can be either linear or branched, unless otherwise stated.

DETAILED DESCRIPTION OF THE INVENTION

Many of the compounds of this invention have a structure in accordance with Formula Ia, written below, or a pharmaceutically acceptable salt thereof:

Definitions

"Ac" is acetyl, which is $CH_3C$(=O)—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkylene" groups are alkyl groups that are difunctional rather than monofunctional. For example, methyl is an alkyl group and methylene (—$CH_2$—) is the corresponding alkylene group.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring having from 3 to 8 carbon atoms, unless otherwise stated (e.g., cycloalkyl may be defined as having one or more double bonds). The term also includes a cycloalkyl ring fused to an aryl group. Examples of cycloalkyl include cyclopropyl, cyclopentyl, cyclohexyl, cycloheptyl, and the like. "Cycloalkenyl" means a non-aromatic carbocyclic ring having one or more double binds.

"Aryl" (and "arylene") when used to describe a substituent or group in a structure means a monocyclic or bicyclic compound in which the rings are aromatic and which contains only carbon ring atoms. The term "aryl" can also refer to an aryl group that is fused to a cycloalkyl or heterocycle. Preferred "aryls" are phenyl and naphthyl. Phenyl is generally the most preferred aryl group.

"EDC" is 1-ethyl-3-(3-dimethylaminopropyl)carbodiimide.

"Heterocyclyl," "heterocycle," and "heterocyclic" means a fully or partially saturated or aromatic 5-6 membered ring containing 1-4 heteroatoms independently selected from N, S and O, unless otherwise stated.

"Benzoheterocycle" represents a phenyl ring fused to a 5-6-membered heterocyclic ring having 1-2 heteroatoms, each of which is O, N, or S, where the heterocyclic ring may be saturated or unsaturated. Examples include indole, benzofuran, 2,3-dihydrobenzofuran and quinoline.

"DIPEA" is diisopropylethylamine.

"Halogen" includes fluorine, chlorine, bromine and iodine.

"HOBT" is 1-Hydroxybenzotriazole.

"IPAC" is isopropyl acetate.

"Me" represents methyl.

"Weinreb amine" is N,O-dimethylhydroxylamine.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

Optical Isomers-Diastereomers-Geometric Isomers-Tautomers

Compounds of Formula I may contain one or more asymmetric centers and can thus occur as racemates, racemic mixtures, single enantiomers, diastereomeric mixtures and individual diastereomers. The present invention is meant to include all such isomeric forms of the compounds of Formula I and all mixtures of the compounds. When structures are shown with a stereochemical representation, other sterochemnical structures are also included individually and collectively, such as enantiomers, diastereoisomers (where diastereomers are possible), and mixtures of the enantiomers and/or diastereomers, including racemic mixtures.

Some of the compounds described herein may contain olefinic double bonds, and unless specified otherwise, are meant to include both E and Z geometric isomers.

Some of the compounds described herein may exist as tautomers. An example is a ketone and its enol form, known as keto-enol tautomers. The individual tautomers as well as mixtures thereof are encompassed with compounds of Formula I.

Compounds of Formula I having one or more asymmetric centers may be separated into diastereoisomers, enantiomers, and the like by methods well known in the art.

Alternatively, enantiomers and other compounds with chiral centers may be synthesized by stereospecific synthesis using optically pure starting materials and/or reagents of known configuration.

Some of the biphenyl and biaryl compounds herein are observed as mixtures of atropisomers (rotamers) in the NMR spectra. The individual atropisomers as well as mixtures thereof are encompassed with the compounds of this invention.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites—Prodrugs

Therapeutically active metabolites, where the metabolites themselves fall within the scope of the claimed invention, are also compounds of the current invention. Prodrugs, which are compounds that are converted to the claimed compounds as they are being administered to a patient or after they have been administered to a patient, are also compounds of this invention.

Utilities

Compounds of the current invention are potent inhibitors of CETP. They are therefore useful in treating diseases and conditions that are treated by inhibitors of CETP.

One aspect of the present invention provides a method for treating or reducing the risk of developing a disease or condition that may be treated or prevented by inhibition of CETP by administering a therapeutically effective amount of a compound of this invention to a patient in need of treatment. A patient is a human or mammal, and is most often a human. A "therapeutically effective amount" is the amount of compound that is effective in obtaining a desired clinical outcome in the treatment of a specific disease.

Diseases or conditions that may be treated with compounds of this invention, or which the patient may have a reduced risk of developing as a result of being treated with the compounds of this invention, include: atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity, endotoxemia, and metabolic syndrome.

The compounds of this invention are particularly effective in raising HDL-C and/or increasing the ratio of HDL-C to LDL-C. They are effective in reducing LDL-C. These changes in HDL-C and LDL-C may be beneficial in treating atherosclerosis, reducing or reversing the development of atherosclerosis, reducing the risk of developing atherosclerosis, or preventing atherosclerosis.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating the diseases for which compounds of Formula I are indicated, generally satisfactory results are obtained when the compounds of the present invention are administered at a daily dosage of from about 0.01 milligram to about 100 milligram per kilogram of animal or human body weight, preferably given as a single daily dose or in divided doses two to six times a day, or in sustained release form. In the case of a 70 kg adult human, the total daily dose will generally be from about 0.5 milligram to about 500 milligrams. For a particularly potent compound, the dosage for an adult human may be as low as 0.1 mg. The dosage regimen may be adjusted within this range or even outside of this range to provide the optimal therapeutic response.

Oral administration will usually be carried out using tablets. Examples of doses in tablets are 0.5 mg, 1 mg, 2 mg, 5 mg, 10 mg, 25 mg, 50 mg, 100 mg, 250 mg, and 500 mg. Other oral forms can also have the same dosages (e.g. capsules).

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered. Pharmaceutical compositions may also consist essentially of a compound of Formula I and a pharmaceutically acceptable carrier without other therapeutic ingredients.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of the invention (e.g. Formula I and Ia-Ij) may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different schedules.

When oral formulations are used, the drugs may be combined into a single combination tablet or other oral dosage form, or the drugs may be packaged together as separate tablets or other oral dosage forms. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of this invention (e.g. Formula I), and either administered separately or in the same pharmaceutical composition, include, but are not limited to, other compounds which improve a patient's lipid profile, such as (i) HMG-CoA reductase inhibitors, (which are generally statins, including lovastatin, simvastatin, rosuvastatin, pravastatin, fluvastatin, atorvastatin, rivastatin, itavastatin, pitavastatin, and other statins), (ii) bile acid sequestrants (cholestyramine, colestipol, dialkylaminoalkyl derivatives of a cross-linked dextran, Colestid®, LoCholest®, (iii) niacin and related compounds, such as nicotinyl alcohol, nicotinamide, and nicotinic acid or a salt thereof, (iv) PPARα agonists, such as gemfibrozil and fenofibric acid derivatives (fibrates), including clofibrate, fenofibrate, bezafibrate, ciprofibrate, and etofibrate, (v) cholesterol absorption inhibitors, such as stanol esters, beta-sitosterol, sterol glycosides such as tiqueside; and azetidinones, such as ezetimibe, (vi) acyl CoA:cholesterol acyltransferase (ACAT) inhibitors, such as avasimibe and melinamide, and including selective ACAT-1 and ACAT-2 inhibitors and dual inhibitors, (vii) phenolic anti-oxidants, such as probucol, (viii) microsomal triglyceride transfer protein (MTP)/ApoB secretion inhibitors, (ix) anti-oxidant vitamins, such as vitamins C and E and beta carotene, (x) thyromimetics, (xi) LDL (low density lipoprotein) receptor inducers, (xii) platelet aggregation inhibitors, for example glycoprotein IIb/IIIa fibrinogen receptor antagonists and aspirin, (xiii) vitamin B12 (also known as cyanocobalamin), (xiv) folic acid or a pharmaceutically acceptable salt or ester thereof, such as the sodium salt and the methylglucamine salt, (xv) FXR and LXR ligands, including both inhibitors and agonists, (xvi) agents that enhance ABCA1 gene expression, and (xvii) ileal bile acid transporters.

Preferred classes of therapeutic compounds that can be used with the compounds of this invention for use in improving a patient's lipid profile (i.e. raising HDL-C and lowering LDL-C) include one or both of statins and cholesterol absorption inhibitors Particularly preferred are combinations of compounds of this invention with simvastatin, ezetimibe, or both simvastatin and ezetimibe. Also preferred are combinations of compounds of this invention with statins other than simvastatin, such as lovastatin, rosuvastatin, pravastatin, fluvastatin, atorvastatin, rivastatin, itavastatin, and ZD4522.

Finally compounds of this invention can be used with compounds that are useful for treating other diseases, such as diabetes, hypertension and obesity, as well as other anti-atherosclerotic compounds. Such combinations may be used to treat one or more of such diseases as diabetes, obesity, atherosclerosis, and dyslipidemia, or more than one of the diseases associated with metabolic syndrome. The combinations may exhibit synergistic activity in treating these disease, allowing for the possibility of administering reduced doses of active ingredients, such as doses that otherwise might be sub-therapeutic.

Examples of other active ingredients that may be administered in combination with a compound of this invention include, but are not limited to, compounds that are primarily anti-diabetic compounds, including:

(a) PPAR gamma agonists and partial agonists, including glitazones and non-glitazones (e.g. pioglitazone, englitazone, MCC-555, rosiglitazone, balaglitazone, netoglitazone, T-131, LY-300512, and LY-818;

(b) biguanides such as metformin and phenformin;

(c) protein tyrosine phosphatase-1B (PTP-1B) inhibitors;

(d) dipeptidyl peptidase IV (DP-IV) inhibitors, including vildagliptin, sitagliptin, and saxagliptin;

(e) insulin or insulin mimetics, such as for example insulin lispro, insulin glargine, insulin zinc suspension, and inhaled insulin formulations;

(f) sulfonylureas, such as tolbutamide, glipizide, glimepiride, acetohexamide, chlorpropamide, glibenclamide, and related materials;

(g) α-glucosidase inhibitors (such as acarbose, adiposine; camiglibose; emiglitate; miglitol; voglibose; pradimicin-Q; and salbostatin);

(h) PPARα/γ dual agonists, such as muraglitazar, tesaglitazar, farglitazar, and naveglitazar;

(i) PPARδ agonists such as GW501516 and those disclosed in WO97/28149;

(j) glucagon receptor antagonists;

(k) GLP-1; GLP-1 derivatives; GLP-1 analogs, such as exendins, such as for example exenatide (Byetta); and non-peptidyl GLP-1 receptor agonists;

(l) GIP-1; and (m) Non-sulfonylurea insulin secretagogues, such as the meglitinides (e.g. nateglinide and rapeglinide).

These other active ingredients that may be used in combination with the current invention also include antiobesity compounds, including 5-HT(serotonin) inhibitors, neuropeptide Y5 (NPY5) inhibitors, melanocortin 4 receptor (Mc4r) agonists, cannabinoid receptor 1 (CB-1) antagonists/inverse agonists, and $\beta_3$ adrenergic receptor agonists. These are listed in more detail later in this section.

These other active ingredients also include active ingredients that are used to treat inflammatory conditions, such as aspirin, non-steroidal anti-inflammatory drugs, glucocorticoids, azulfidine, and selective cyclooxygenase-2 (COX-2) inhibitors, including etoricoxib, celecoxib, rofecoxib, and Bextra.

Antihypertensive compounds may also be used advantageously in combination therapy with the compounds of this invention. Examples of antihypertensive compounds that may be used with the compounds of this invention include (1) angiotensin II antagonists, such as losartan; (2) angiotensin converting enzyme inhibitors (ACE inhibitors), such as enalapril and captopril; (3) calcium channel blockers such as nifedipine and diltiazam; and (4) endothelian antagonists.

Anti-obesity compounds may be administered in combination with the compounds of this invention, including: (1) growth hormone secretagogues and growth hormone secretagogue receptor agonists/antagonists, such as NN703, hexarelin, and MK-0677; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, and SR 59119A; (6) pancreatic lipase inhibitors, such as orlistat (Xenical®), Triton WR1339, RHC80267, lipstatin, tetrahydrolipstatin, teasaponin, and diethylumbelliferyl phosphate; (7) neuropeptide Y1 antagonists, such as BIBP3226, J-115814, BIBO 3304, LY-357897, CP-671906, and GI-264879A; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists; (10) melanin-concentrating hormone 1 receptor (MCH1R) antagonists, such as T-226296 (Takeda); (11) melanin-concentrating hormone 2 receptor (MCH2R) agonist/antagonists; (12) orexin-1 receptor antagonists, such as SB-334867-A; (13) melanocortin agonists, such as Melanotan II; (14) other Mc4r (melanocortin 4 receptor) agonists, such as CHIR86036 (Chiron), ME-10142, and ME-10145 (Melacure), CHIR86036 (Chiron); PT-141, and PT-14 (Palatin); (15) 5HT-2 agonists; (16) 5HT2C (serotonin receptor 2C) agonists, such as BVT933, DPCA37215, WAY161503, and R-1065; (17) galanin antagonists; (18) CCK agonists; (19) CCK-A (cholecystolinin-A) agonists, such as AR-R 15849, GI 181771, JMV-180, A-71378, A-71623 and SR146131; (20) GLP-1 agonists; (21) corticotropin-releasing hormone agonists; (22) histamine receptor-3 (H3) modulators; (23) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, and GT2394 (Gliatech); (24) β-hydroxy steroid dehydrogenase-1 inhibitors (11β-HSD-1 inhibitors), such as BVT 3498 and, BVT 2733, (25) PDE (phosphodiesterase) inhibitors, such as theophylline, pentoxifylline, zaprinast, sildenafil, amrinone, milrinone, cilostamide, rolipram, and cilomilast; (26) phosphodiesterase-3B (PDE3B) inhibitors; (27) NE (norepinephrine) transport inhibitors, such as GW 320659, despiramine, talsupram, and nomifensine; (28) ghrelin receptor antagonists; (29) leptin, including recombinant human leptin (PEG-OB, Hoffman La Roche) and recombinant methionyl human leptin (Amgen); (30) leptin derivatives; (31) BRS3 (bombesin receptor subtype 3) agonists such as [D-Phe6,beta-Ala11,Phe13,Nle14]Bn(6-14) and [D-Phe6, Phe13]Bn(6-13)propylamide; (32) CNTF (Ciliary neurotrophic factors), such as GI-181771 (Glaxo-SmithKline), SR146131 (Sanofi Synthelabo), butabindide, PD170,292, and PD 149164 (Pfizer); (33) CNTF derivatives, such as axokine (Regeneron); (34) monoamine reuptake inhibitors, such as sibutramine; (35) UCP-1 (uncoupling protein-1, 2, or 3) activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; (36) thyroid hormone β agonists, such as KB-2611 (KaroBioBMS); (37) FAS (fatty acid synthase) inhibitors, such as Cerulenin and C75; (38) DGAT1 (diacylglycerol acyltransferase 1) inhibitors; (39) DGAT2 (diacylglycerol acyltransferase 2) inhibitors; (40) ACC2 (acetyl-CoA carboxylase-2) inhibitors; (41) glucocorticoid antagonists; (42) acyl-estrogens, such as oleoyl-estrone; (43) dicarboxylate transporter inhibitors; (44) peptide YY, PYY 3-36, peptide YY analogs, derivatives, and fragments such as BIM-43073D, BIM43004C, (45) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (46) Neuropeptide Y4 (NPY4) agonists such as pancreatic peptide (PP); (47) Neuropeptide Y1 (NPY1) antagonists such as BIBP3226, J-115814, BIBO 3304, LY-357897, CP-671906, and GI-264879A; (48) Opioid antagonists, such as nalmefene (Revex®), 3-methoxynaltrexone, naloxone, and naltrexone; (49) glucose transporter inhibitors; (50) phosphate transporter inhibitors; (51) 5-HT (serotonin) inhibitors; (52) beta-blockers; (53) Neurokinin-1 receptor antagonists (NK-1 antagonists); (54) clobenzorex; (55) cloforex; (56) clominorex; (57) clortermine; (58) cyclexedrine; (59) dextroamphetamine; (60) diphemethoxidine, (61) N-ethylamphetamine; (62) fenbutrazate; (63) fenisorex; (64) fenproporex; (65) fludorex; (66) fluminorex; (67) furfurylmethylamphetamine; (68) levamfetamine; (69) levophacetoperane; (70) mefenorex; (71) metamfepramone; (72) methamphetamine; (73) norpseudoephedrine; (74) pentorex; (75) phendimetrazine; (76) phenmetrazine; (77) picilorex; (78) phytopharm 57; (79) zonisamide, (80) aminorex; (81) amphechloral; (82) amphetamine; (83) benzphetamine; and (84) chlorphentermine.

The combination therapies described above which use the compounds of this invention may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease. The combinations described above may ameliorate more than one symptom of metabolic syndrome concurrently (e.g. two symptoms, three symptoms, four symptoms, or all five of the symptoms).

CETP Assay

An in vitro continuous assay for determining $IC_{50}$'s to identify compounds that are CETP inhibitors was performed based on a modification of the method described by Epps et al. employing BODIPY®-CE as the cholesteryl ester lipid donor. See Epps et al.(1995) *Method for measuring the activities of cholesteryl ester transfer protein (lipid transfer protein)*, Chem. Phys. Lipids. 77, 51-63.

Particles used in the assay were created from the following sources: Synthetic donor HDL particles containing DOPC (Dioleoyl Phosphatidyl Choline), BODIPY®-CE (Molecular Probes C-3927), triolein (a triglyceride), and apoHDL were essentially created by probe sonication as described by Epps et al, but with the addition of a non-diffusable quencher molecule, dabcyl dicetylamide, in order to reduce background fluorescence. Dabcyl dicetylamide was made by heating dabcyl n-succinimide with dicetylamine in DMF at 95° C. overnight in the presence of diisopropylamine catalyst. Native lipoproteins from human blood were used as acceptor particles. Particles having a density less than 1.063 g/ml were collected by ultracentrifugation. These particles include VLDL, IDL, and LDL. Particle concentrations were expressed in terms of protein concentration as determined by BCA assay (Pierce, USA). Particles were stored at 4° C. until use.

Assays were performed in Dynex Microfluor 2 U-bottom black 96-well plates (Cat #7205). An assay cocktail containing CETP, 1×CETP buffer (50 mM Tris, pH 7.4, 100 mM NaCl, 1 mM EDTA), and half the final concentration of acceptor particles was prepared, and 100 μL of the assay cocktail was added to each well of the plate. Test compounds in DMSO were added in a volume of 3 μL. The plate was mixed on a plate shaker and then incubated at 25° C. for 1 hour. A second assay cocktail containing donor particles, the remaining acceptor particles and 1×CETP buffer was prepared. 47 μL of the second assay cocktail was added to the reaction wells to start the assay. Assays were performed at 25° C. in a final volume of 150 μL. Final concentrations of materials were: 5 ng/μL donor particles, 30 ng/μL acceptor particles (each expressed by protein content), 1×CETP buffer, 0.8 nM recombinant human CETP (expressed in CHO cells and partially purified), and up to 2% DMSO when testing compounds. The assay was followed in a fluorescence plate reader (Molecular Devices Spectramax GeminiXS) set for a 45 minute kinetic run at 25° C. which read the samples every 45 sec at Ex=480 nm, Em=511 nm, with a cutoff filter at 495 nm, photomultiplier tube setting of medium, calibration on, and 6 reads/well.

Data was evaluated by obtaining an initial rate, expressed in relative fluorescence units per second, for the pseudolinear portion of the curve, often 0-500 or 1000 sec. Comparison of the rates of samples with inhibitors to an uninhibited (DMSO only) positive control yielded a percent inhibition. A plot of percent inhibition vs. log of inhibitor concentration, fit to a Sigmoidal 4 parameter equation was used to calculate $IC_{50}$.

EXAMPLES

The following schemes and examples are provided so that the invention will be more fully appreciated and understood. Starting materials are made using known procedures or as shown below.

The examples should not be construed as limiting the invention in any way. The scope of the invention is defined by the appended claims. Compounds of this invention have an $IC_{50}$ value as measured using the assay described above of less than 50 μM. Compounds preferably have an $IC_{50}$ in the range of 5 nM to 10 μM, more preferably in the range of 5 nM to 1 μM, even more preferably in the range of 5 nM to 200 nM, and still more preferably in the range of 5 nM to 100 nM.

SCHEME 1

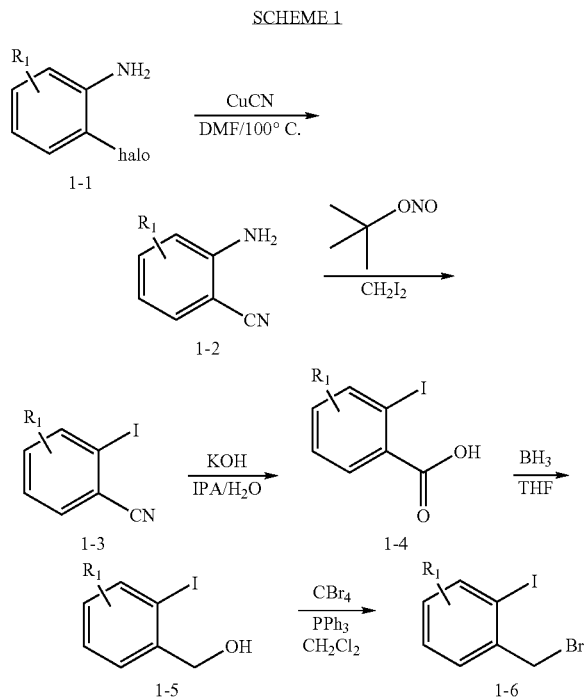

SCHEME 2

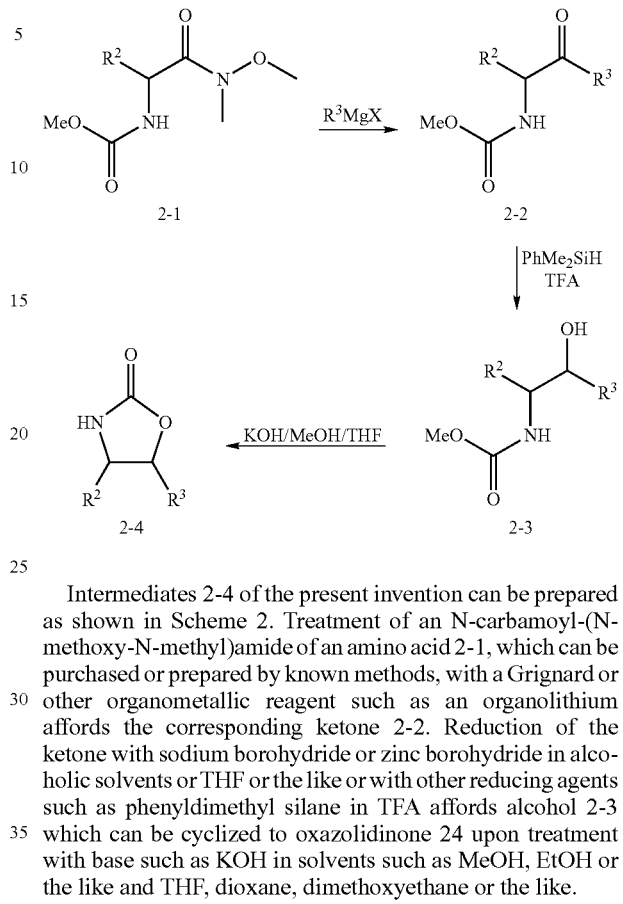

Intermediates 2-4 of the present invention can be prepared as shown in Scheme 2. Treatment of an N-carbamoyl-(N-methoxy-N-methyl)amide of an amino acid 2-1, which can be purchased or prepared by known methods, with a Grignard or other organometallic reagent such as an organolithium affords the corresponding ketone 2-2. Reduction of the ketone with sodium borohydride or zinc borohydride in alcoholic solvents or THF or the like or with other reducing agents such as phenyldimethyl silane in TFA affords alcohol 2-3 which can be cyclized to oxazolidinone 24 upon treatment with base such as KOH in solvents such as MeOH, EtOH or the like and THF, dioxane, dimethoxyethane or the like.

Intermediates 1-2, 1-3 and 1-4 utilized in the present invention can be purchased or prepared as shown in Scheme 1. An appropriately substituted 2-haloaniline 1-1 where the halogen is preferably iodo or bromo is treated with CuCN in DMF at elevated temperature to afford the corresponding 2-cyanoaniline 1-2. Alternatively, the nitrite can be prepared by treatment of 1-1 with KCN and CuI in the presence of a palladium (II) salt or in the presence of certain copper or nickel complexes (See: Smith, M. B. and March, J. "March's Advanced Organic Chemistry", 5$^{th}$ Ed., John Wiley and Sons, New York, pp. 867 (2001) and references therein). Iodides 1-3 are prepared by treatment of 1-2 with isoamylnitrite, n-pentylnitrite, t-butyl nitrite or the like in diiodomethane (see for example: Smith et al., *J. Org. Chem.* 55, 2543, (1990) and references cited therein). Alternatively, the iodide can be prepared first by diazonium formation using isoamylnitrite, n-pentylnitrite, t-butyl nitrite, sodium nitrite, nitrous acid or the like followed by heating in the presence of an iodide salt such as copper iodide, sodium iodide, potassium iodide, tetrabutylammonium iodide or the like. Hydrolysis of iodo-nitrile 1-3 is carried out using potassium hydroxide in isopropanol and water to afford the iodoacid 1-4. Further reduction with borane, lithium aluminum hydride, lithium borohydride or the like in ether, tetrahydrofuran, dimethoxyethane or the like affords the 2-iodo alcohols 1-5. Intermediates 1-5 can be transformed into benzyl bromides 1-6 using reagents such as triphenylphosphine and carbon tetrabromide in solvents such as dichloromethane or the like (see Smith, M. B. and March, J. "March's Advanced Organic Chemistry", 5$^{th}$ Ed., John Wiley and Sons, New York, pp. 518-519 (2001) and references therein).

SCHEME 3

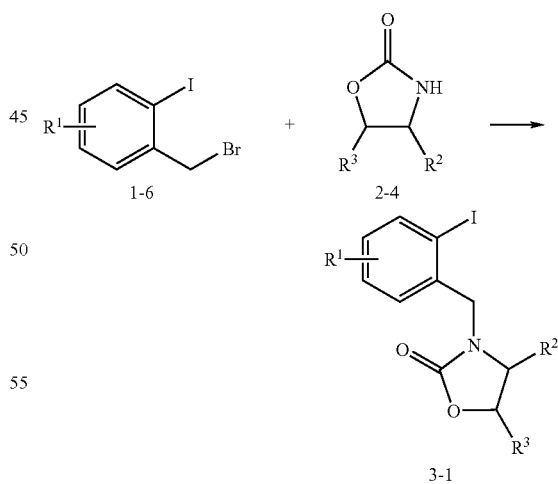

Compounds of the present invention 3-1 can be prepared as shown in Scheme 3. Oxazolidinones 2-4, prepared as shown in Scheme 2, can be alkylated with benzyl bromide 1-6, which is prepared as shown in Scheme 1, using bases such as sodium hexamethyldisilazide or sodium hydride in solvents like tetrahydrofuran, dimethoxyethane, diethyl ether or the like to afford products 3-1.

SCHEME 4

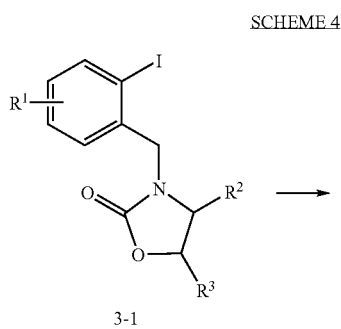

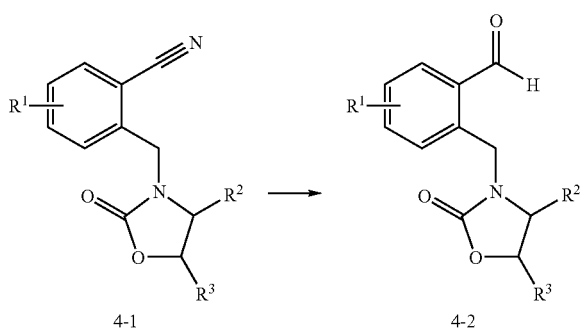

Compounds of the present invention 4-2 can be prepared as shown in Scheme 4. Compound 3-1, prepared as shown in Scheme 3 can be treated with CuCN in DMF at elevated temperature to afford the corresponding nitrile 4-1. Alternatively, the nitrile can be prepared by treatment of 3-1 with KCN and CuI in the presence of a palladium (D) salt or in the presence of certain copper or nickel complexes (See: Smith, M. B. and March, J. "March's Advanced Organic Chemistry", 5$^{th}$ Ed., John Wiley and Sons, New York, pp. 867 (2001) and references therein). Nitrile 4-1 can be treated with PtO$_2$ and formic acid at elevated temperatures to produce aldehyde 4-2. For alternative methods to convert nitrites to aldehydes, see: Smith, M. B. and March, J. "March's Advanced Organic Chemistry", 5$^{th}$ Ed., John Wiley and Sons, New York, pp. 1204-1205 (2001) and references therein.

SCHEME 5

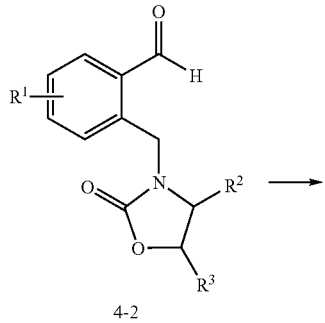

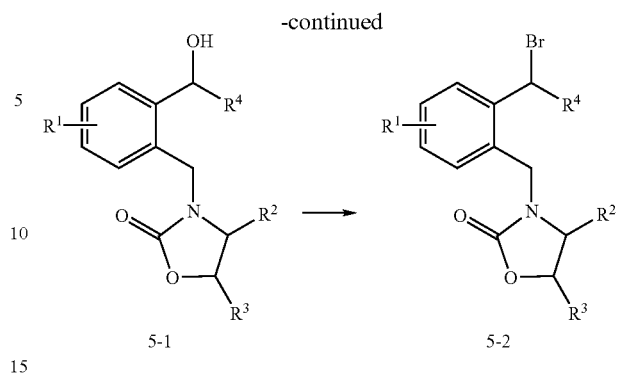

Aldehydes 4-2, prepared as shown in Scheme 4, can be transformed to alcohols 5-1 as shown in Scheme 5. For the case in which R$^4$=H, aldehyde 4-2 is treated with NaBH$_4$ in an alcoholic solvent, such as MeOH, EtOH, or the like. For other methods to reduce aldehydes to primary alcohols, see: Smith, M. B. and March, J. "March's Advanced Organic Chemistry", 5$^{th}$ Ed., John Wiley and Sons, New York, pp. 1197-1203 (2001) and references therein. For the case in which R$^4$≠H (i.e. alkyl, aryl, etc.), aldehyde 4-2 is treated with a Grignard reagent or organolithium in a solvent such as Et$_2$O, THF, or the like. For the addition of Grignards and organolithiums as well as other reagents such as organozincs to aldehydes, see: Smith, M. B. and March, J. "March's Advanced Organic Chemistry", 5$^{th}$ Ed., John Wiley and Sons, New York, pp. 1205-1213 (2001) and references therein. Alcohols 5-1 can be transformed to bromides 5-2 using reagents such as triphenylphosphine and carbon tetrabromide in solvents such as dichloromethane or the like (see Smith, M. B. and March, J. "March's Advanced Organic Chemistry", 5$^{th}$ Ed., John Wiley and Sons, New York, pp. 518-519 (2001) and references therein).

SCHEME 6

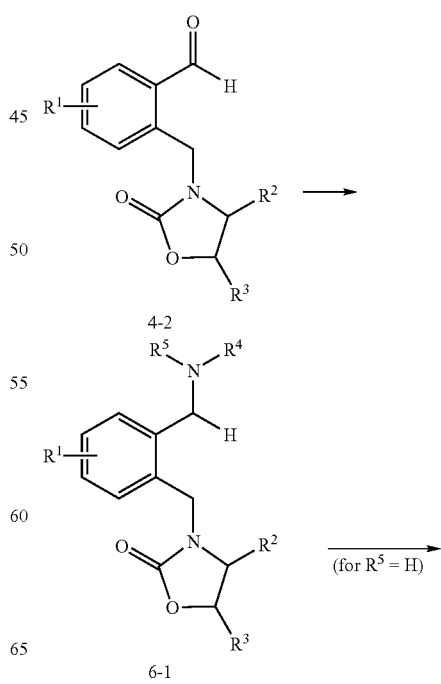

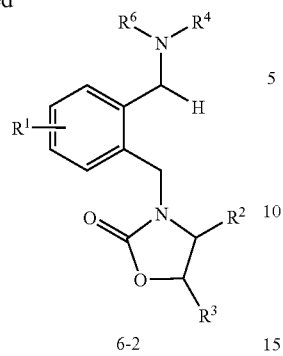

6-2

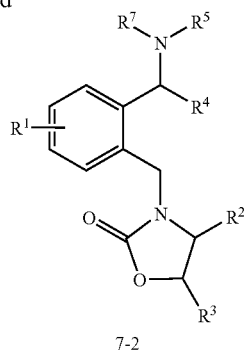

7-2

Amines 6-1 and 6-2 can be prepared as shown in Scheme 6. Aldehydes 4-2, prepared as shown in Scheme 4, can be treated with an amine ($R^4NH_2$ or $R^4R^5NH$) in the presence of a reducing reagent, such as $NaBH_3CN$ or sodium triacetoxyborohydride or the like, in a solvent such as MeOH, methylene chloride, dichloroethane, or the like, with or without an acid additive, to produce amines 6-1 (see Smith, M. B. and March, J. "March's Advanced Organic Chemistry", 5$^{th}$ Ed., John Wiley and Sons, New York, pp. 1187-1189 (2001) and references therein). For the case in which $R^5$=H, a second reaction can be carried out to produce compounds 6-2. Thus, for $R^5$=H, treatment of 6-1 with an an aldehyde or ketone in the presence of a reducing reagent, such as $NaBH_3CN$ or sodium triacetoxyborohydride or the like, in a solvent such as MeOH, methylene chloride, dichloroethane, or the like, with or without an acid additive, produces amines 6-2. Alternatively, 6-1 (where $R^5$=H) may be treated with an alkyl halide, preferably a bromide or iodide in a solvent such as acetonitrile, THF, or the like, to give 6-2 (see Smith, M. B. and March, J. "March's Advanced Organic Chemistry", 5$^{th}$ Ed., John Wiley and Sons, New York, pp. 499-501 (2001) and references therein).

Amines 7-1 and 7-2 can be prepared as shown in Scheme 7. Bromides 5-2, prepared as shown in Scheme 5, can be treated with an amine ($R^5NH_2$ or $R^5R^6NH$) in a solvent such as acetonitrile or the like at room temperature or elevated temperatures with or without at tertiary base, such as DIPEA, $Et_3N$ or the like to produce amines 7-1 (see Smith, M. B. and March, J. "March's Advanced Organic Chemistry", 5$^{th}$ Ed., John Wiley and Sons, New York, pp. 499-501 (2001) and references therein). For the case in which $R^6H$, a second reaction can be carried out to produce compounds 7-2. Thus, for $R^6$=H, treatment of 7-1 with an aldehyde or ketone in the presence of a reducing reagent, such as $NaBH_3CN$ or sodium triacetoxyborohydride or the like, in a solvent such as MeOH, methylene chloride, dichloroethane, or the like, with or without an acid additive, produces amines 7-2 (see Smith, M. B. and March, J. "March's Advanced Organic Chemistry", 5$^{th}$ Ed., John Wiley and Sons, New York, pp. 1187-1189 (2001) and references therein). Alternatively, 7-1 (where $R^6H$) may be treated with an alkyl halide, preferably a bromide or iodide in a solvent such as acetonitrile, THF, or the like, to give 7-2 (see Smith, M. B. and March, J. "March's Advanced Organic Chemistry", 5$^{th}$ Ed., John Wiley and Sons, New York, pp. 499-501 (2001) and references therein).

SCHEME 7

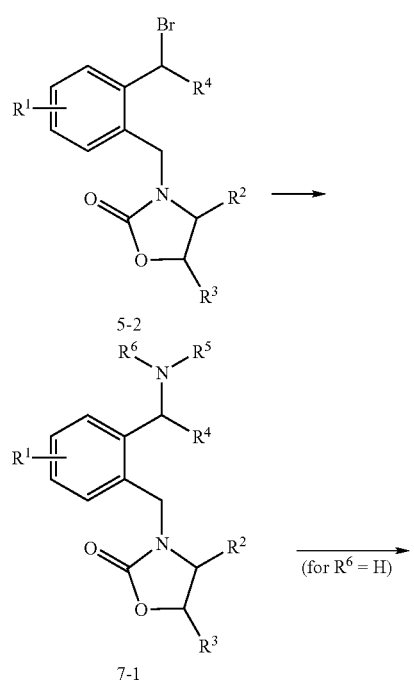

Scheme 8

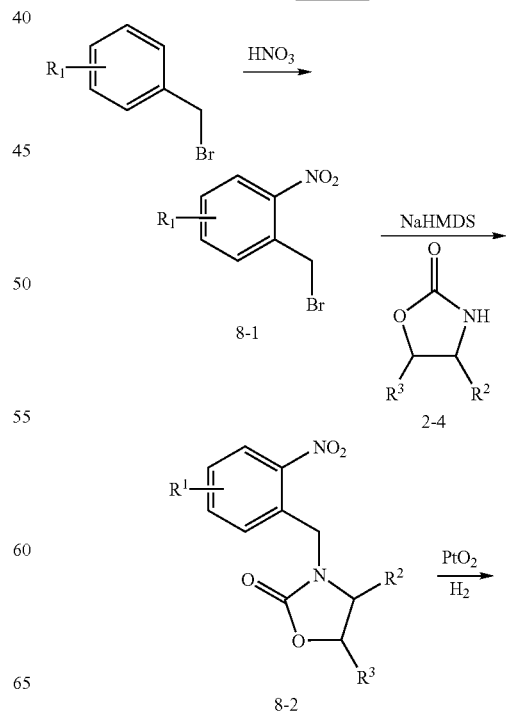

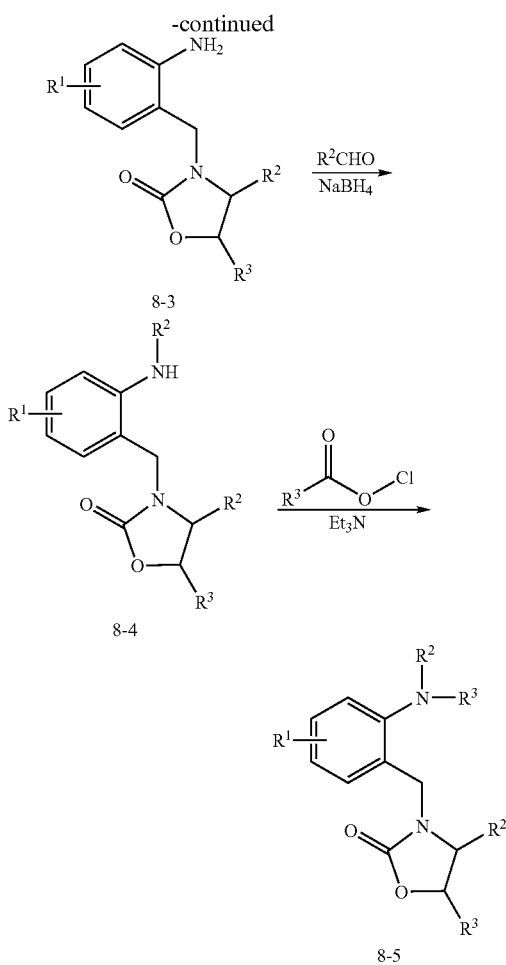

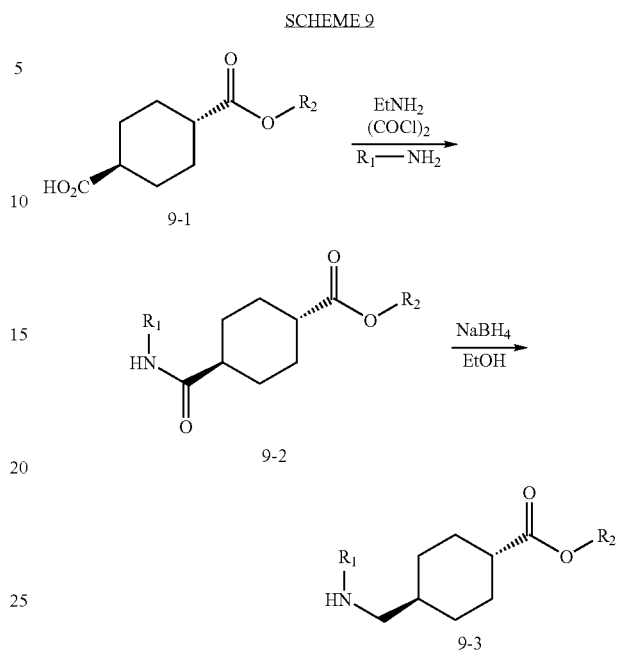

Compounds of the present invention can be prepared according to Scheme 8. Treatment of an appropriately substituted benzyl bromide, which can be purchased or prepared by known methods, with fuming nitric acid gave the appropriately substituted nitrobenzene 8-1. Oxazolidinones 2-4, prepared as shown in Scheme 2, can be alkylated with nitrobenzene 8-1, using bases such as sodium hexamethyldisilazide or sodium hydride in solvents like tetrahydrofuran, dimethoxyethane, diethyl ether or the like to afford nitrobenzene 8-2. Reduction of the nitro group in 8-2 can be achieved with platinum oxide under hydrogen atmosphere to afford the amine 8-3. Alternative methods for the reduction of a nitro group to an amine can be found in "March's Advanced Organic Chemistry", 5th Ed., John Wiley and Sons, New York, pp. 1552, 1558 (2001) and references therein. Amines 8-3 can be treated with aldehydes, in the presence of a reducing agent such as NaBH$_3$CN or sodium triacetoxyborohydride or the like, in a solvent such as MeOH, methylene chloride, dichloroethane, or the like, with or without an acid additive, to produce amines 8-4. A second reaction can be carried out to produce compounds 8-5. Alternatively, amines 8-4 may be treated with an alkyl halide or alkyl chloroformate, preferably a bromide or iodide in a solvent such as acetonitrile, THF, or the like to give 8-5.

Compounds of the present invention can be prepared according to Scheme 9. Acids 9-1, prepared by known methods or purchased commercially, can be treated with oxalyl chloride and an appropriate amine in solvents such as methylene chloride or the like to afford amides 9-2. Reduction of amide 9-2 under standard conditions such as sodium borohydride in an alcohol solvent such as ethanol, methanol or the like affords amines 9-3. For alternative methods of reduction of amides see "March's Advanced Organic Chemistry", 5th Ed., John Wiley and Sons, New York, pp. 1549 (2001) and references therein.

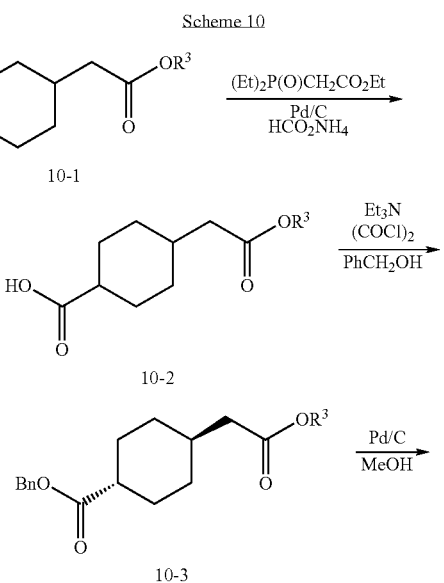

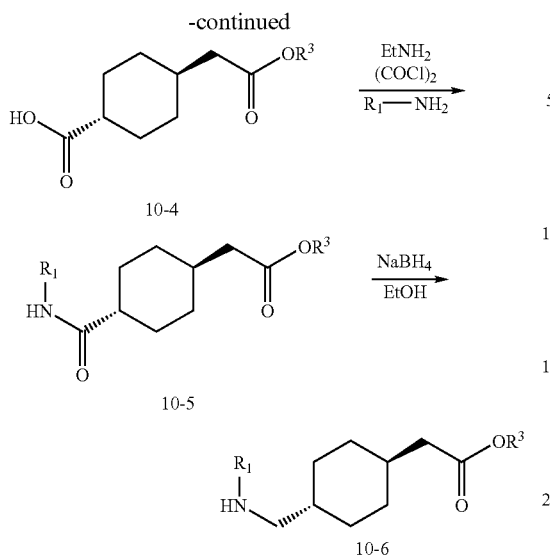

Compounds of the present invention 10-6 can be prepared according to Scheme 10. Ketones 10-1, prepared according to known procedures or purchased commercially, can be converted to acids 10-2 by reaction with triethyl phosphonoacetate in the presence of sodium ethoxide and ethanol or the like followed by reaction with palladium on carbon catalyst and ammonium formate. Conversion to the benzyl ester 10-3 allows separation of the trans isomer which is deprotected using palladium on carbon catalyst under hydrogen pressure to afford the trans acid 100-4. Conversion to the amine 10-6 is carried out as described previously in Scheme 9.

Scheme 11

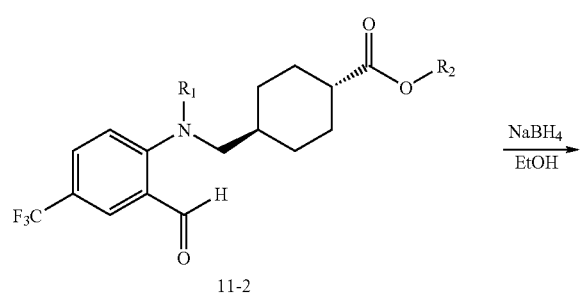

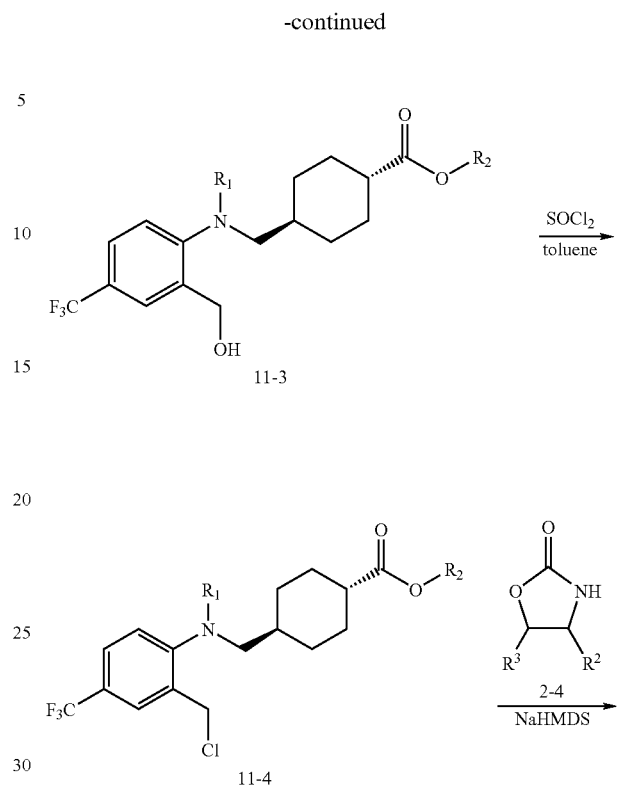

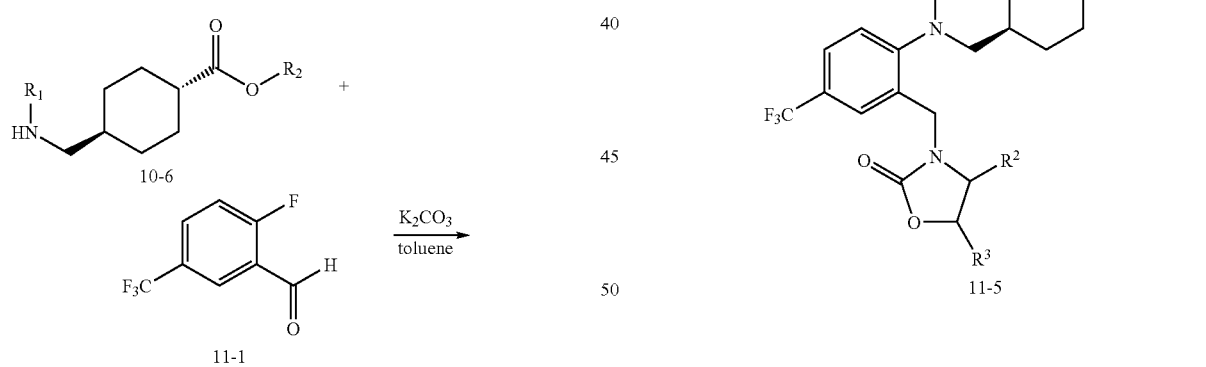

Compounds of the present invention 11-5 can be prepared as shown in Scheme 11. Amine 10-6, prepared as described in Scheme 10, can be treated with aldehyde 111-1 in the presence of a weak base such as potassium carbonate or the like in solvents such as toluene, THF or the like to afford aldehydes 11-2. Reduction of aldehyde 11-2 can be performed with sodium borohydride in solvents such as methanol or the like to afford alcohol 11-3. Treatment of 11-3 with thionyl chloride in solvents such as toluene or the like affords chlorides 11-4 which can be alkylated with oxazolidinones 2-4 as described previously in Scheme 3.

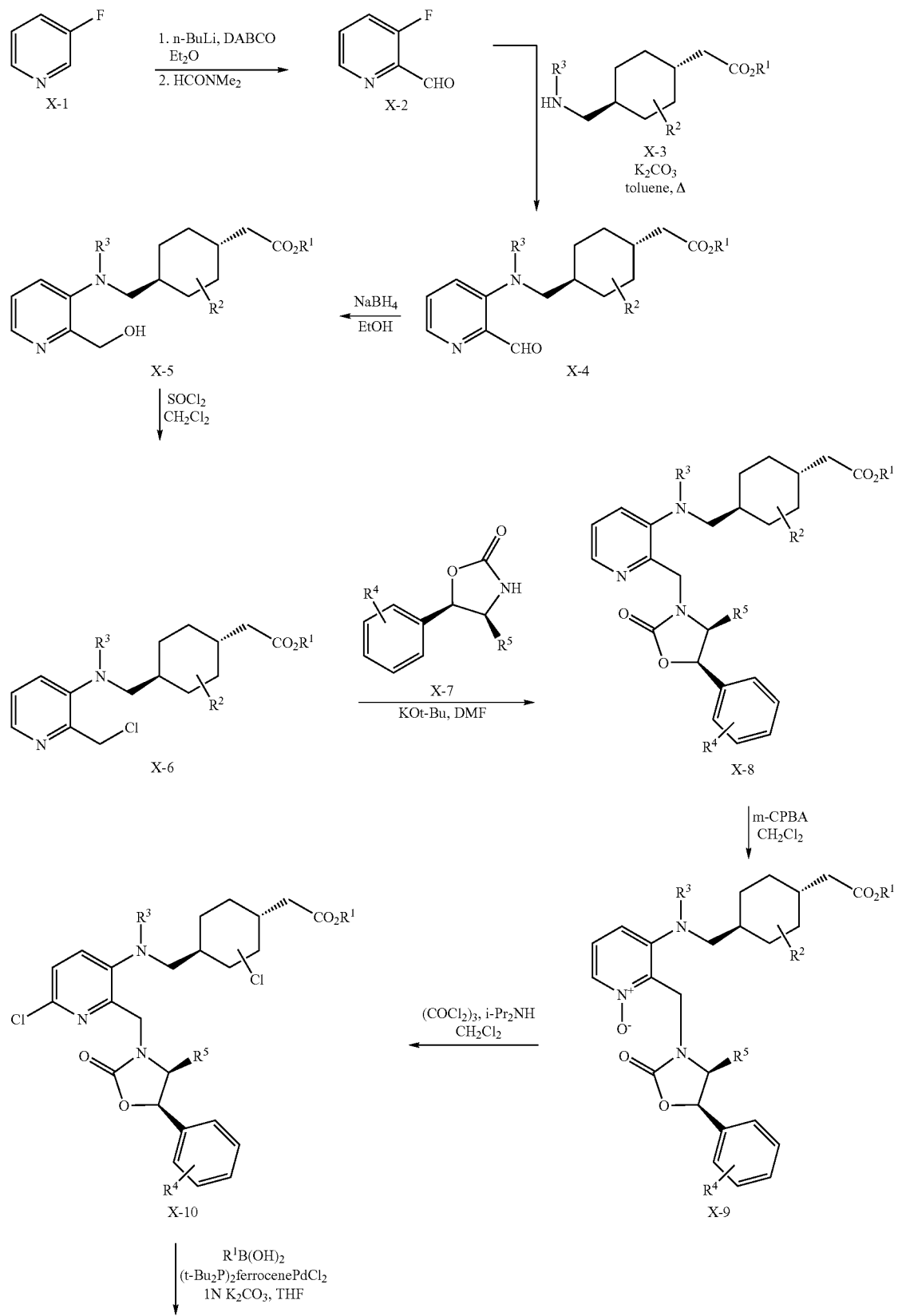

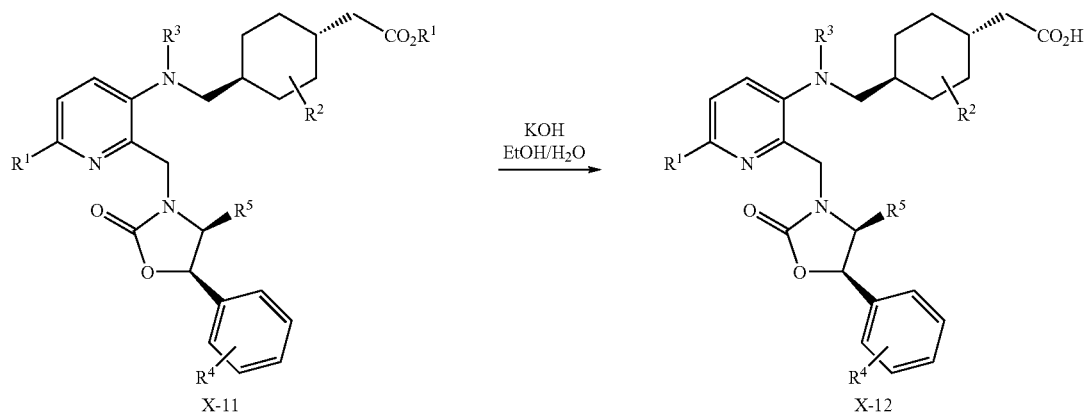

Intermediates of the present invention wherein $R^1$, $R^2$, $R^3$, $R^4$, and $R^5$ are described in the claims can be prepared as shown in Scheme X. The pyridyl aldehyde X-2 can be obtained by metallation of an appropriately substituted fluoropyridine X-1, which can be purchased or prepared by known methods, with bases such as that generated by treatment of 1,4-diazobicyclo[2.2.2]-octane with n-butyl lithium followed by treatment with dimethylformamide or ethyl formate. Aryl fluoride X-2 can be heated with amine X-3 in the presence of bases such as potassium carbonate in solvents such as toluene or the like to afford pyridyl amine X-4. Reduction of aldehyde X-4 with reagents such as sodium borohydride in solvents such as MeOH, EtOH or the like affords pyridyl methyl alcohol X-5. Treatment of X-5 with reagents such as thionyl chloride in $CH_2Cl_2$ or the like affords pyridyl methyl chloride X-6. Oxazolidinones X-7, prepared as shown in Scheme Y can be alkylated with pyridyl methyl chloride X-6 using bases such as potassium t-butoxide, sodium hexamethyldisilazide or sodium hydride in solvents like DMF, tetrahydrofuran, dimethoxyethane, diethyl ether or the like to afford products X-8. Oxidation of pyridine X-8 with oxidants such as m-chloroperoxybenzoic acid or hydrogen peroxide in solvents such as $CH_2Cl_2$ or the like affords pyridine N-oxide X-9. Treatment of X-9 with triphosgene in the presence of bases such as diisopropylamine or the like in solvents such as $CH_2Cl_2$ or the like affords pyridyl chloride X-10. Compound X-11 is prepared via a Suzuki or Stille reaction or variation thereof employing palladium catalyzed cross coupling of pyridyl chloride X-10 with an appropriately substituted alkyl-, aryl- or heteroaryl-boronic acid, -boronate ester or -trialkyl tin as described in Miyaua et al. *Chem. Rev.* 95, 2457 (1995) and references cited within and as described in Smith, M. B. and March, J. "March's Advanced Organic Chemistry", $5^{th}$ Ed., John Wiley and Sons, New York, pp. 868-869 (2001) and references cited therein. Treatment of X-11 with bases such as aqueous sodium hydroxide, potassium hydroxide or the like in solvents such as MeOH, EtOH or the like affords carboxylic acid X-12.

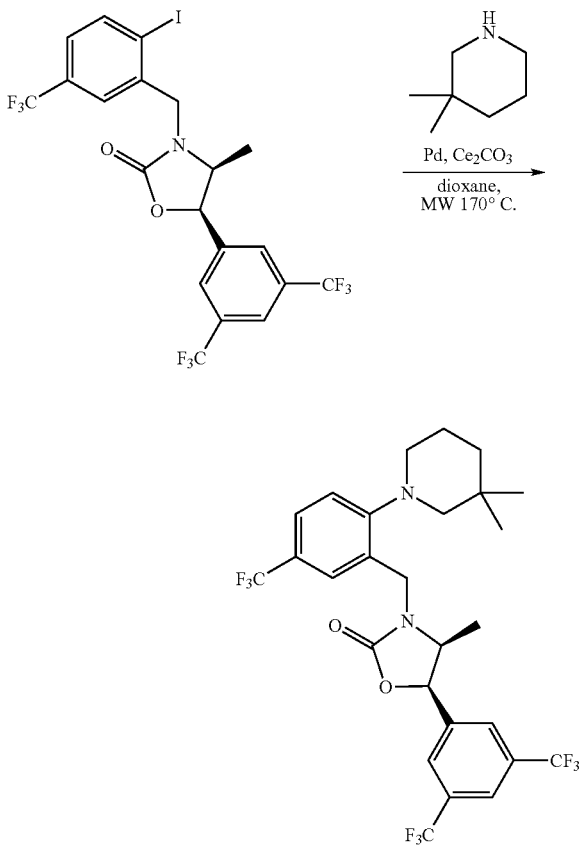

The method shown above for attaching a piperidine ring to a phenyl of the ring system is generally applicable to other secondary amines, including cyclic amines, such as pyrrolidine and morpholine.

Intermediate 1

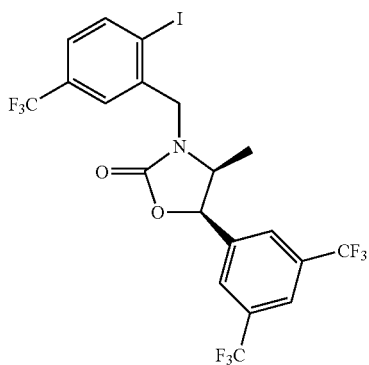

(4S,5R)-5-[3,5-bis(trifluoromethyl)phenyl]-3-[2-iodo-5-(trifluoromethyl)benzyl]-4-methyl-1,3-oxazolidin-2-one (4S,5R)-5-[3,5-bis(trifluoromethyl)phenyl]-4-methyl-1,3-oxazolidin-2-one (Intermediate 17,400 mg, 1.28 mmol) was treated with NaH (60% in oil, 128 mg, 3.2 mmol) and 2-(bromomethyl)-1-iodo-4-(trifluoromethyl)benzene (Intermediate 11, 466 mg, 1.28 mmol). The reaction was stirred at room temperature for 18 h. The reaction was quenched with H$_2$O (1 mL) and partitioned between EtOAc (80 mL) and H$_2$O (25 mL). The aqueous phase was re-extracted with EtOAc (2×20 mL) and the combined organic extracts were washed with brine (30 mL), dried (MgSO$_4$) and concentrated in vacuo to give the crude product. This was purified by flash silica-gel chromatography (0-30% EtOAc in hexanes gradient) to afford (4S,4R)-5-[3,5-bis(trifluoromethyl)phenyl]-3-[2-iodo-5-(trifluoromethyl)benzyl]-4-methyl-1,3-oxazolidin-2-one as a white solid. LCMS=598.0 (M+1)$^+$. $^1$H NMR (CDCl$_3$, 500 MHz): δ 8.06 (d, J=8.2 Hz, 1 H), 7.93 (s, 1 H), 7.82 (s, 2 H), 7.61 (s, 1 H), 7.33 (dd, J=8.2, 1.4 Hz, 1 H), 5.79 (d, J=7.8 hz, 1 H), 4.91 (d, J=16 Hz, 1 H), 4.40 (d, J=16 Hz, 1 H), 4.16-4.06 (m, 1 H), 0.83 (d, J=6.4 Hz, 3 H).

Intermediate 2

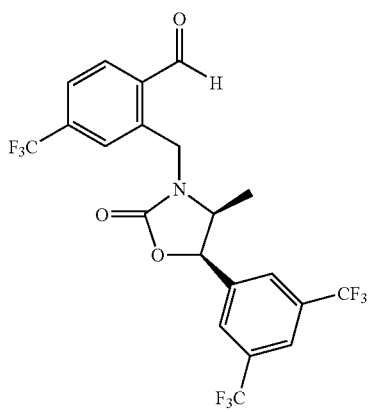

2-({(4S,5R)-5-[3,5-bis(trifluoromethyl)phenyl]-4-methyl-2-oxo-1,3-oxazolidin-3-yl}methyl)-4-(trifluoromethylbenzaldehyde Step A: 2-({(4S,5R)-5-[3,5-bis(trifluoromethyl)phenyl]-4-methyl-2-oxo-1,3-oxazolidin-3-yl}methyl)-4-(trifluoromethyl)benzonitrile To a solution of (4S,5R)-5-[3,5-bis(trifluoromethyl)phenyl]-3-[2-iodo-5-(trifluoromethyl)benzyl]-4-methyl-1,3-oxazolidin-2-one (500 mg, 0.837 mmol) in DMF (7.5 mL) was added CuCN (150 mg, 1.67 mmol). The reaction was heated to 100° C. and stirred at that temperature for 14 hours. The reaction was then cooled to room temperature, diluted with EtOAc (200 mL), and washed with 100 mL of 2.5 M aqueous ammonia. The organic layer was washed with brine (75 mL) and then filtered through a plug of silica gel. The filtrate was concentrated, and the residue was purified by flash chromatography on silica gel (5 to 50% EtOAc/hexanes) to afford 2-({(4S,5R)-5-[3,5-bis(trifluoromethyl)phenyl]-4-methyl-2-oxo-1,3-oxazolidin-3-yl}methyl)-4-(trifluoromethyl)benzonitrile. R$_f$=0.29 (25% EtOAc/hexanes). LCMS=497.0 (M+1)$^+$. $^1$H NMR (CDCl$_3$, 500 MHz) δ 7.91 (s, 1H), 7.88 (s, 1H), 7.86 (d, J=8.2 Hz, 1H), 7.79 (s, 2H), 7.74 (d, J=8.2 Hz, 1H), 5.78 (d, J=7.8 Hz, 1H), 4.93 (d, J=16.1 Hz, 1H), 4.53 (d, J=15.8 Hz, 1H), 4.23 (m, 1H), 0.86 (d, J=6.7 Hz, 3H).

Step B: 2-({(4S,5R)-5-[3,5-bis(trifluoromethyl)phenyl]-4-methyl-2-oxo-1,3-oxazolidin-3-yl}methyl-4-(trifluoromethyl)benzaldehyde To a solution of 2-({(4S,5R)-5-[3,5-bis(trifluoromethyl)phenyl]-4-methyl-2-oxo-1,3-oxazolidin-3-yl}methyl)-4-(trifluoromethyl)benzonitrile (242.1 mg, 0.488 mmol) in 88% aqueous formic acid (5.86 mL) was added PtO$_2$ (57 mg, 0.251 mmol). The reaction was heated to 60° C. After 2 hours, additional PtO$_2$ (57 mg, 0.251 mmol) was added. After 2 more hours, a third portion of PtO$_2$ (57 mg, 0.251 mmol) was added. Heating of the reaction at 60° C. was continued for 18 more hours, and then the reaction was cooled to room temperature. The catalyst was removed by filtration through celite with THF (50 mL). The filtrate was diluted with EtOAc (100 mL) and washed with H$_2$O (2×50 mL), 1:1 saturated NaHCO$_3$/brine (2×50 mL), and brine (50 mL). The organic layer was dried over Na$_2$SO$_4$, filtered, and concentrated. Purification of the residue by flash chromatography (5 to 35% EtOAc/hexanes) afforded 2-({(4S,5R)-5-[3,5-bis(trifluoromethyl)phenyl]-4-methyl-2-oxo-1,3-oxazolidin-3-yl}methyl)-4-(trifluoromethyl)benzaldehyde. R$_f$=0.23 (25% EtOAc/hexanes). LCMS=500.0 (M+1)$^+$. $^1$H NMR (CDCl3, 500 MHz) δ 10.26 (s, 1H), 7.79-8.02 (m, 6H), 5.74 (d, J=8.1 Hz, 1H), 5.08 (d, J=16.5 Hz, 1H), 4.91 (d, J=16.7 Hz, 1H), 4.18 (m, 1H), 0.81 (d, J=6.4 Hz, 3H).

Intermediate 3

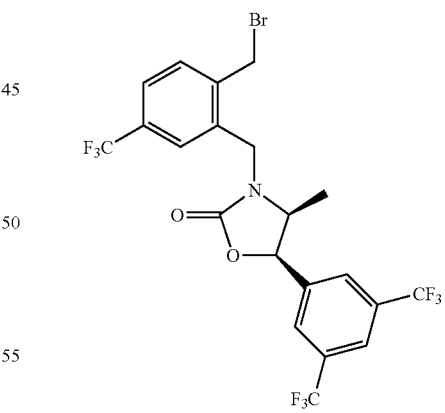

(4S,5R)-5-[3,5-bis(trifluoromethyl)phenyl]-3-[2-(bromomethyl)-5-(trifluoromethyl)benzyl]-4-methyl-1,3-oxazolidin-2-one.

Step A: (4S,5R)-5-[3,5-bis(trifluoromethyl)phenyl]-3-[2-(hydroxymethyl)-5-(trifluoromethyl)benzyl]-4-methyl-1,3-oxazolidin-2-one To a 0° C. solution of 2-({(4S,5R)-5-[3,5-bis(trifluoromethyl)phenyl]-4-methyl-2-oxo-1,3-oxazolidin-3-yl}methyl)-

4-(trifluoromethyl)benzaldehyde (99.3 mg, 0.199 mmol) in MeOH (5 mL) was added excess NaBH$_4$. The reaction was stirred for 30 minutes, and then quenched with saturated NH$_4$Cl solution (10 mL), diluted with EtOAc (60 mL), and washed with brine (25 mL). The organic layer was dried over Na$_2$SO$_4$, filtered, and concentrated. Purification of the residue by flash chromatography on silica gel (10 to 50% EtOAc/hexanes) afforded (4S,5R)-5-[3,5-bis(trifluoromethyl)phenyl]-3-[2-(hydroxymethyl)-5-(trifluoromethyl)benzyl]-4-methyl-1,3-oxazolidin-2-one. R$_f$=0.54 (75% EtOAc/hexanes). LCMS=502.1 (M+1)$^+$. $^1$H NMR (CDCl$_3$, 500 MHz) δ 7.87 (s, 1H), 7.75 (s, 2H), 7.62 (s, 2H), 7.51 (s, 1H), 5.79 (d, J=8.0 Hz, 1H), 5.06 (d, J=15.5 Hz, 1H), 4.83 (d, J=5.1 Hz, 2H), 4.25 (d, J=15.6 Hz, 1H), 4.01-3.99 (m, 1H), 0.79 (d, J=6.6 Hz, 3H).

Step B: (4S,5R)-5-[3,5-bis(trifluoromethyl)phenyl]-3-[2-(bromomethyl)-5-trifluoromethyl)benzyl]-4-methyl-1,3-oxazolidin-2-one To a 0° C. solution of (4S,5R)-5-[3,5-bis(trifluoromethyl)phenyl]-3-[2-(hydroxymethyl)-5-(trifluoromethyl)benzyl]-4-methyl-1,3-oxazolidin-2-one (210 mg, 0.419 mmol) in CH$_2$Cl$_2$ (4 mL) was added CBr$_4$ (292 mg, 0.880 mmol) and a solution of PPh$_3$ (220 mg, 0.838 mmol) in CH$_2$Cl$_2$ (4 mL). The mixture was allowed to warm to room temperature, and, after 90 minutes had elapsed, it was concentrated on to silica gel. Purification of the residue by flash chromatography on silica gel (10 to 50% EtOAc/hexanes) afforded (4S,5R)-5-[3,5-bis(trifluoromethyl)phenyl]-3-[2-(bromomethyl)-5-(trifluoromethyl)benzyl]-4-methyl-1,3-oxazolidin-2-one. R$_f$=0.10 (50% EtOAc/hexanes). LCMS=564.0 (M+1)$^+$. $^1$H NMR (CDCl$_3$, 500 MHz) δ 7.88 (s, 1H), 7.78 (s, 2H), 7.63-7.57 (m, 2H), 7.52 (s, 1H), 5.79 (d, J=8.0 Hz, 1H), 5.09 (d, J=15.8 Hz, 1H), 4.61 (dd, J=13.8, 10.5 Hz, 2H), 4.27 (d, J=15.8 Hz, 1H), 4.06-1.00 (m, 1H), 0.82 (d, J=6.4 Hz, 3H).

Intermediate 4

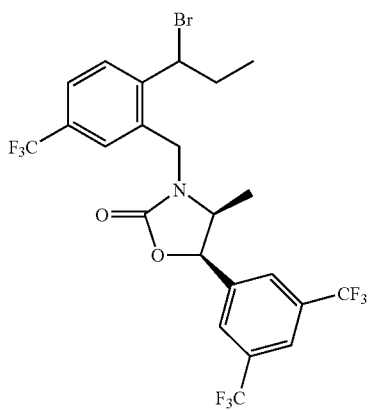

(4S,5R)-5-[3,5-bis(trifluoromethyl)phenyl]-3-[2-(1-bromopropyl)-5-(trifluoromethyl)benzyl]-4-methyl-1,3-oxazolidin-2-one Step A: (4S,5R)-5-[3,5-bis(trifluoromethyl)phenyl]-3-[2-(1-hydroxypropyl)-5-(trifluoromethyl)benzyl]-4-methyl-1,3-oxazolidin-2-one To a −78° C. solution of 2-({(4S,5R)-5-[3,5-bis(trifluoromethyl)phenyl]-4-methyl-2-oxo-1,3-oxazolidin-3-yl}methyl)-4-(trifluoromethyl)benzaldehyde (230 mg, 0.461 mmol) in diethyl ether (5 mL) was added a solution of EtMgBr (230 µL, 0.691 mmol). The solution was stirred for 5 minutes, followed by a second addition of EtMgBr solution (230 µL, 0.691 mmol). After 5 minutes, the reaction was quenched with saturated NH$_4$Cl solution (5 mL), diluted with EtOAc (60 mL), and washed with brine (30 mL). The organic layer was dried over Na$_2$SO$_4$, filtered, and concentrated. Purification of the residue by flash chromatography on silica gel (10 to 35% EtOAc/hexanes) afforded (4S,5R)-5-[3,5-bis(trifluoromethyl)phenyl]-3-[2-(1-hydroxypropyl)-5-(trifluoromethyl)benzyl]-4-methyl-1,3-oxazolidin-2-one. R$_f$=0.14 (25% EtOAc/hexanes). LCMS=512.1 (M+1−18)$^+$. $^1$H NMR (CDCl$_3$, 500 MHz, diastereomers present) δ 7.89-7.45 (m, 6H), 5.69-6.65 (m, 1H), 5.04-4.91 (m, 1H), 4.27-4.18 (m, 1H), 4.03-3.93 (m, 1H), 2.87 (m, 1H), 1.89-1.66 (m, 2H), 1.00-0.93 (m, 3H), 0.79-0.75 (m, 3H).

Step B: (4S,5R)-5-[3,5-bis(trifluoromethyl)phenyl]-3-[2-(1-bromopropyl)-5-(trifluoromethyl)benzyl]-4-methyl-1,3-oxazolidin-2-one To a 0° C. solution of (4S,5R)-5-[3,5-bis(trifluoromethyl)phenyl]-3-[2-(1-hydroxypropyl)-5-(trifluoromethyl)benzyl]-4-methyl-1,3-oxazolidin-2-one (212.4 mg, 0.402 mmol) in CH$_2$Cl$_2$ (5 mL) was added CBr$_4$ (333 mg, 1.00 mmol) and a solution of PPh$_3$ (250 mg, 0.956 mmol) in CH$_2$Cl$_2$ (5 mL). The reaction was allowed to warm to room temperature. After 72 hours, the reaction was concentrated and purified by flash chromatography (10 to 50% EtOAc/hexanes) to afford (4S,5R)-5-[3,5-bis(trifluoromethyl)phenyl]-3-[2-(1-bromopropyl)-5-(trifluoromethyl)benzyl]-4-methyl-1,3-oxazolidin-2-one. LCMS=594.1 (M+1)$^+$. $^1$H NMR (CDCl$_3$, 500 MHz) δ 7.89-7.46 (m, 6H), 5.81-5.69 (m, 1H), 5.25-4.97 (m, 2H), 4.36-3.83 (m, 2H), 2.46-2.34 (m, 1H), 2.25-2.14 (m, 1H), 1.29-1.01 (m, 3H), 0.83-0.78 (m, 3H).

Intermediate 5

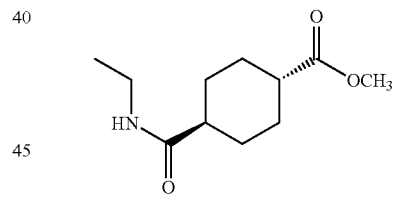

methyl trans-4-[(ethylamino)carbonyl]cyclohexanecarboxylate

A stirred and cooled (0° C.) solution of trans-4-(methoxycarbonyl)cyclohexanecarboxylic acid (0.500 g, 2.69 mmol) in CH$_2$Cl$_2$ (10 mL) was treated dropwise with a solution of oxalyl chloride (2.0 M in CH$_2$Cl$_2$ 1.58 mL, 3.15 mmol) and one drop of DMF, under an atmosphere of nitrogen. The reaction was stirred for 20 min at 0° C., allowed to warm to room temperature and stirred for an additional 2 h. The product was placed under high vacuo for 20 min, dissolved in THF (15 mL) and treated with diethylamine (2.0 M solution in THF, 1.37 mL, 2.73 mmol) and triethylamine (380 uL, 2.73 mmol). The reaction was stirred at room temperature for an additional 18 h. Saturated NH$_4$Cl (1 mL) was added and the resultant mixture was partitioned between H$_2$O (20 mL) and EtOAC (20 mL). The aqueous layer was re-extracted with EtOAc (3×20 mL) and the combined extracts were washed with brine (40 mL), dried (Na$_2$SO$_4$), filtered and concentrated in vacuo. The residue was purified by flash silica gel chromatography (0-25% EtOAc/hexanes gradient) to afford methyl trans-4-[(ethylamino)carbonyl]cyclohexanecarboxylate as a colorless oil. LCMS=214.2 (M+1)$^+$.

Intermediate 6

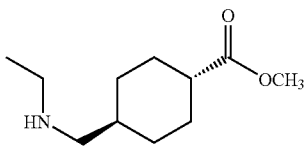

methyl trans-4-[(ethylamino)methyl]cyclohexanecarboxylate

A stirred suspension of methyl trans-4-[(ethylamino)carbonyl]cyclohexanecarboxylate (Intermediate 5, 430 mg, 2.01 mmol) and NaBH$_4$ in THF (10 mL) was treated with acetic acid (1.6 mL) and heated at reflux for 16 h an atmosphere of N$_2$. The reaction was cooled to room temperature, quenched with H$_2$O (1 mL) and diluted with 1N NaOH (15 mL). The mixture was extracted with EtOAc (3×40 mL) and the combined extracts were washed with brine (40 mL), dried (MgSO$_4$), filtered and concentrated in vacuo. The residue was purified by flash silica gel chromatography (0-25% EtOAc/hexanes gradient) to afford methyl trans-4-[(ethylamino)methyl]cyclohexanecarboxylate as a clear oil. LCMS=200.2 (M+)$^+$. $^1$H NMR (CDCl$_3$, 500 MHz): δ 3.67 (s, 3H), 2.67-2.64 (q, J=7.1 Hz, 2H), 2.49-2.46 (m, 2H), 2.28-2.24 (m, 1H), 2.16-1.86 (m, 4H), 1.49-1.41 (m, 2H), 1.12 (t, J=5.5 Hz, 3H), 1.03 (m, 2H).

Intermediate 7

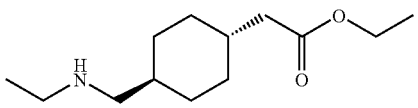

ethyl{trans-4-[(ethylamino)methyl]cyclohexyl}acetate

Step A: ethyl{trans-4-[(ethylamino)carbonyl]cyclohexyl}acetate

To a stirred solution of trans-4-(2-ethoxy-2-oxoethyl)-cyclohexanecarboxylic acid (Intermediate 6; 800 mg; 3.74 mmol) in CH$_2$Cl$_2$ (5 mL) was added oxalyl chloride (4.7 mL; 9.35 mmol), followed by a drop of DMF. After 3 h, the reaction was concentrated in vacuo, redissolved in THF (4 mL) and added dropwise to a stirred solution of ethylamine (2.0 M; 1.87 mL; 3.74 mmol) in THF (4 mL) at 0° C. Triethylamine (521 mL; 3.74 mmol) was added and the reaction stirred at 0° C. for 1 h. The reaction was quenched with H$_2$O (25 mL) and extracted with EtOAc (3×50 mL). The combined extracted were washed with H$_2$O and brine (25 mL each), dried (Na$_2$SO$_4$), filtered and concentrated in vacuo. The residue was purified by flash silica gel chromatography (0-75% EtOAc/hexanes gradient) to afford ethyl{trans-4-[(ethylamino)carbonyl]cyclohexyl}acetate as a white solid. LCMS=242.2 (M+1)$^+$. $^1$H NMR (CDCl$_3$, 500 MHz): δ 5.40 (s, 1H), 4.14 (q, J=7.1 Hz, 2H), 3.33-3.28 (m, 2H), 2.21 (d, J=7.1 Hz, 2H), 2.02 (tt, J=12.2, 3.4 Hz, 1H), 1.94-1.78 (m, 5 H), 1.51 (qd, J=12.9, 3.2 Hz, 2H), 1.27 (t, J=7.1 Hz, 3H), 1.15 (t, J=7.3 Hz, 3H), 1.07 (qd, J=12.8, 3.2 hz, 2H).

Step B: ethyl{trans-4-[(ethylamino)methyl]cyclohexyl}acetate

A stirred suspension of ethyl{trans-4-[(ethylamino)carbonyl]cyclohexyl}acetate (Step A; 740 mg; 3.07 mmol) and sodium borohydride (558 mg; 14.74 mmol) in THF (6 mL) was heated at reflux. Acetic acid (845 mL) was added dropwise over 1 h and the resultant mixture was heated at reflux for 2 h more. The reaction was cooled in an ice bath and carefully quenched with H$_2$O (1.5 mL). 1.5N NaOH (10 mL) was added and the reaction was extracted with EtOAc (3×50 mL). The combined extracts were washed with H$_2$O and brine (25 mL each), dried (Na$_2$SO$_4$), filtered and concentrated in vacuo. The residue was redissolved in EtOH (4 mL) and 4N HCl (EtOAc) (0.9 mL) was added dropwise. The reaction stirred at room temperature for 14 h. The reaction was diluted with EtOAc (30 mL) and washed successively with 2N NaOH, H$_2$O, and brine (15 mL each). The aqueous layers were re-extracted with EtOAc (2×25 mL) and the extracts were washed with brine (15 mL). The combined organic layers were dried (Na$_2$SO$_4$), filtered and concentrated in vacuo to afford ethyl{trans-4-[(ethylamino)methyl]cyclohexyl}acetate as a yellow oil. LCMS=228.3 (M+1)$^+$. $^1$H NMR (CDCl$_3$, 500 MHz): δ 4.14 (q, J=7.1 Hz, 2H), 2.66 (q, J=7.2 Hz, 2H), 2.47 (d, J=6.9 Hz, 2H), 2.19 (d, J=6.8 Hz, 2 H), 1.83-1.78 (m, 4H), 1.59-1.52 (m, 2H), 1.44-1.36 (m, 2H), 1.27 (t, J=7.1 Hz, 3H), 1.13 (t, J=7.2 Hz, 3H), 1.03-0.97 (m, 2 H).

Intermediate 8

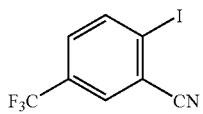

2-Iodo-5-(trifluoromethyl)benzonitrile

To a solution of 2-amino-5-(trifluoromethyl)benzonitrile (15.1 g) and diiodomethane (24 mL) in acetonitrile (150 mL) at 35° C. was added t-butyl nitrite (21 mL) dropwise. The reaction was maintained at approximately 35° C. during the addition. The reaction was aged for 30 min and then heated to 60° C. for 30 minutes. The reaction mixture was cooled, diluted with ether and washed twice with water, twice with aqueous sodium bisulfite, water and then brine. The solution was dried over anhydrous MgSO$_4$, filtered through a silica gel plug and then concentrated giving afford a red oil. The product was purified by silica gel chromatography eluting sequentially with hexanes, 3:1 hexanes/CH$_2$Cl$_2$ and 1:1 hexanes/CH$_2$Cl$_2$ to afford 2-iodo-5-(trifluoromethyl)benzonitrile. $^1$H NMR (CDCl$_3$, 500 MHz) δ 8.10 (d, J=8.5 Hz, 1H), 7.85 (d, J=1.8 Hz, 1H), 7.52 (dd, J=8.5, 1.8 Hz, 1H).

Intermediate 9

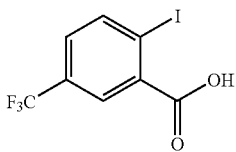

2-Iodo-5-(trifluoromethyl)benzoic acid

Potassium hydroxide (3.78 g; 0.0673 mol) was added to a stirred solution of 2-iodo-5-(trifluoromethyl)benzonitrile (Intermediate 8; 4 g; 0.0135 mol) in a 1:1 isopropanol:$H_2O$ solution (60 mL). The reaction was heated at reflux for 14 h and then partitioned between $H_2O$ (50 mL) and EtOAc (50 mL). The aqueous layer was extracted with EtOAc (50 mL) and acidified to pH 5 with 6N HCl. The aqueous layer was further extracted with EtOAc (4×50 mL) and the combined extracts were washed with brine (50 mL), dried over $MgSO_4$, filtered, and concentrated in vacuo to afford 2-iodo-5-(trifluoromethyl)benzoic acid as a yellow solid. LCMS=317.0 $(M+1)^+$. $^1H$ NMR ($CDCl_3$, 500 MHz): δ 8.27 (d, J=1.6 Hz, 1 H), 8.25 (d, J=8.2 Hz, 1 H), 7.47 (dd, J=8.2, 1.8 Hz, 1 H).

Intermediate 10

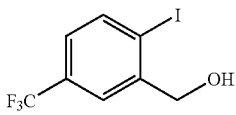

[2-Iodo-5-(trifluoromethyl)phenyl]methanol

Borane-THF (11.0M solution in THF; 94 mL; 94 mmol) was added to a stirred solution of 2-iodo-5-(trifluoromethyl) benzoic acid (Intermediate 9, 2.97 g; 9.4 mmol) in THF (300 mL) at 0° C. under $N_2$. The reaction was heated at reflux for 90 min and then carefully quenched with 6N HCl until no further gas evolution. The reaction was diluted with $H_2O$ (250 mL) and extracted with EtOAc (3×250 mL). The combined extracts were washed with brine (300 mL), dried over $MgSO_4$, filtered, and concentrated in vacuo. The crude material was purified by flash chromatography on silica gel (0-25% EtOAc/hexanes gradient) to afford [2-iodo-5-(trifluoromethyl)phenyl]methanol as a white solid. LCMS=285.0 $(M-17)^+$. $^1H$ NMR ($CDCl_3$, 500 MHz): δ 7.97 (d, J=8.3 Hz, 1 H), 7.79 (s, 1 H), 7.28 (d, J=8.4 Hz, 1 H), 4.75 (s, 2 H).

Intermediate 11

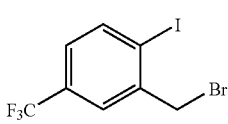

2-(Bromomethyl)-1-iodo-4-(trifluoromethyl)benzene

Carbon tetrabromide (1.86 g; 5.6 mmol) and triphenylphosphine (1.47 g; 5.6 mmol) were added successively to a stirred solution of [2-iodo-5-(trifluoromethyl)phenyl] methanol (Intermediate 10, 1.13 g; 3.74 mmol) in $CH_2Cl_2$ (25 mL) at 0° C. under $N_2$. The reaction was stirred at room temperature for 48 h. A second equivalent of carbon tetrabromide (1.2 g; 3.74 mmol) and triphenylphosphine (0.98 g; 3.74 mmol) was added and the reaction was stirred an additional 14 h. The solvent was removed in vacuo and the residue was purified by flash chromatography on silica gel (0-25% EtOAc/hexanes gradient) to afford 2-(bromomethyl)-1-iodo-4-(trifluoromethyl)benzene as a clear oil. $^1H$ NMR ($CDCl_3$, 500 MHz): δ 8.02 (d, J=8.2 Hz, 1 H), 7.73 (d, J=1.8 Hz, 1 H), 7.26 (dd, J=8.3, 1.8 Hz, 1 H), 4.64 (s, 2 H).

Intermediate 12

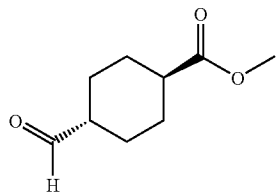

methyl trans-4-formylcyclohexanecarboxylate

To a flask containing methyl trans-4-(hydroxymethyl)cyclohexanecarboxylate (100 mg, 0.581 mmol) in $CH_2Cl_2$ (5.8 mL) at 0° C., was added Dess-Martin periodinane (493 mg, 1.16 mmol). The reaction was allowed to warm to room temperature over an hour and then was diluted with EtOAc (60 mL), washed with saturated $K_2CO_3$ solution (3×40 mL) and brine (40 mL). The organic layer was dried over $Na_2SO_4$, filtered, and concentrated. Purification of the residue by flash chromatography on silica gel (0 to 25% EtOAc/hexanes) afforded methyl trans-4-formylcyclohexanecarboxylate. $R_f$=0.87 (25% EtOAc/hexanes). $^1H$ NMR ($CDCl_3$, 500 MHz) δ 9.63 (s, 1H), 3.67 (s, 3H), 2.51-2.05 (m, 6H), 1.63-1.26 (m, 4H).

Intermediate 13

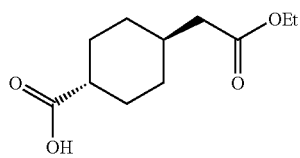

trans-4-(2-ethoxy-2-oxoethyl)cyclohexanecarboxylic acid

Step A: 4-(2-ethoxy-2-oxoethyl)cyclohexanecarboxylic acid

A three liter round bottom flask was charged with ethyl (4-oxocyclohexyl)acetate (100 g, 0.588 mol) and ethanol (400 mL). Sodium hydroxide (25.8 g, 0.645 mol) was added, and the reaction was stirred at room temperature for 1 hour. Next, triethyl phosphonoacetate (128 mL, 0.645 mol) was added, and the reaction was then cooled to 0° C. A solution of NaOEt in EtOH (21% solution, 242 mL) was added dropwise to the reaction over 1 hour. The reaction was warmed to room temperature and stirred for 1 hour. HOAc (84 mL) was added, followed by ammonium formate (74 g) and 5% Pd/C (10 g). The reaction was heated to 60° C. for 6 hours and then cooled to room temperature. The solids were filtered off and the filtrate was concentrated. The residue was taken up in EtOAc (2 L) and washed with 1N HCl (2×500 mL), H$_2$O (500 mL), and brine (500 mL). The organic layer was concentrated to an oil and azeotroped with toluene (2 L). The residue was purified by flash chromatography on silica gel (0 to 50% EtOAc/Hexanes containing 1% HOAc). This afforded 4-(2-ethoxy-2-oxoethyl)cyclohexanecarboxylic acid as a mixture of cis and trans isomers.

Step B: benzyl trans-4-(2-ethoxy-2-oxoethyl)cyclohexanecarboxylate 96 g (0.448 mol) of 4-(2-ethoxy-2-oxoethyl)cyclohexanecarboxylic acid (mixture of cis and trans isomers) was dissolved in CH$_2$Cl$_2$ (1 L). To this solution, oxalyl chloride (76 mL, 0.885 mol) was added dropwise. The reaction was stirred at room temperature for 2 hours and then concentrated. CH$_2$Cl$_2$ (1 L) was added to the residue and the solvent was stripped off. The process was repeated. Next, the residue was dissolved in CH$_2$Cl$_2$ (1 L) and Et$_3$N (94 mL, 0.672 mol) was added. The solution was cooled to 10° C. and benzyl alcohol (56 mL, 0.537 mol) was added dropwise. The reaction was allowed to warm to room temperature and stir at room temperature for 12 hours. Next, the solvent was removed and toluene (1 L) was added. The volume of solvent was reduced to 500 mL and the solids were removed by filtration. The filtrate was concentrated and the residue was purified by flash chromatography on silica gel (0 to 20% EtOAc/heptanes) to afford benzyl trans-4-(2-ethoxy-2-oxoethyl)cyclohexanecarboxylate.

Step C: trans-4-(2-ethoxy-2-oxoethyl)cyclohexanecarboxylic acid

To a solution of benzyl trans-4-(2-ethoxy-2-oxoethyl)cyclohexanecarboxylate (52.4 g, 0.172 mol) in MeOH (500 mL) was added 10% Pd/C (5 g). The reaction was hydrogenated at 40 psi for 1 hour and then the catalyst was removed by filtration. The filtrate was concentrated to afford trans-4-(2-ethoxy-2-oxoethyl)cyclohexanecarboxylic acid. $^1$H NMR (CDCl$_3$, 500 MHz) δ 4.12 (q, J=7.1 Hz, 2H), 2.24 (m, 1H), 2.19 (d, J=7.1 Hz, 2H), 1.98-2.04 (m, 2H), 1.81-1.87 (m, 2H), 1.77 (m, 1H), 1.46 (qd, J=13.0, 3.4 Hz, 2H), 1.24 (t, J=7.1 Hz, 3H), 1.02 (qd, J=13.0, 3.4 Hz, 2H).

Intermediate 14

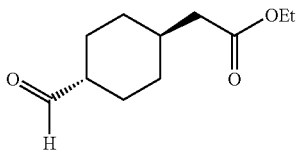

ethyl (trans-4-formylcyclohexyl)acetate

Step A: ethyl [trans-4-(hydroxymethyl)cyclohexyl]acetate

To a solution of trans-4-(2-ethoxy-2-oxoethyl)cyclohexanecarboxylic acid (385.6 mg, 1.80 mmol) in THF (20 mL) was added BH$_3$ (2.7 mL of a 1M solution in THF, 2.70 mmol). After 2 hours, the reaction was quenched by careful addition of H$_2$O (10 mL). The mixture was extracted with EtOAc (80 mL) and the organic layer was washed with water and brine (20 mL each). The organic layer was dried over Na$_2$SO$_4$, filtered, and concentrated. Purification of the residue by flash chromatography on silica gel (5 to 60% EtOAc/hexanes) afforded ethyl [trans-4-(hydroxymethyl)cyclohexyl]acetate. R$_f$=0.26 (40% EtOAc/hexanes). $^1$H NMR (CDCl$_3$, 600 MHz) δ 4.12 (q, J=7.1 Hz, 2H), 3.45 (d, J=6.5 Hz, 2H), 2.19 (d, J=7.0 Hz, 2H), 1.72-1.82 (m, 5H), 1.45 (m, 1H), 1.25 (t, J=7.1 Hz, 3H), 0.96-1.05 (m, 4H).

Step B: ethyl (trans-4-formylcyclohexyl)acetate

To a 0° C. solution of ethyl [trans-4-(hydroxymethyl)cyclohexyl]acetate (102.8 mg, 0.514 mmol) in CH$_2$Cl$_2$ (6 n-L) was added Dess-Martin periodinane. The reaction was warmed to room temperature and stirred for several hours. The reaction was then diluted with EtOAc (50 mL) and washed with 1N NaOH and brine (15 mL each). The organic layer was dried over Na$_2$SO$_4$, filtered, and concentrated. Purification of the residue by flash chromatography on silica gel (5 to 25% EtOAc/hexanes) afforded ethyl (trans-4-formylcyclohexyl)acetate. R$_f$=0.57 (40% EtOAc/hexanes). $^1$H NMR (CDCl$_3$, 500 MHz) δ 9.61 (d, J=1.4 Hz, 1H), 4.13 (q, J=7.1 Hz, 2H), 2.13-2.22 (m, 3H), 1.98-2.01 (m, 2H), 1.87-1.91 (m, 2H), 1.77 (m, 1H), 1.31 (qd, J=13.0, 3.4 Hz, 2H), 1.25 (t, J=7.1 Hz, 3H), 1.05 (qd, J=13.0, 3.4 Hz, 2H).

Intermediate 15

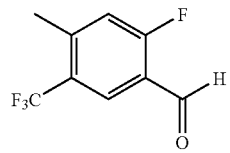

2-fluoro-4-methyl-5-(trifluoromethyl)benzaldehyde

To a −78° C. flask containing THF (7 mL) was added s-BuLi (10 mL of a 1.4 M solution in cyclohexane, 14.0 mmol). To this −78° C. solution was added a solution of 4-fluoro-2-methyl-1-(trifluoromethyl)benzene (2.0 g, 11.23 mmol) in heptanes (7 mL) over 20 minutes. The reaction was stirred at −78° C., for 1 hour and then DMF (1.5 mL) was added. Next, 1N HCl (30 mL) was added, and the reaction was warmed to room temperature and stirred for 10 minutes. The mixture was extracted with hexanes (75 mL) and the organic layer was washed with water and brine (20 mL each). The organic layer was dried over Na$_2$SO$_4$, filtered, and concentrated. Purification of the residue by flash chromatography on silica gel afforded 2-fluoro-4-methyl-5-(trifluoromethyl)benzaldehyde. R$_f$=0.44 (15% EtOAc/hexanes). $^1$H NMR (CDCl$_3$, 500 MHz) δ 10.31 (s, 1H), 8.14 (d, J=6.6 Hz, 1H), 7.13 (d, J=10.5 Hz, 1H), 2.56 (d, J=1.3 Hz, 3H).

Intermediate 16

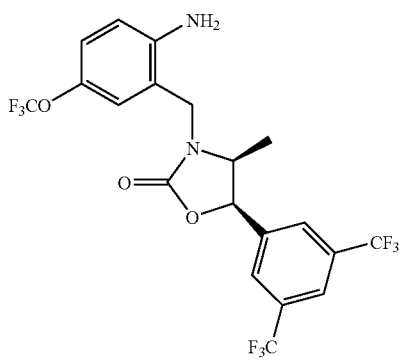

(4S,5R)-3-[2-amino-5-(trifluoromethoxy)benzyl]-5-[3,5-bis(trifluoromethyl)phenyl]-4-methyl-1,3-oxazolidin-2-one

Step A: 2-(bromomethyl)-1-nitro-4-(trifluoromethoxy)benzene

Fuming nitric acid (5 mL) was cooled to 0° C. and 3-(trifluoromethoxy)benzyl bromide (1 mL, 6.16 mmol) was added. After 15 minutes, the reaction was poured into ice water (100 mL) and extracted with EtOAc (200 mL). The organic layer was washed with water, saturated NaHCO$_3$, and brine (75 mL each). The organic layer was dried over Na$_2$SO$_4$, filtered, and concentrated. Purification of the residue by flash chromatography on silica gel (0 to 15% EtOAc/hexanes) afforded 2-(bromomethyl)-1-nitro-4-(trifluoromethoxy)benzene R$_f$=0.54 (15% EtOAc/hexanes). $^1$H NMR (CDCl$_3$, 500 MHz) δ 8.14 (d, J=8.9 Hz, 1H), 7.43 (m, 1H), 7.31 (m, 1H), 4.82 (s, 2H).

Step B: (4S,5R)-5-[3,5-bis(trifluoromethyl)phenyl]-4-methyl-3-[2-nitro-5-(trifluoromethoxy)benzyl]-1,3-oxazolidin-2-one To a solution of (4S,5R)-5-[3,5-bis(trifluoromethyl)phenyl]-4-methyl-1,3-oxazolidin-2-one (840 mg, 2.68 mmol) in DMA (25 mL) was added NaHMDS (2.68 mL of a 1M solution in THF, 2.68 mmol). The reaction was stirred at room temperature for 5 minutes, and then 2-(bromomethyl)-1-nitro-4-(trifluoromethoxy)benzene (967 mg, 3.22 mmol) was added by cannula in DMA (5 mL). After 15 minutes, the reaction was poured into saturated NH$_4$Cl (50 mL). The mixture was extracted with EtOAc (150 mL) and the organic layer was washed with water and brine (40 mL each). The organic layer was dried over Na$_2$SO$_4$, filtered, and concentrated. Purification of the residue by flash chromatography on silica gel (5 to 25% EtOAc/hexanes) afforded (4S,5R)-5-[3,5-bis(trifluoromethyl)phenyl]-4-methyl-3-[2-nitro-5-(trifluoromethoxy)benzyl]-1,3-oxazolidin-2-one. R$_f$=0.10 (15% EtOAc/hexanes). LCMS=533.2 (M+1)$^+$. $^1$H NMR (CDCl$_3$, 500 MHz) δ 8.16 (d, J=8.9 Hz, 1H), 7.92 (s, 1H), 7.80 (s, 2H), 7.44 (s, 1H), 7.33 (d, J=8.9 Hz, 1H), 5.78 (d, J=7.8 Hz, 1H), 4.94 (d, J=17.0 Hz, 1H), 4.79 (d, J=16.9 Hz, 1H), 4.25 (m, 1H), 0.81 (d, J=6.7 Hz, 3H).

Step C: (4S,5R)-3-[2-amino-5-(trifluoromethoxy)benzyl]-5-[3,5-bis(trifluoromethyl)phenyl]-4-methyl-1,3-oxazolidin-2-one To a solution of (4S,5R)-5-[3,5-bis(trifluoromethyl)phenyl]-4-methyl-3-[2-nitro-5-(trifluoromethoxy)benzyl]-1,3-oxazolidin-2-one (1.07 g, 2.01 mmol) in EtOAc (30 mL) was added PtO$_2$ (100 mg, 0.44 mmol). The reaction was placed under a H$_2$ atmosphere (balloon) and stirred vigorously. After 1 hour, the catalyst was removed by filtration, and the filtrate was concentrated. Purification of the residue by flash chromatography (5 to 40% EtOAc/hexanes) afforded (4S,5R)-3-[2-amino-5-(trifluoromethoxy)benzyl]-5-[3,5-bis(trifluoromethyl)phenyl]-4-methyl-1,3-oxazolidin-2-one. R$_f$=0.45 (40% EtOAc/hexanes). LCMS=503.2 (M+1)$^+$. $^1$H NMR (CDCl$_3$, 600 MHz) δ 7.89 (s, 1H), 7.75 (s, 2H), 7.03 (dd, J=8.7, 2.0 Hz, 1H), 6.90 (d, J=2.1 Hz, 1H), 6.67 (d, J=8.7 Hz, 1H), 5.67 (d, J=8.5 Hz, 1H), 4.73 (d, J=15.4 Hz, 1H), 4.35 (bs, 2H), 4.09 (d, J=15.4 Hz, 1H), 4.04 (m, 1H), 0-78 (d, J=6.6 Hz, 3H).

Intermediate 17

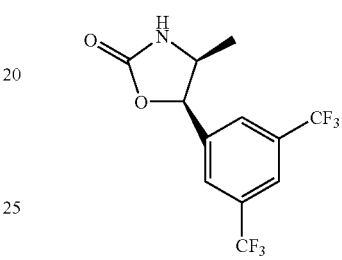

(4S,5R)-5-[3,5-bis(trifluoromethyl)phenyl]4-methyl-1,3-oxazolidin-2-one

Step A. 1-[3,5-Bis(trifluoromethyl)phenyl]-2-nitropropan-1-ol

A stirred solution of 3,5-bis(trifluoromethyl)benzaldehyde (1.00 g, 4.13 mmol) and nitroethane (1.13 g, 1.08 mL, 15.1 mmol) in absolute EtOH (20 mL) at 0° C. was treated with 10% aq. NaOH (m/v) (1.73 mL, 4.34 mmol), stirred for 1 h and treated with 2% aq. acetic acid (m/v) (13.0 mL, 4.32 mmol). The reaction was stirred for 1 h at room temperature then partitioned between water (50 mL) and EtOAc (50 mL). The aqueous layer was extracted with EtOAc (2×50 mL) and the combined organic extracts were washed with saturated NaHCO$_3$ (50 mL) and brine (50 mL), dried (Na$_2$SO$_4$) and concentrated in vacuo to afford a 1.5:1 mixture of threo- and erythro-1-[3,5-bis(trifluoromethyl)phenyl]-2-nitropropan-1-ol as a colorless oil. $^1$H NMR (CDCl$_3$, 500 MHz) threo-diastereoisomer: δ 7.88 (br s, 1H), 7.86 (br s, 2H), 5.22 (d, J=8.4 Hz, 1H), 4.77 (dq, J=8.4, 6.9 Hz, 1H), 3.03 (br s 1H), 1.42 (d, J=6.9 Hz, 3H), erythro-diastereoisomer: δ 7.90 (br s, 1H), 7.86 (br s, 2H), 5.59 (d, J=3.2 Hz, 1H), 4.72 (dq, J=3.2, 6.9 Hz, 1H), 3.03 (br s 1H), 1.50 (d, J=6.9 Hz, 3H).

Step B. 2-Amino-1-[3,5-bis(trifluoromethyl)phenyl]propan-1-ol

A suspension of Raney Nickel (50 mg) in a solution of a 1.5:1 mixture of threo- and erythro-1-[3,5-bis(trifluoromethyl)phenyl]-2-nitropropan-1-ol (50 mg, 0.158 mmol) in 30% (v/v) aqueous HCO2H (0.75 mL) and MeOH (10 mL) was stirred overnight at room temperature under 15 psi of H2. The reaction mixture was filtered through a pad of Celite and the filtrate was concentrated in vacuo to remove the MeOH. The aqueous slurry was adjusted to pH 9-10 with 28% aq NH4OH, diluted with water (20 mL) and extracted with EtOAc (3×20 mL). The combined extracts were washed with brine (10 mL), dried (Na2SO4) and concentrated in vacuo to afford a mixture of threo- and erythro-2-amino-1-[3,5-bis (trifluoromethyl)phenyl]propan-1-ol as colorless solid. LCMS calc.=288.08; found=288.1 (M+1)+. 1H NMR (CDCl₃, 500 MHz) threo-diastereoisomer: δ 7.79 (br s, 3H), 4.35 (br s, 1H), 3.25 (br s, 1H), 2.59 (br s, 3H), 0.86 (d, J=6.1 Hz, 3H), erythro-diastereoisomer: δ 7.79 (br s, 3H), 4.71 (br s, 1H), 3.00 (br s, 1H), 2.59 (br s, 3H), 1.06 (d, J=5.0 Hz, 3H).

Step C. 5-[3,5-Bis(trifluoromethyl)phenyl]-4-methyl-1,3-oxazolidin-2-one

Diisopropylethylamine (106 mg, 142 μL, 0.817 mmol) and triphosgene (20.2 mg, 0.068 mmol) were added successively to a stirred solution of 2-amino-1-(4-methylphenyl)ethanol (39.1 mg, 0.136 mmol) in dry CH2Cl2 (10 mL) at 0° C. under N2. The reaction was stirred at 0° C. for 1 h then concentrated in vacuo to a volume of about 5 mL. The mixture was diluted with water (50 mL) and extracted with EtOAc (3×50 mL). The combined organic extracts were dried (Na₂SO₄) and concentrated in vacuo to give the crude product. This was purified by flash chromatography (Si, 12×160 mm, 0-70% EtOAc in hexanes gradient) to afford threo-5-[3,5-bis(trifluoromethyl)phenyl]-4-methyl-1,3-oxazolidin-2-one (17.5 mg) and erythro-5-[3,5-bis(trifluoromethyl)phenyl]-4-methyl-1,3-oxazolidin-2-one (14.4 mg) as colorless solids. threo-diastereoisomer: R$_f$=0.63 (50% EtOAc/hexanes). LCMS calc.=314.06; found=314.1 (M+1)⁺. ¹H NMR (CDCl₃, 600 MHz) δ 7.90 (br s, 1H), 7.83 (br s, 2H), 6.71 (br s, 1H), 5.17 (d, J=7.0 Hz, 1H), 3.86 (br pentet, J=6.2 Hz, 1H), 1.48 (d, J=6.2 Hz, 1H). This compound was separated into its enantiomers (4R,5R)-5-[3,5-bis(trifluoromethyl)phenyl]-4-methyl-1,3-oxazolidin-2-one and (4S,5S)-5-[3,5-bistrifluoromethyl)phenyl]-4-methyl-1,3-oxazolidin-2-one using chiral HPLC (AS column, 20×250 mm, 20% i—PrOH in heptane). erythro-diastereoisomer: R$_f$=0.38 (50% EtOAc/hexanes). LCMS calc.=314.06; found=314.1 (M+1)⁺. ¹H NMR (CDCl₃, 600 MHz) δ (7.90 (br s, 1H), 7.79 (br s, 2H), 5.83 (d, J=8.0 Hz, 1H), 5.34 (br s, 1H), 4.31 (br pentet, J=7.0 Hz, 1H), 0.84 (d, J=6.6 Hz, 1H). This compound was separated into its two enantiomers (4S,5R)-5-[3,5-bis(trifluoromethyl)phenyl]-4-methyl-1,3-oxazolidin-2-one and (4R,5S)-5-[3,5-bistrifluoromethyl)phenyl]-4-methyl-1,3-oxazolidin-2-one using chiral HPLC (AS column, 20×250 mm, 15% i—PrOH in heptane).

Example 1

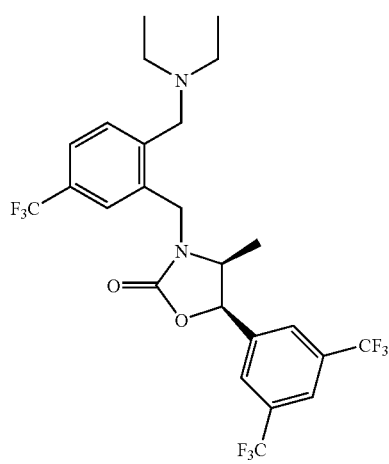

(4S,5R)-5-[3,5-bis(trifluoromethyl)phenyl]-3-[2-[(diethylamino)methyl]-5-(trifluoromethyl)benzyl]-4-methyl-1,3-oxazolidin-2-one To a solution of 2-({(4S,5R)-5-[3,5-bis(trifluoromethyl)phenyl]-4-methyl-2-oxo-1,3-oxazolidin-3-yl}methyl)-4-(trifluoromethyl)benzaldehyde (14.5 mg, 0.0291 mmol) in dichloroethane (300 μL) was added HNEt₂ (4.6 μL, 0.0436 mmol), and NaBH(OAc)₃ (9.2 mg, 0.0436 mmol). The reaction was stirred at room temperature for 18 hours and then diluted with EtOAc (10 mL) and washed with brine (5 mL). The organic layer was dried over Na₂SO₄, filtered, and concentrated. Purification of the residue by PTLC (50% EtOAc/hexanes) afforded (4S,5R)-5-[3,5-bis(trifluoromethyl)phenyl]-3-[2-[(diethylamino)methyl]-5-(trifluoromethyl)benzyl]-4-methyl-1,3-oxazolidin-2-one. R$_f$=0.57 (50% EtOAc/hexanes). LCMS=557.2 (M+1)⁺. ¹H NMR (CDCl₃, 500 MHz) δ 7.92 (s, 1H), 7.82 (s, 2H), 7.55-7.52 (m, 3H), 5.76 (d, J=8.0 Hz, 1H), 5.03 (d, J=16.1 Hz, 1H), 4.60 (d, J=16.1 Hz, 1H), 4.05-4.03 (m, 1H), 3.73 (d, J=13.5 Hz, 1H), 3.57 (d, J=13.7 Hz, 1H), 2.75-2.56 (m, 4H), 1.04 (bs, 6H), 0.80 (d, J=6.4 Hz, 3H).

In a similar manner, the following compounds were synthesized:

| EXAMPLE | MOLECULAR STRUCTURE | LCMS (M + 1)⁺ |
| --- | --- | --- |
| 2 | 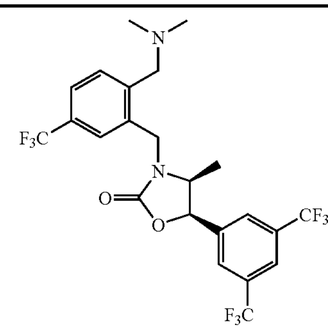 | 529.1 |
| 3 | 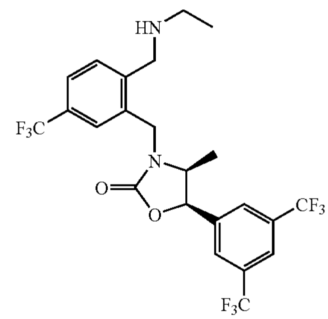 | 529.3 |
| 4 | 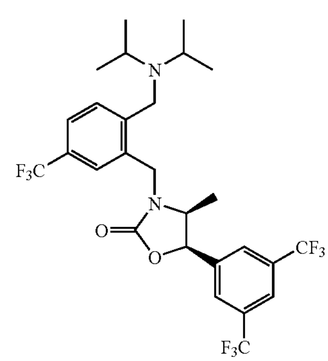 | 585.2 |

-continued

| EXAMPLE | MOLECULAR STRUCTURE | LCMS (M + 1)+ |
|---|---|---|
| 5 | 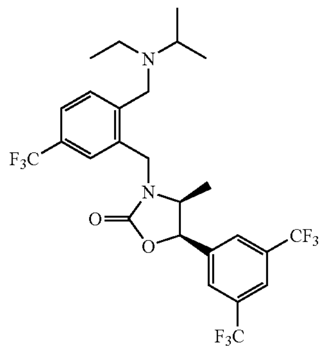 | 571.2 |
| 6 | 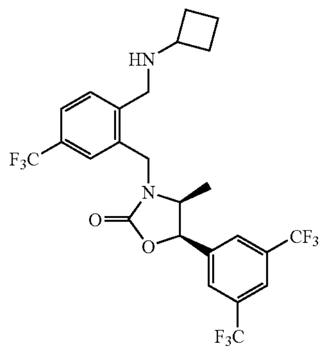 | 555.2 |

Example 7

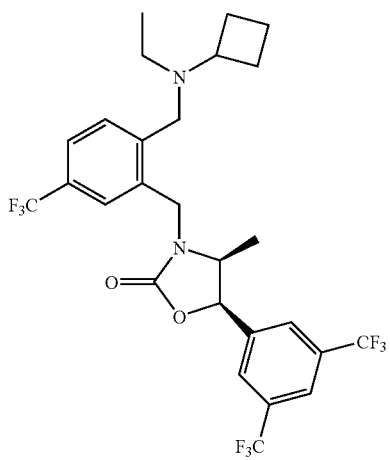

(4S,5R)-5-[3,5-bis(trifluoromethyl)phenyl]-3-[2-{[cyclobutyl(ethyl)amino]methyl}-5-(trifluoromethyl)benzyl]-4-methyl-1,3-oxazolidin-2-one To a solution of (4S,5R)-5-[3,5-bis(trifluoromethyl)phenyl]-3-[2-[(cyclobutylamino)methyl]-5-(trifluoromethyl)benzyl]-4-methyl-1,3-oxazolidin-2-one (3.6 mg, 6.50×10⁻³ mmol) in dichloroethane (300 μL) was added acetaldehyde (40 μL, 0.709 mmol) and NaBH(OAc)₃ (excess). The reaction was stirred at room temperature for 2 hours and then diluted with EtOAc (10 mL) and washed with brine (5 mL). The organic layer was dried over Na$_2$SO$_4$, filtered, and concentrated. Purification of the residue by PTLC (25% EtOAc/hexanes) afforded (4S,5R)-5-[3,5-bis(trifluoromethyl)phenyl]-3-[2-{[cyclobutyl(ethyl)amino]methyl}-5-(trifluoromethyl)benzyl]-4-methyl-1,3-oxazolidin-2-one. R$_f$=0.69 (25% EtOAc/hexanes). LCMS=583.2 (M+1)+. $^1$H NMR (CDCl$_3$, 500 MHz) δ 7.90 (s, 1H), 7.80 (s, 2H), 7.54-7.52 (m, 3H), 5.74 (d, J=8.0 Hz, 1H), 4.99 (d, J=16.1 Hz, 1H), 4.65 (d, J=16.2 Hz, 1H), 4.04-3.98 (m, 1H), 3.64 (d, J=13.9 Hz, 1H), 3.47 (d, J=13.9 Hz, 1H), 3.18-3.12 (m, 1H), 2.48-2.39 (m, 2H), 1.98-1.92 (m, 2H), 1.87-1.74 (m, 2H), 1.67-1.58 (m, 2H), 0.90 (t, J=7.2 Hz, 3H), 0.80 (d, J=6.6 Hz, 3H).

Example 8

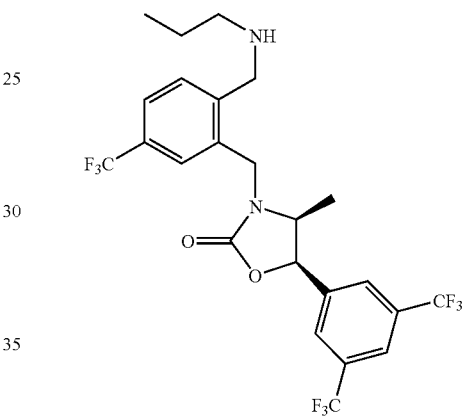

(4S,5R)-5-[3,5-bis(trifluoromethyl)phenyl]-4-methyl-3-[2-[(propylamino)methyl]-5-(trifluoromethyl)benzyl]-1,3-oxazolidin-2-one (TFA salt)

To a solution of (4S,5R)-5-[3,5-bis(trifluoromethyl)phenyl]-3-[2-(bromomethyl)-5-(trifluoromethyl)benzyl]-4-methyl-1,3-oxazolidin-2-one (27 mg, 0.0479 mmol) in MeCN (0.5 mL) was added n—PrNH$_2$.HCl (5.5 mg, 0.0575 mmol) and i—Pr$_2$NEt (20.8 μL, 0.120 mmol). The solution was heated at 80° C. for 16 hours. The reaction was then cooled to room temperature and purified by reverse-phase chromatography (C-18, 10 to 95% MeCN/water with 0.1% TFA). The fractions containing the desired product were lyophilized to afford (4S,5R)-5-[3,5-bis(trifluoromethyl)phenyl]-4-methyl-3-[2-[(propylamino)methyl]-5-(trifluoromethyl)benzyl]-1,3-oxazolidin-2-one (TFA salt). LCMS=543.1 (M+1)+. $^1$H NMR (CDCl$_3$, 500 MHz) δ 9.72 (s, 2H), 7.90 (s, 1H), 7.76 (s, 2H), 7.72 (d, J=6.9 Hz, 1H), 7.56 (d, J=6.4 Hz, 1H), 7.49 (s, 1H), 5.87 (d, J=7.5 Hz, 1H). 4.98 (d, J=15.3 Hz, 1H), 4.35-4.28 (m, 2H), 4.18 (m, 2H), 3.01 (bs, 2H), 1.75-1.60 (m, 2H), 0.96 (m, 3H), 0.90 (d, J=5.5 Hz, 3H).

In a similar manner, the following compounds were synthesized:

| EXAMPLE | MOLECULAR STRUCTURE | LCMS (M + 1)+ |
|---|---|---|
| 9 | 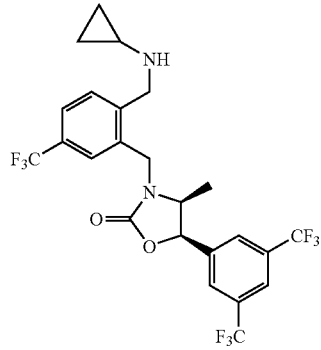 | 541.2 |
| 10 | 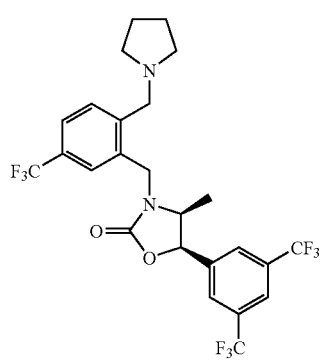 | 555.2 |

Example 11

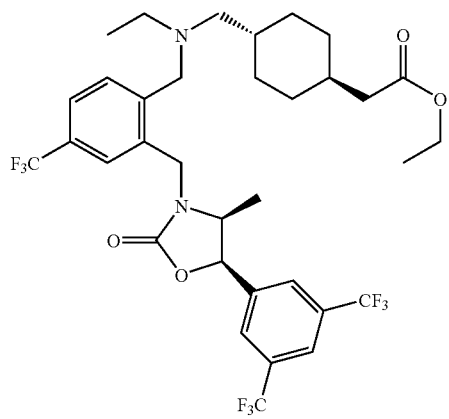

ethyl (trans-4-{[[2-({(4S,5R)-5-[3,5-bis(trifluoromethyl)-phenyl]-4-methyl-2-oxo-1,3-oxazolidin-3-yl}methyl)-4-(trifluoromethyl)benzyl](ethyl)amino]methyl}cyclohexyl)acetate To a solution of (4S,5R)-5-[3,5-bis(trifluoromethyl)phenyl]-3-[2-(bromomethyl)-5-(trifluoromethyl)benzyl]-4-methyl-1,3-oxazolidin-2-one (50.4 mg, 0.0894 mmol) in MeCN (1 mL) was added ethyl trans-4-[(ethylamino)methyl]cyclohexanecarboxylate (20 mg, 0.0894 mmol) and i—Pr₂NEt (240 μL, 0.179 mmol). The reaction was stirred at room temperature for 16 hours and then concentrated. Purification of the residue by PTLC (50% EtOAc/hexanes) afforded ethyl (trans-4-{[[2-({(4S,5R)-5-[3,5-bis(trifluoromethyl)phenyl]-4-methyl-2-oxo-1,3-oxazolidin-3-yl}methyl)-4-(trifluoromethyl)benzyl](ethyl)amino]methyl}cyclohexyl)acetate.

R$_f$=0.42 (50% EtOAc/hexanes). LCMS=711.3 (M+1)+. ¹H NMR (CDCl₃, 500 MHz) δ 7.89 (s, 1H), 7.79 (s, 2H), 7.56-7.52 (m, 2H), 7.48 (s, 1H), 5.73 (d, J=7.8 Hz, 1H), 5.00 (d, J=16.0 Hz, 1H), 4.46 (d, J=16.2 Hz, 1H), 4.11 (q, J=6.9 Hz, 2H), 4.04-3.98 (m, 1H), 3.66-3.53 (m, 2H), 2.47 (q, J=7.1 Hz, 2H), 2.19 (d, J=7.1 Hz, 2H), 2.14 (d, J=7.1 Hz, 2H), 1.80-1.64 (m, 5H), 1.38-1.32 (m, 1H), 1.23 (t, J=7.1 Hz, 3H), 0.99 (t, J=7.1 Hz, 3H), 0.97-0.79 (m, 4H), 0.76 (d, J=6.6 Hz, 3H).

In a similar manner, the following compound was synthesized:

| EXAMPLE | MOLECULAR STRUCTURE | LCMS (M + 1)+ |
|---|---|---|
| 12 | 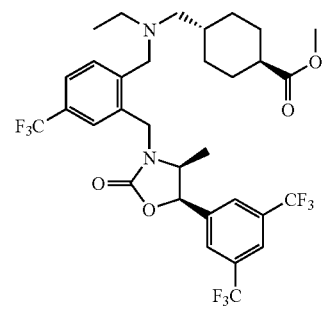 | 683.3 |

Example 13

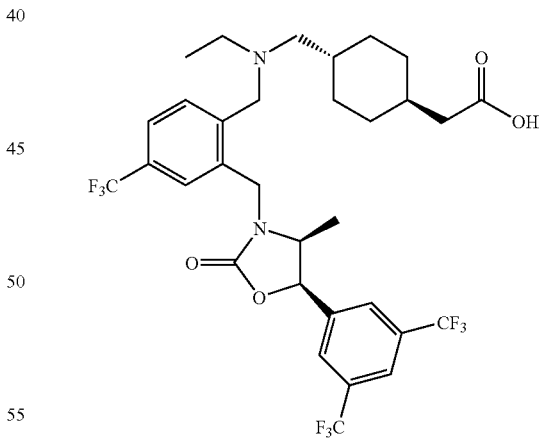

(trans-4-{[[2-({(4S,5R)-5-[3,5-bis(trifluoromethyl)phenyl]-4-methyl-2-oxo-1,3-oxazolidin-3-yl}methyl)-4-(trifluoromethyl)benzyl](ethyl)amino]methyl}cyclohexyl)acetic acid To a solution of ethyl (trans-4-{[[2-({(4S,5R)-5-[3,5-bis(trifluoromethyl)phenyl]-4-methyl-2-oxo-1,3-oxazolidin-3-yl}methyl)-4-(trifluoromethyl)benzyl](ethyl)amino]

methyl}cyclohexyl)acetate (51 mg, 0.0718 mmol) in EtOH (3 mL) and water (2 mL) was added 4 M KOH (500 μL). The mixture was stirred at room temperature for 30 minutes and then water (1 mL) and MeOH (100 μL) were added. After an additional hour, the reaction was quenched with 1 N HCl (5 mL), diluted with EtOAc (20 mL) and washed with brine (10 mL). The organic layer was dried over $Na_2SO_4$, filtered, and concentrated. Purification of the residue by PTLC (50% EtOAc/hexanes with 1% AcOH) was followed by azeotroping of the product with toluene to afford (trans-4-{[[2-({(4S,5R)-5-[3,5-bis(trifluoromethyl)phenyl]-4-methyl-2-oxo-1,3-oxazolidin-3-yl}methyl)-4-(trifluoromethyl)benzyl](ethyl)amino]methyl}cyclohexyl)acetic acid. $R_f$=0.13 (50% EtOAc/hexanes with 1% AcOH). LCMS=683.2 (M+1)$^+$. $^1$H NMR (CDCl$_3$, 500 MHz) δ 7.89 (s, 1H), 7.79 (s, 2H), 7.61-7.53 (m, 2H), 7.48 (s, 1H), 5.74 (d, J=7.8 Hz, 1H), 5.00 (d, J=16.4 Hz, 1H), 4.44 (d, J=16.2 Hz, 1H), 4.04-3.98 (m, 1H), 3.72-3.61 (m, 2H), 2.54-2.53 (m, 2H), 2.23-2.19 (m, 4H), 1.82-1.76 (m, 4H), 1.72-1.64 (m, 1H), 1.39-1.38 (m, 1H), 1.04 (t, J=6.8 Hz, 3H), 0.99-0.78 (m, 4H), 0.76 (d, J=6.8 Hz, 3H).

In a similar manner, the following compounds were synthesized:

Example 16

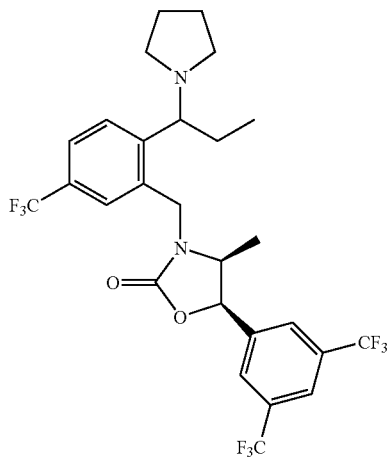

| EXAMPLE | MOLECULAR STRUCTURE | LCMS (M + 1)$^+$ |
|---|---|---|
| 14 | 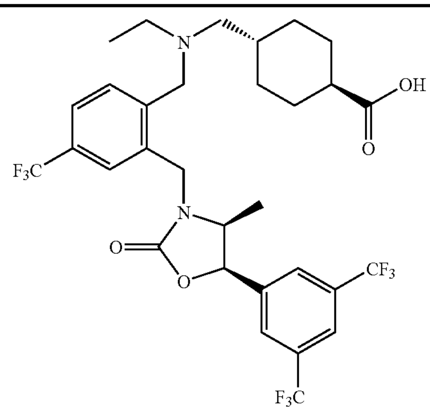 | 669.5 |
| 15 | 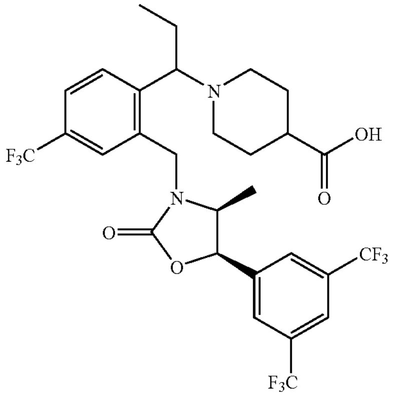 | 641.3 |

(4S,5R)-5-[3,5-bis(trifluoromethyl)phenyl]-4-methyl-3-[2-(1-pyrrolidin-1-ylpropyl)-5-(trifluoromethyl)benzyl]-1,3-oxazolidin-2-one To a solution of (4S,5R)-5-[3,5-bis(trifluoromethyl)phenyl]-3-[2-(1-bromopropyl)-5-(trifluoromethyl)benzyl]-4-methyl-1,3-oxazolidin-2-one (67.1 mg, 0.106 mmol) in MeCN (200 µL) was added pyrrolidine (1 mL, 12.0 mmol). The reaction was stirred at room temperature for 16 hours and then purified by reverse-phase chromatography (C-18, 10 to 95% MeCN/water with 0.1% TFA). The resulting solution was diluted with EtOAc (25 mL), washed with 1 M NaHCO$_3$ (20 mL), extracted with EtOAc (25 mL), and washed with brine (20 mL). The organic layer was dried over Na$_2$SO$_4$, filtered, and concentrated. To the residue was added 200 µL CDCl$_3$, which resulted in a mixture that was diluted with CH$_2$Cl$_2$ (20 mL) and water (5 mL), and washed with 1 M NaOH solution (5 mL). The organic layer was dried over Na$_2$SO$_4$, filtered, and concentrated to afford (4S,5R)-5-[3,5-bis(trifluoromethyl)phenyl]-4-methyl-3-[2-(1-pyrrolidin-1-ylpropyl)-5-(trifluoromethyl)benzyl]-1,3-oxazolidin-2-one. R$_f$=0.14 (25% EtOAc/hexanes). LCMS=583.3 (M+1)$^+$. $^1$H NMR (CDCl$_3$, 500 MHz, diastereomers present) δ 7.94 (s, 1H), 7.84 (s, 2H), 7.67-7.48 (m, 3H), 5.70-5.68 (m, 1H), 5.08-4.96 (m, 1H), 4.64-3.34 (m, 1H), 4.02-3.94 (m, 1H), 3.48-3.39 (m, 1H), 2.54-2.35 (m, 5H), 2.01-1.91 (m, 1H), 1.76-1.72 (m, 4H), 0.79-0.77 (m, 3H), 0.72-0.66 (m, 3H).

This compound, (4S,5R)-5-[3,5-bis(trifluoromethyl)phenyl]-4-methyl-3-[2-(1-pyrrolidin-1-ylpropyl)-5-(trifluoromethyl)benzyl]-1,3-oxazolidin-2-one, was separated into two diastereomers by chiral HPLC (IA column, 2% i—PrOH/heptane).

In a similar manner, the following compounds were synthesized:

| COMPOUND | MOLECULAR STRUCTURE | LCMS (M + 1)$^+$ |
|---|---|---|
| 17 | 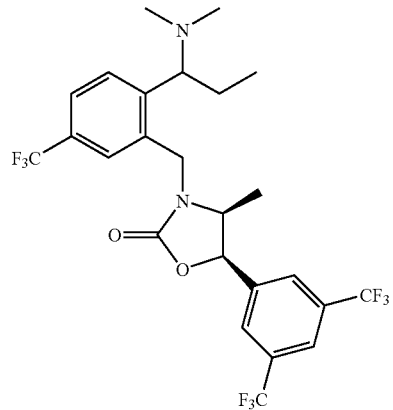 | 557.3 |
| 18 | 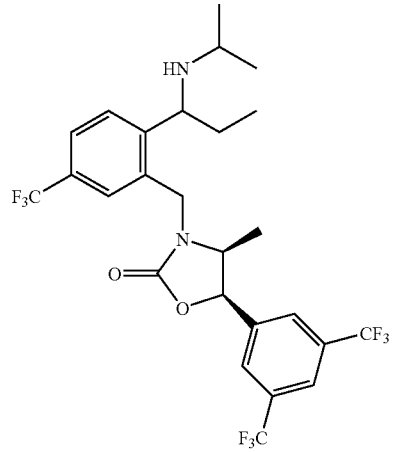 | 571.1 |

| -continued | | |
|---|---|---|
| COMPOUND | MOLECULAR STRUCTURE | LCMS (M + 1)+ |
| 19 | 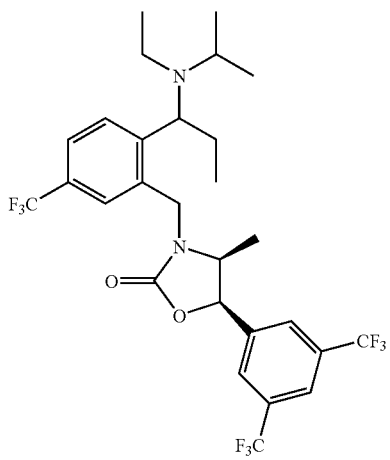 | 669.4 |

Example 20

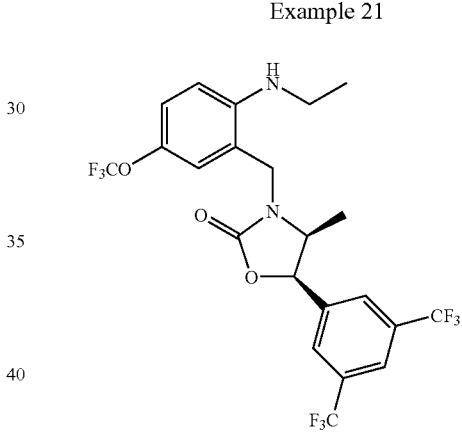

(4S,5R)-5-[3,5-bis(trifluoromethyl)phenyl]-3-[2-{1-[ethyl(isoropyl)amino]propyl}-5-(trifluoromethyl)benzyl]-4-methyl-1,3-oxazolidin-2-one To a solution of (4S,5R)-5-[3,5-bis(trifluoromethyl)phenyl]-3-[2-[1-(isopropylamino)propyl]-5-(trifluoromethyl)benzyl]-4-methyl-1,3-oxazolidin-2-one (28.5 mg, 0.0500 mmol) in dichloroethane (1 mL) was added acetaldehyde (2 mL) and NaBH(OAc)$_3$ (excess). The reaction was stirred at room temperature for 16 hours, and then diluted with EtOAc (10 mL) and washed with water and brine (5 mL each). The organic layer was dried over Na$_2$SO$_4$, filtered, and concentrated. Purification by PTLC (50% EtOAc/hexanes) afforded (4S,5R)-5-[3,5-bis(trifluoromethyl)phenyl]-3-[2 {1-[ethyl(isopropyl)amino]propyl}-5-(trifluoromethyl)benzyl]-4-methyl-1,3-oxazolidin-2-one. R$_f$=0.53 (50% EtOAc/hexanes). LCMS=599.3 (M+1)+. $^1$H NMR (CDCl$_3$, 500 MHz) δ 7.90 (s, 1H), 7.81 (s, 2H), 7.56-7.49 (m, 3H), 5.78-5.74 (m, 1H), 5.02 (d, J=16.4 Hz, 1H), 4.74-4.71 (m, 1H), 4.07-4.04 (m, 1H), 3.90-3.87 (m, 1H), 2.89-2.85 (m, 1H), 2.62-2.52 (m, 2H), 2.00-1.96 (m, 1H), 1.79-1.72 (m, 1H), 1.26-0.69 (m, 15H).

Example 21

(4S,5R)-5-[3,5-bis(trifluoromethyl)-phenyl]-3-[2-(ethylamino)-5-(trifluoromethoxy)benzyl]-4-methyl-1,3-oxazolidin-2-one To a solution of (4S,5R)-3-[2-amino-5-(trifluoromethoxy)benzyl]-5-[3,5-bis(trifluoromethyl)phenyl]-4-methyl-1,3-oxazolidin-2-one (80 mg, 0.159 mmol) in dichloroethane (1.6 mL) was added acetaldehyde (9 µL, 0.159 mmol) and NaBH(OAc)$_3$ (67 mg, 0.318 mmol). The reaction was stirred at room temperature, and after 30 minutes acetaldehyde (4.5 µL, 0.80 mmol) was added. After an hour, additional acetaldehyde (4.5 µL, 0.80 mmol) was added. After an additional hour, the reaction was diluted with EtOAc (20 ml) and washed with saturated NH$_4$Cl solution and brine (10 mL each). The organic layer was dried over Na$_2$SO$_4$, filtered, and concentrated. Purification of the residue by flash chromatography on silica gel (10 to 20% EtOAc/hexanes) afforded (4S,5R)-5-[3,5-bis(trifluoromethyl)phenyl]-3-[2-(ethylamino)-5-(trifluoromethoxy)benzyl]-4-methyl-1,3-oxazolidin-2-one. R$_f$=0.66 (25% EtOAc/hexanes). LCMS=531.2 (M+1)+. $^1$H NMR (CDCl$_3$, 500 MHz), 7.88 (s, 1H), 7.73 (s, 2H), 7.10 (dd, J=2.1, 8.8 Hz, 1H), 6.90 (d, J=2.4 Hz, 1H), 6.59 (d, J=8.9 Hz, 1H), 5.66 (d, J=8.4 Hz, 1H), 4.81 (s, 1H), 4.70 (d, J=15.4 Hz, 1H), 4.08 (d, J=15.4 Hz, 1H), 4.06-4.00 (m, 1H), 3.20-3.13 (m, 2H), 1.32 (t, J=7.1 Hz, 3H), 0.78 (d, J=6.6 Hz, 3H).

In a similar manner, the following compounds were synthesized:

| EXAMPLE | MOLECULAR STRUCTURE | LCMS (M + 1)+ |
|---------|---------------------|---------------|
| 22 | 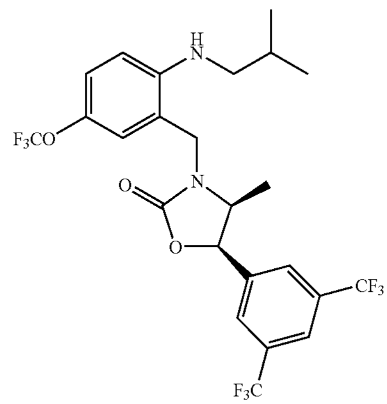 | 559.1 |
| 23 | 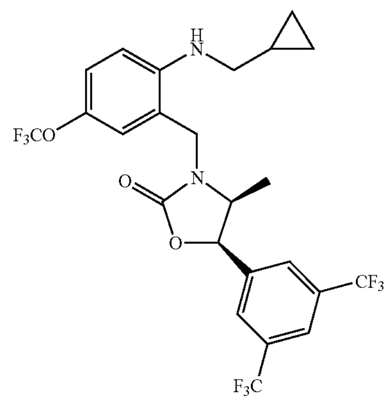 | 557.3 |
| 24 | 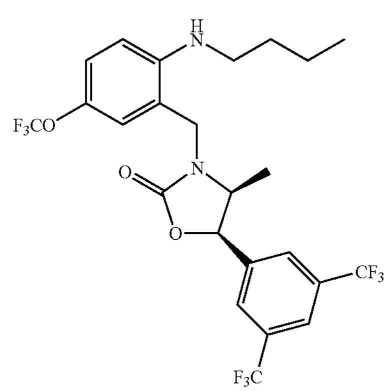 | 559.4 |

-continued

| EXAMPLE | MOLECULAR STRUCTURE | LCMS (M + 1)+ |
|---|---|---|
| 25 | 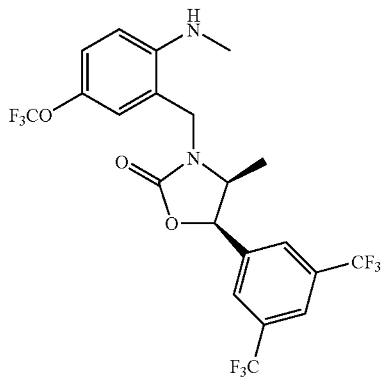 | 517.4 |
| 26 | 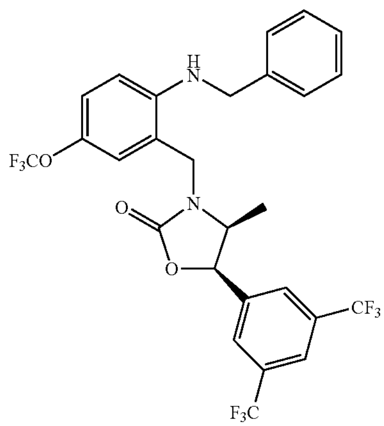 | 593.3 |
| 27 | 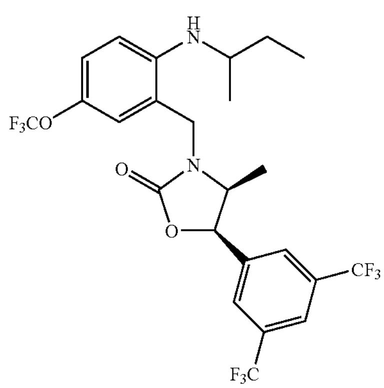 | 559.3 |
| 28 | 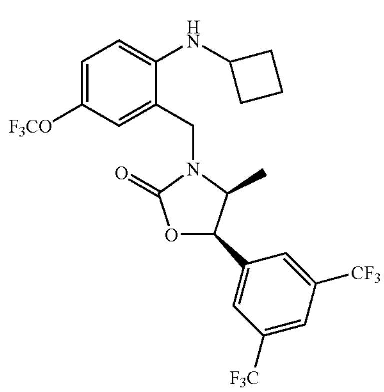 | 557.1 |

| EXAMPLE | MOLECULAR STRUCTURE | LCMS (M + 1)+ |
|---|---|---|
| 29 | 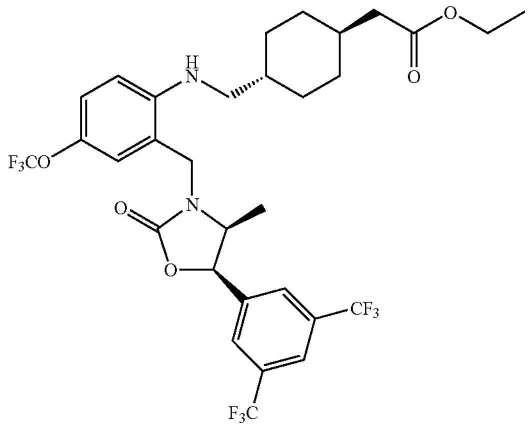 | 685.3 |
| 30 | 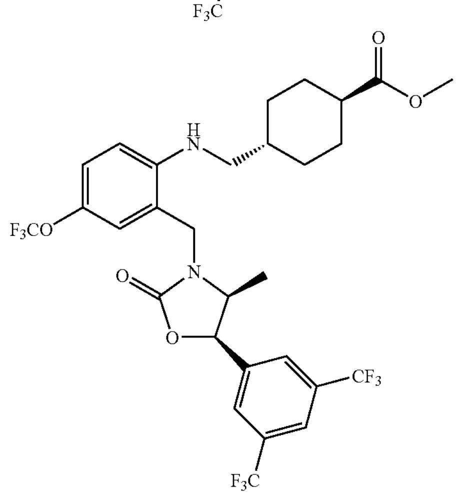 | 657.2 |

Example 31

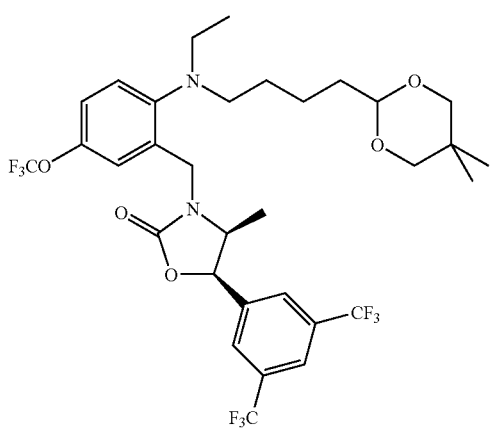

(4S,5R)-5-[3,5-bis(trifluoromethyl)phenyl]-3-[2-[[4-(5,5-dimethyl-1,3-dioxan-2-butyl](ethyl)amino]-5-(trifluoromethoxy)benzyl]-4-methyl-1,3-oxazolidin-2-one To a solution of (4S,5R)-5-[3,5-bis(trifluoromethyl)phenyl]-3-[2-(ethylamino)-5-(trifluoromethoxy)benzyl]-4-methyl-1,3-oxazolidin-2-one (68.2 mg, 0.129 mmol) in dichloroethane (2 mL) was added 4-(5,5-dimethyl-1,3-dioxan-2-yl)butanal (119 mg, 0.643 mmol) and NaBH(OAc)₃ (136 mg, 0.643 mmol). The reaction was stirred at room temperature for 72 hours and then diluted with EtOAc (30 mL), quenched with saturated NH₄Cl solution (10 mL), and washed with water and brine (10 mL each). The organic layer was dried over Na₂SO₄, filtered, and concentrated. Purification of the residue by flash chromatography on silica gel (0 to 25% EtOAc/hexanes) afforded (4S,5R)-5-[3,5-bis(trifluoromethyl)phenyl]-3-[2-[[4-(5,5-dimethyl-1,3-dioxan-2-yl)butyl](ethyl)amino]-5-(trifluoromethoxy)benzyl]-4-methyl-1,3-oxazolidin-2-one. $R_f$=0.62 (25% EtOAc/hexanes). LCMS=701.3 (M+1)+. ¹H NMR (CDCl₃, 500 MHz) δ7.97 (s, 1H), 7.85 (s, 2H), 7.23-7.19 (m, 3H), 5.79 (d, J=8.1 Hz, 1H), 4.79 (d, J=16.0 Hz, 1H), 4.62 (d, J=16.0 Hz, 1H), 4.43 (t, J=4.9 Hz, 1H), 4.11-4.01 (m, 1H), 3.61 (d, J=1.1 Hz, 2H), 3.44 (d, J=10.8 Hz, 2H), 3.06-3.00 (m, 4H), 1.71-1.41 (m, 6H), 1.12 (s, 3H), 1.05-1.01 (t, J=7.0 Hz, 3H), 0.77 (s, 3H), 0.74 (d, J=6.6 Hz, 3H).

In a similar manner, the following compounds were synthesized:

| EXAMPLE | MOLECULAR STRUCTURE | LCMS (M + 1)+ |
|---|---|---|
| 32 | 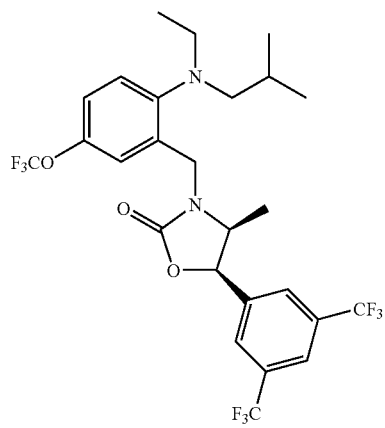 | 587.5 |
| 33 | 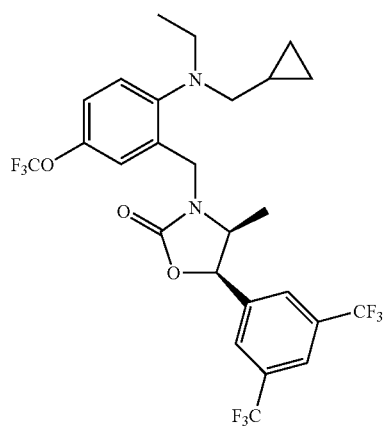 | 585.2 |
| 34 | 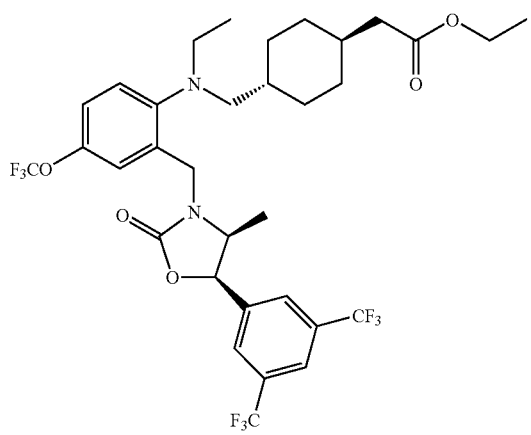 | 713.2 |

-continued
| EXAMPLE | MOLECULAR STRUCTURE | LCMS (M + 1)+ |
|---|---|---|
| 35 | 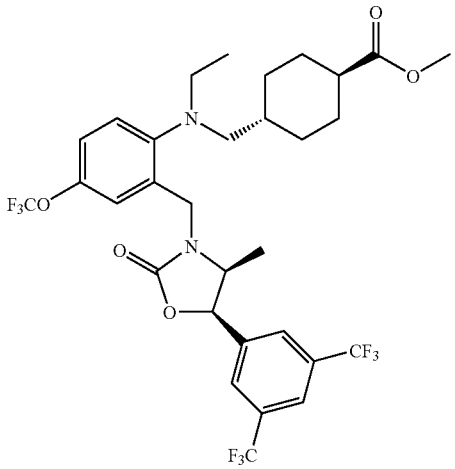 | 685.3 |
| 36 | 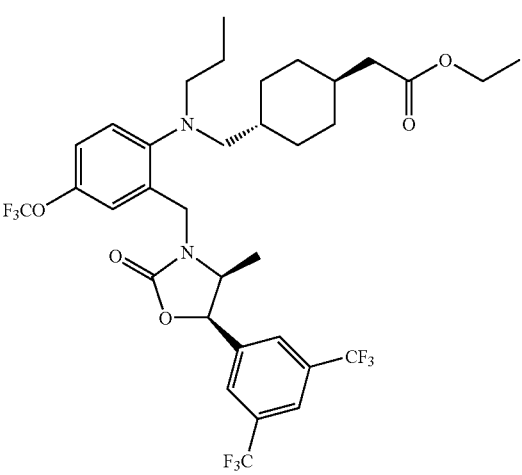 | 727.4 |
| 37 | 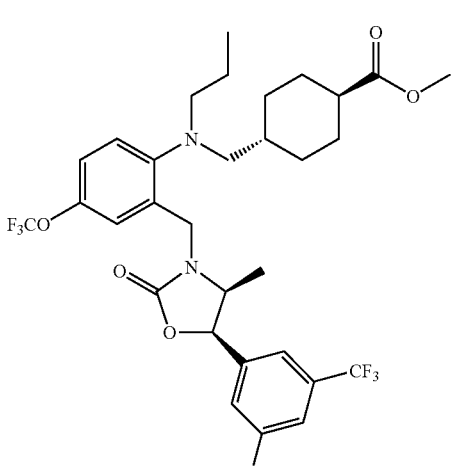 | 699.3 |

Example 38

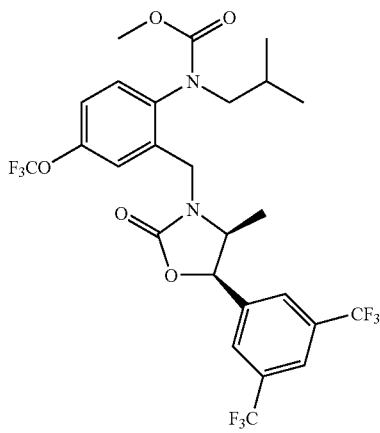

methyl [2-({(4S,5R)-5-[3,5-bis(trifluoromethyl)phenyl]-4-methyl-2-oxo-1,3-oxazolidin-3-yl}methyl)-4-(trifluoromethoxy)phenyl]isobutylcarbamate To a solution of (4S,5R)-5-[3,5-bis(trifluoromethyl)phenyl]-3-[2-(isobutylamino)-5-(trifluoromethoxy)benzyl]-4-methyl-1,3-oxazolidin-2-one (25.6 mg, 0.0502 mmol) in CH$_2$Cl$_2$ (0.5 mL) was added methyl chloroformate (7.7 μL, 0.100 mmol), followed by EtN(i—Pr)$_2$ (70 μL, 0.402 mmol) The reaction was stirred at room temperature for 24 hours, and then methyl chloroformate (7.7 μL, 0.100) and EtN(i—Pr)$_2$ (70 μL, 0.402 mmol) were added. The reaction was stirred for 96 hours and then diluted with EtOAc (20 mL), and washed with saturated NaHCO$_3$ solution, brine, and 1 N HCl (10 mL each). The organic layer was dried over Na$_2$SO$_4$, filtered, and concentrated. Purification of the residue by PTLC (25% EtOAc/hexanes) afforded methyl [2-({(4S,5R)-5-[3,5-bis(trifluoromethyl)phenyl]-4-methyl-2-oxo-1,3-oxazolidin-3-yl}methyl)-4-(trifluoromethoxy)phenyl]isobutylcarbamate. R$_f$=0.29 (25% EtOAc/hexanes). LCMS=617.3 (M+1)$^+$. $^1$H NMR (CDCl$_3$, 500 MHz) δ 7.89-7.87 (m, 1H), 7.78-7.76 (m, 2H), 7.24-7.17 (m, 3H), 5.73-5.71 (m, 1H), 5.01-4.75 (m, 2H), 4.07-3.06 (m, 3H), 1.83-1.75 (m, 1H), 1.27-1.21 (m, 3H), 0.99-0.91 (m, 6H), 0.70-0.68 (m, 3H).

In a similar manner, the following compounds were synthesized:

| EXAMPLE | MOLECULAR STRUCTURE | LCMS (M + 1)$^+$ |
|---|---|---|
| 39 | 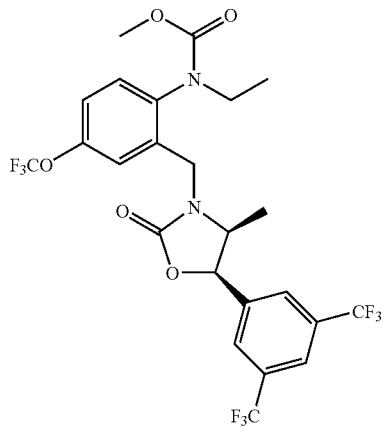 | 589.3 |
| 40 | 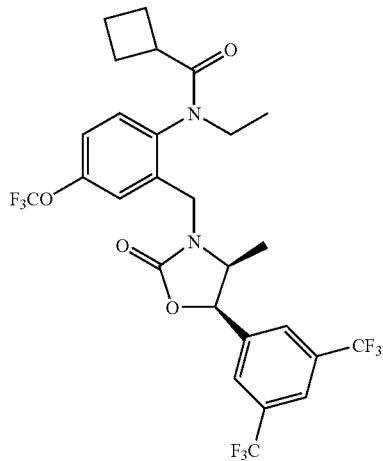 | 613.4 |

-continued
| EXAMPLE | MOLECULAR STRUCTURE | LCMS (M + 1)+ |
|---------|--------------------|----|
| 41 | 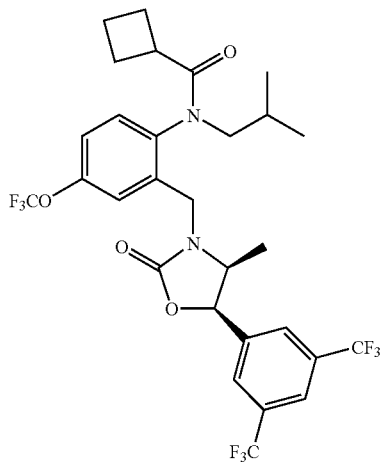 | 641.4 |
| 42 | 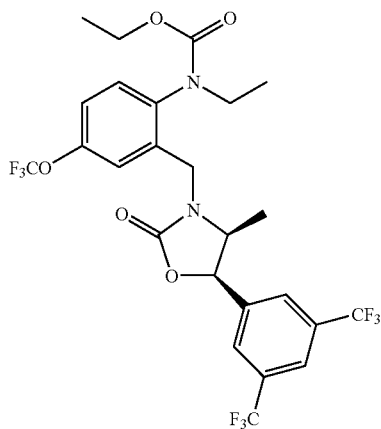 | 603.4 |
| 43 | 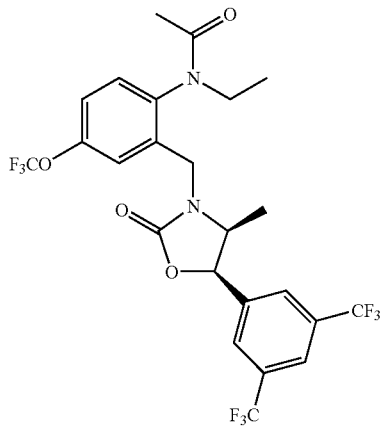 | 573.3 |

-continued
| EXAMPLE | MOLECULAR STRUCTURE | LCMS (M + 1)+ |
|---|---|---|
| 44 | 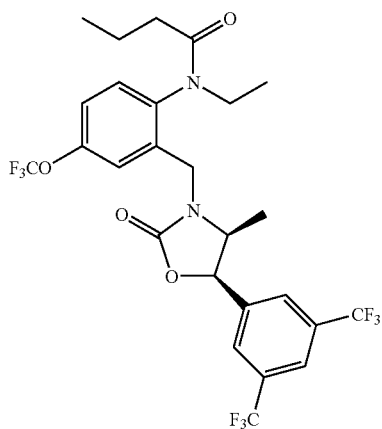 | 601.3 |
| 45 | 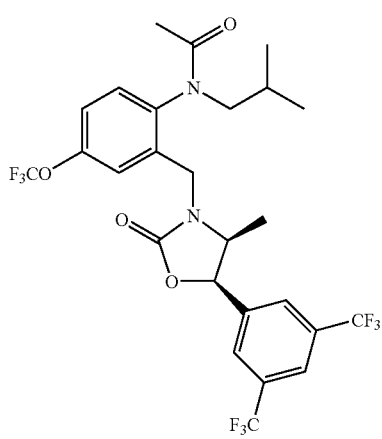 | 601.4 |
| 46 | 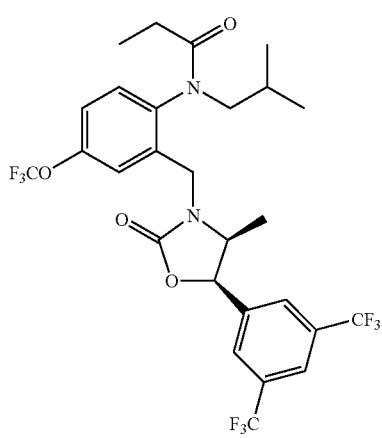 | 615.3 |

-continued
| EXAMPLE | MOLECULAR STRUCTURE | LCMS (M + 1)+ |
| --- | --- | --- |
| 47 | 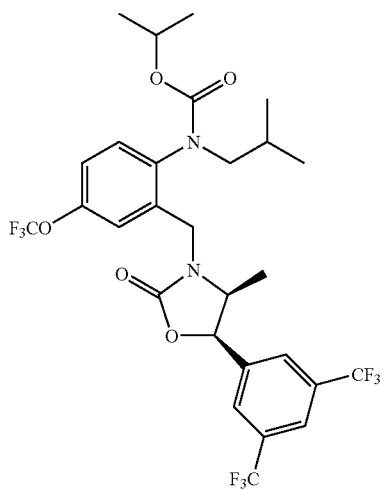 | 645.5 |
| 48 | 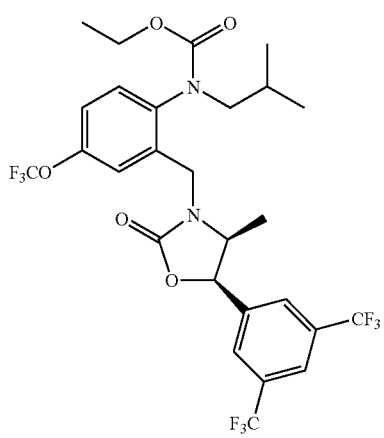 | 631.3 |
| 49 | 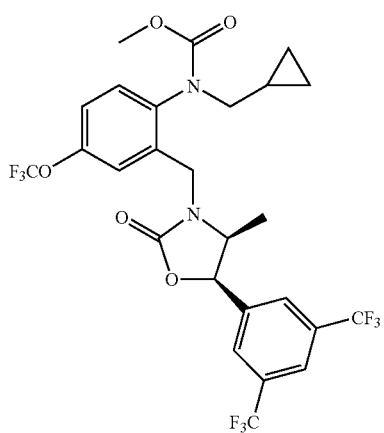 | 615.4 |

-continued
| EXAMPLE | MOLECULAR STRUCTURE | LCMS (M + 1)+ |
|---------|---------------------|---------------|
| 50 | 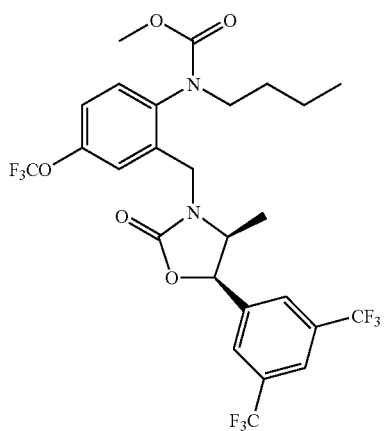 | 617.4 |
| 51 | 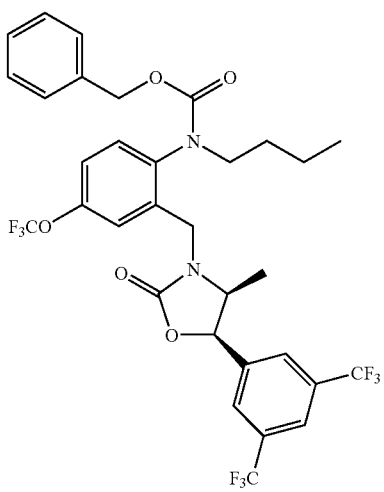 | 693.4 |
| 52 | 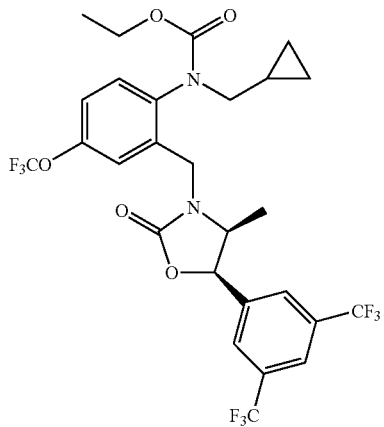 | 629.4 |

-continued
| EXAMPLE | MOLECULAR STRUCTURE | LCMS (M + 1)+ |
|---|---|---|
| 53 | 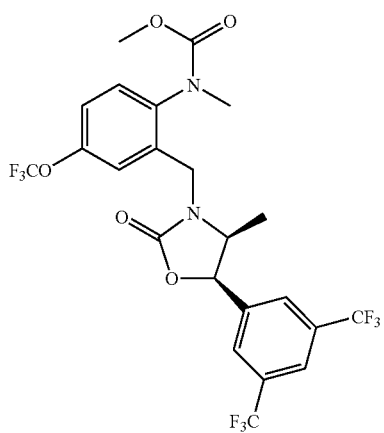 | 575.3 |
| 54 | 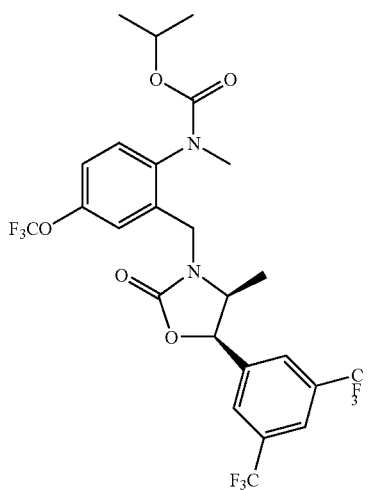 | 603.3 |
| 55 | 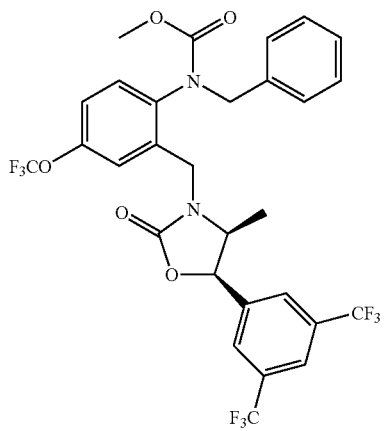 | 651.4 |

-continued

| EXAMPLE | MOLECULAR STRUCTURE | LCMS (M + 1)+ |
|---------|---------------------|---------------|
| 56 | 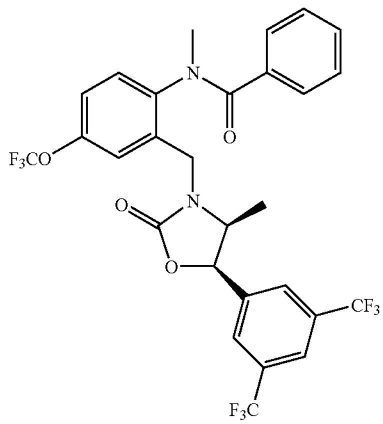 | 621.4 |
| 57 | 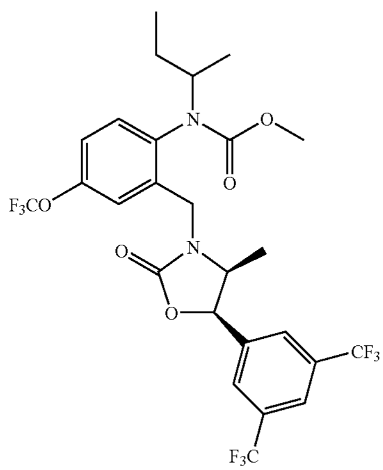 | 617.4 |
| 58 | 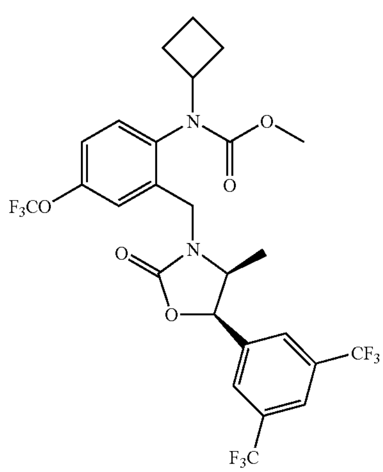 | 615.2 |

Example 59

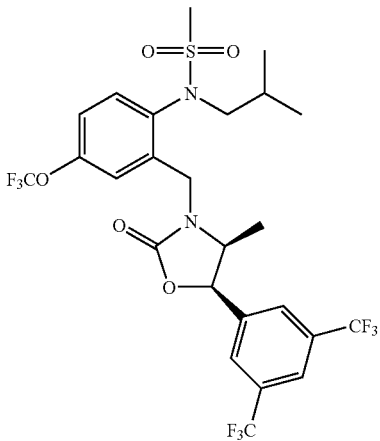

N-[2-({(4S,5R)-5-[3,5-bis(trifluoromethyl)phenyl]-4-methyl-2-oxo-1,3-oxazolidin-3-yl}methyl)-4-(trifluoromethoxy)phenyl]-N-isobutylmethanesulfonamide To a solution of (4S,5R)-5-[3,5-bis(trifluoromethyl)phenyl]-3-[2-(isobutylamino)-5-(trifluoromethoxy)benzyl]-4-methyl-1,3-oxazolidin-2-one (9.2 mg, 0.0165 mmol) in pyridine (300 µL) was added methanesulfonyl chloride (100 µL, 1.29 mmol) and excess 4-dimethylaminopyridine. The reaction was stirred at 65° C. for 4 hours and then diluted with EtOAc (15 mL), and washed with 1 N HCl (2×10 mL) and brine (10 mL). The organic layer was dried over $Na_2SO_4$, filtered, and concentrated. Purification of the residue by PTLC (60% EtOAc/hexanes) N-[2-({(4S,5R)-5-[3,5-bis(trifluoromethyl)phenyl]-4-methyl-2-oxo-1,3-oxazolidin-3-yl}methyl)-4-(trifluoromethoxy)phenyl]-N-isobutylmethanesulfonamide. $R_f$=0.25 (60% EtOAc/hexanes). LCMS=637.4 (M+1)+. $^1H$ NMR (CDCl$_3$, 500 MHz) δ 7.91 (s, 1H), 7.80 (s, 2H), 7.34-2.46 (m, 3H), 5.79-5.76 (m, 1H), 4.90-4.58 (m, 2H), 4.19-4.14 (m, 1H), 3.51-3.46 (m, 1H), 3.34-3.32 (m, 1H), 2.97 (m, 3H), 1.25 (m, 1H), 0.93-0.87 (m, 6H), 0.70-0.66 (m, 3H).

Example 60

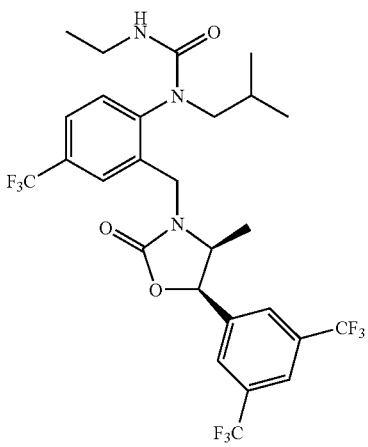

N-[2-({(4S,5R)-5-[3,5-bis(trifluoromethyl)phenyl]-4-methyl-2-oxo-1,3-oxazolidin-3-yl}methyl)-4-(trifluoromethoxy)phenyl]-N'-ethyl-N-isobutylurea To a solution of (4S,5R)-5-[3,5-bis(trifluoromethyl)phenyl]-3-[2-(isobutylamino)-5-(trifluoromethoxy)benzyl]-4-methyl-1,3-oxazolidin-2-one (19.9 mg, 0.0357 mmol) in THF (350 µL) was added a 1 M solution of NaHMDS in THF (35.7 µL, 0.0357 mmol). The reaction was stirred at room temperature and, after 5 minutes, ethyl isocyanate (2.8 µL, 0.0357 mmol) was added. After an hour, a 1 M solution of NaHMDS in THF (35.7 µL, 0.0357 mmol) was added, followed by ethyl isocyanate (2.8 µL, 0.0357 mmol). After 10 minutes, a 1 M solution of NaHMDS in THF (35.7 µL, 0.0357 mmol) was added, followed by ethyl isocyanate (2.8 µL, 0.0357 mmol). After 5 minutes, the reaction was quenched with saturated NH$_4$Cl solution (2 mL), diluted with EtOAc (15 mL), and washed with brine (5 mL). The organic layer was dried over Na$_2$SO$_4$, filtered, and concentrated. Purification of the residue by PTLC (30% EtOAc/hexanes) afforded N-[2-({(4S,5R)-5-[3,5-bis(trifluoromethyl)phenyl]-4-methyl-2-oxo-1,3-oxazolidin-3-yl}methyl)-4-(trifluoromethoxy)phenyl]-N'-ethyl-N'-isobutylurea. $R_f$=0.35 (30% EtOAc/hexanes). LCMS=630.4 (M+1)+. $^1H$ NMR (CDCl$_3$, 500 MHz) δ 7.76 (s, 2H), 7.71 (s, 1H), 7.08 (d, J=8.7 Hz, 1 H), 6.92 (s, 1H), 6.77 (d, J=9.0 Hz, 1H), 5.95 (d, J=7.3 Hz, 1H), 4.85-4.76 (m, 2H), 4.26 (d, J=14.1 Hz, 1H), 4.16 (d, J=14.0 Hz, 1H), 3.69-3.60 (m, 2H), 3.23-3.17 (m, 2H), 1.89-1.86 (m, 1H), 1.33 (d, J=7.1 Hz, 3H), 1.13 (t, J=7.1 Hz, 3H), 0.85 (d, J=6.6 Hz, 3H), 0.76 (d, J=6.6 Hz, 3H).

Example 61

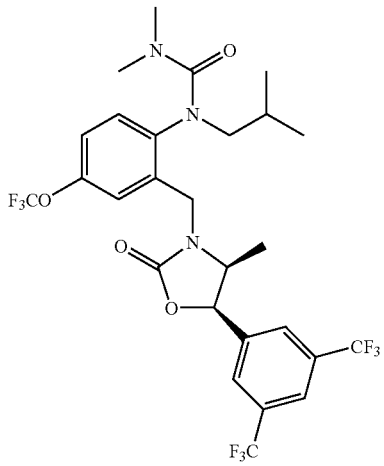

N-[2-({(4S,5R)-5-[3,5-bis(trifluoromethyl)-phenyl]-4-methyl-2-oxo-1,3-oxazolidin-3-yl}methyl)-4-(trifluoromethoxy)phenyl]-N-isobutyl-N',N-dimethylurea To a solution of (4S,5R)-5-[3,5-bis(trifluoromethyl)phenyl]-3-[2-(isobutylamino)-5-(trifluoromethoxy)benzyl]-4-methyl-1,3-oxazolidin-2-one (21.8 mg, 0.0391 mmol) in THF (400 µL) was added a 1 M solution of NaHMDS in THF (39.1 µL, 0.0391 mmol), followed by a solution of dimethylaminocarbonyl chloride (3.58 µL, 0.0391) in ether (70 µL). After 10 minutes of stirring at room temperature, NaHMDS (18.5 µL, 0.0185 mmol) was added, followed by a solution of dimethylaminocarbonyl chloride (1.79 µL, 0.0185 mmol) in ether (40 µL). After 5 minutes, the reaction was quenched with saturated NH₄Cl solution (2 mL), diluted with EtOAc (10 mL), and washed with brine (5 mL). The organic layer was dried over Na₂SO₄, filtered, and concentrated. Purification of the residue by PTLC (25% EtOAc/hexanes) afforded N-[2-({(4S,5R)-5-[3,5-bis(trifluoromethyl)phenyl]-4-methyl-2-oxo-1,3-oxazolidin-3-yl}methyl)-4-(trifluoromethoxy)phenyl]-N-isobutyl-N'-N'-dimethylurea. $R_f$=0.33 (25% EtOAc/hexanes). LCMS=630.4 (M+1)⁺. ¹H NMR (CDCl₃, 500 MHz) δ 7.75 (s, 2H), 7.71 (s, 1H), 7.08 (dd, J=8.7, 2.0 Hz, 1H), 6.92 (d, J=1.9 Hz, 1H), 6.77 (d, J=8.0 Hz, 1H), 5.93 (d, J=7.3 Hz, 1H), 4.85-4.82 (m, 1H), 4.27 (d, J=14.0 Hz, 1H), 4.15 (d, J=14.2 Hz, 1H), 3.64 (d, J=7.4 Hz, 2H), 3.05 (s, 3H), 2.89 (s, 3H), 1.88-1.86 (m, 1H), 1.36 (d, J=7.1 Hz, 3H), 0.85 (d, J=6.6 Hz, 3H), 0.75 (d, J=6.6 Hz, 3H).

Example 62

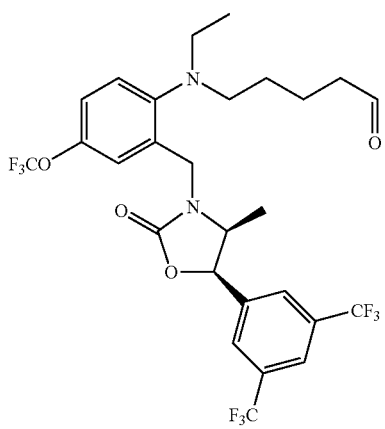

5-[[2-({(4S,5R)-5-[3,5-bis(trifluoromethyl)phenyl]-4-methyl-2-oxo-1,3-oxazolidin-3-yl}methyl)-4-(trifluoromethoxy)phenyl](ethyl)amino]pentanal To a solution of (4S,5R)-5-[3,5-bis(trifluoromethyl)phenyl]-3-[2-[[4-(5,5-dimethyl-1,3-dioxan-2-yl)butyl](ethyl)amino]-5-(trifluoromethoxy)benzyl]-4-methyl-1,3-oxazolidin-2-one (20 mg, 0.0286 mmol) in THF (3 mL) and water (1 mL) was added p-toluene sulfonic acid (excess). The reaction was stirred at room temperature for 16 hours, and then brought to reflux and stirred for 24 hours. The mixture was diluted with EtOAc (20 mL) and washed with saturated NaHCO₃ solution and brine (10 mL each). The organic layer was dried over Na₂SO₄, filtered, and concentrated. Purification of the residue by PTLC (35% EtOAc/hexanes) afforded 5-[[2-({(4S,5R)-5-[3,5-bis(trifluoromethyl)phenyl]-4-methyl-2-oxo-1,3-oxazolidin-3-yl}methyl)-4-(trifluoromethoxy)phenyl](ethyl)amino]pentanal. $R_f$=0.24 (35% EtOAc/hexanes). LCMS=615.2 (M+1)⁺. ¹H NMR (CDCl₃, 500 MHz), 9.72 (s, 1H), 7.89 (s, 1H), 7.79 (s, 2H), 7.19-7.12 (m, 3H), 5.73 (d, J=8.2 Hz, 1H), 4.73 (d, J=16.3 Hz, 1H), 4.53 (d, J=16.0 Hz, 1H), 4.04-4.00 (m, 1H), 2.95-2.85 (m, 4H), 2.42 (t, J=7.1 Hz, 2H), 1.61-1.37 (m, 4H), 0.98 (t, J=7.1 Hz, 3H), 0.67 (d, J=6.6 Hz, 3H).

Example 63

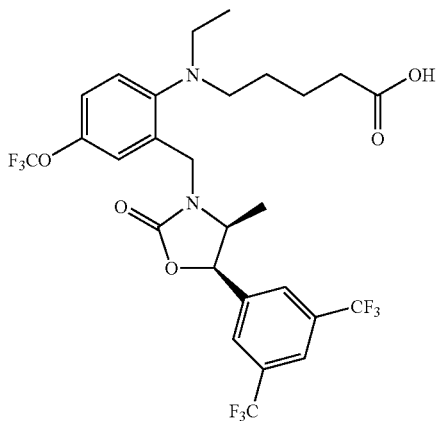

5-[[2-({(4S,5R)-5-[3,5-bis(trifluoromethyl)phenyl]-4-methyl-2-oxo-1,3-oxazolidin-3-yl}methyl)-4-(trifluoromethoxy)phenyl](ethyl)amino]pentanoic acid To a solution of 5-[[2-({(4S,5R)-5-[3,5-bis(trifluoromethyl)phenyl]-4-methyl-2-oxo-1,3-oxazolidin-3-yl}methyl)-4-(trifluoromethoxy)phenyl](ethyl)amino]pentanal (6.8 mg, 0.011 mmol) in THF (20 µL) and t-BuOH (60 µL) was added 2-methyl-2-butene (20 µL), followed by a solution of NaClO₂ (3.0 mg, 0.024 mmol) and NaH₂PO₄ (3.5 mg, 0.024 mmol) in water (25 µL). The reaction was stirred at room temperature for 30 minutes and then diluted with EtOAc (8 mL) and water (2 mL), acidified with 1 N HCl (2 mL), and washed with brine (5 mL). The organic layer was dried over Na₂SO₄, filtered, and concentrated. Purification of the residue by PTLC (EtOAc) afforded 5-[[2-({(4S,5R)-5-[3,5-bis(trifluoromethyl)phenyl]-4-methyl-2-oxo-1,3-oxazolidin-3-yl}methyl)-4-(trifluoromethoxy)phenyl](ethyl)amino]pentanoic acid. $R_f$=0.20 (EtOAc). LCMS=631.3 (M+1)⁺. ¹H NMR (CDCl₃, 500 MHz) δ 7.88 (s, 1H), 7.78 (s, 2H), 7.18-7.15 (m, 3H), 5.73 (d, J=8.0 Hz, 1H), 4.75 (d, J=16.5 Hz, 1H), 4.58 (m, 1H), 4.03 (s, 1H), 2.97 (m, 4H), 2.31 (t, J=7.3 Hz, 2H), 1.40-1.23 (m, 5H), 1.00 (t, J=6.7 Hz, 3H), 0.69 (d, J=6.4 Hz, 3H).

Example 64

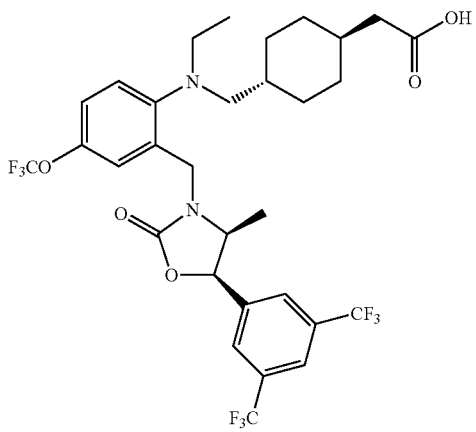

(trans-4-{[[2-({(4S,5R)-5-[3,5-bis(trifluoromethyl)phenyl]-4-methyl-2-oxo-1,3-oxazolidin-3-yl}methyl)-4-(trifluoromethoxy)phenyl](ethyl)amino]methyl}cyclohexyl)acetic acid To a solution of ethyl (trans-4-{[[2-({(4S,5R)-5-[3,5-bis(trifluoromethyl)phenyl]-4-methyl-2-oxo-1,3-oxazolidin-3-yl}methyl)-4-(trifluoromethoxy)phenyl](ethyl)amino]methyl}cyclohexyl)acetate (29 mg, 0.0407 mmol) in EtOH (1 mL) was added 4 M KOH (100 µL). The reaction was stirred at room temperature for 30 minutes and 4 M KOH (100 µL) was added. After an additional 30 minutes 4 M KOH (100 µL) was added. After 30 min the reaction was quenched with 1 N HCl (1.5 mL) and then neutralized with saturated NaHCO$_3$ solution. The mixture was extracted with EtOAc (2×20 mL) and washed with brine. The organic layer was dried over Na$_2$SO$_4$, filtered, and concentrated. Purification of the residue by PTLC (EtOAc+1% AcOH) afforded (trans-4-{[[2-({(4S,5R)-5-[3,5-bis(trifluoromethyl)phenyl]-4-methyl-2-oxo-1,3-oxazolidin-3-yl}methyl)-4-(trifluoromethoxy)phenyl](ethyl)amino]methyl}cyclohexyl)acetic acid. R$_f$=0.94 (EtOAc+1% AcOH). LCMS=685.3 (M+1)$^+$. $^1$H NMR (CDCl$_3$, 500 MHz) δ 7.91 (s, 1H), 7.80 (s, 2H), 7.20-7.12 (m, 3H), 5.76 (d, J=8.1 Hz, 1H), 4.74 (d, J=16.3 Hz, 1H), 4.59 (d, J=16.3 Hz, 1H), 4.04-4.00 (m, 1H), 2.97-2.75 (m, 4H), 1.81-0.88 (m, 15H), 0.66 (d, J=6.5 Hz, 3H).

In a similar manner, the following compounds were synthesized:

| EXAMPLE | MOLECULAR STRUCTURE | LCMS (M + 1)$^+$ |
|---|---|---|
| 65 | 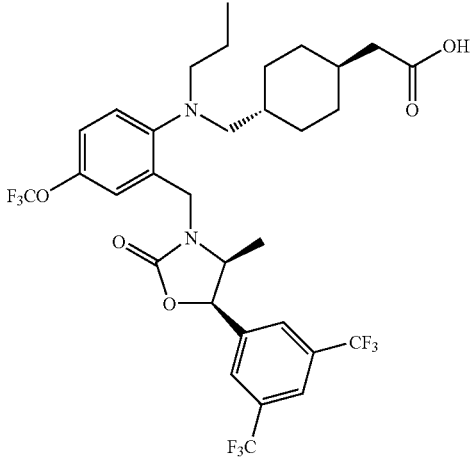 | 699.3 |
| 66 | 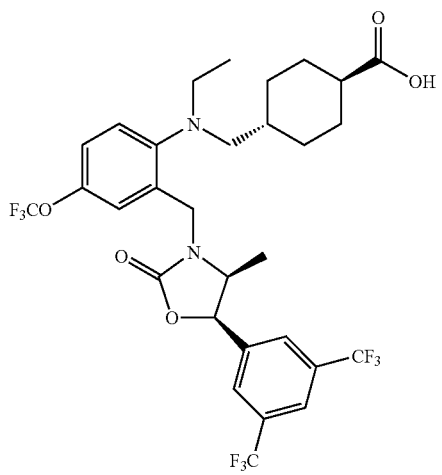 | 671.3 |

| EXAMPLE | MOLECULAR STRUCTURE | LCMS (M + 1)+ |
|---|---|---|
| 67 | 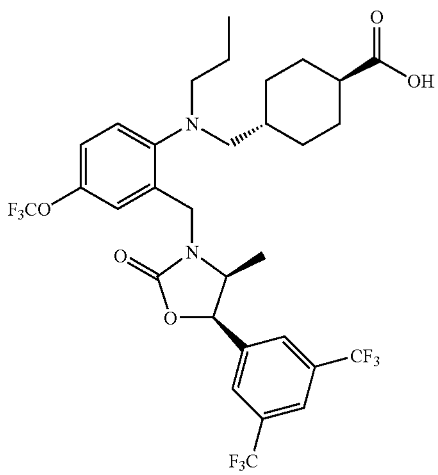 | 685.4 |

Example 68

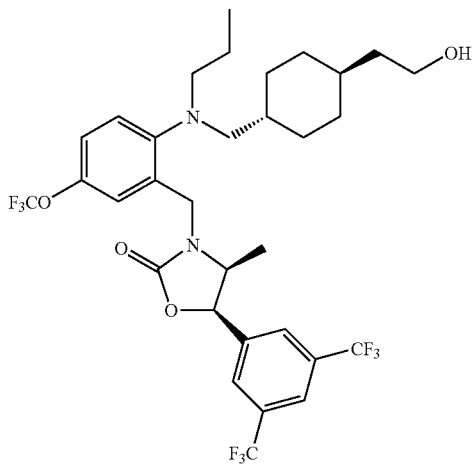

(4S,5R)-5-[3,5-bis(trifluoromethyl)phenyl]-3-[2-[{
[trans-4-(2-hydroxyethyl)cyclohexyl]methyl}(pro-
pyl)amino]-5-(trifluoromethoxy)benzyl]-4-methyl-1,
3-oxazolidin-2-one To a solution of (trans-4-{[[2-({(4S,5R)-5-[3,5-bis(trifluo-romethyl)phenyl]-4-methyl-2-oxo-1,3-oxazolidin-3-yl}methyl)-4-(trifluoromethoxy)phenyl](propyl)amino] methyl}cyclohexyl)acetic acid (8.8 mg, 0.0126 mmol) in THF (1 mL) was added a 1 M solution of $BH_3$ in THF (75 μL, 0.075 mmol). The reaction was stirred at room temperature for 2 hours and then quenched with water (5 mL), diluted with EtOAc (15 mL), and washed with brine (5 mL). The organic layer was dried over $Na_2SO_4$, filtered, and concentrated. Purification of the residue by flash chromatography on silica gel (10 to 50% EtOAc/hexanes) afforded (4S,5R)-5-[3,5-bis(trifluoromethyl)phenyl]-3-[2-[{[trans-4-(2-hydroxyethyl)cyclohexyl]methyl}(propyl)amino]-5-(trifluoromethoxy)benzyl]-4-methyl-1,3-oxazolidin-2-one. $R_f$=0.09 (25% EtOAc/hexanes). LCMS=685.3 (M+1)+. $^1H$ NMR ($CDCl_3$, 500 MHz) δ 7.89 (s, 1H), 7.78 (s, 2H), 7.16 (d, J=8.9 Hz, 2H), 7.10 (d, J=8.8 Hz, 1H), 5.74 (d, J=8.0 Hz, 1H), 4.72 (d, J=16.4 Hz, 1H), 4.58 (d, J=16.4 Hz, 1H), 4.02-3.98 (m, 1H), 3.66-3.64 (m, 2H), 2.77-2.73 (m, 4H), 1.77-0.81 (m, 17H), 0.64 (d, J=6.6 Hz, 3H).

Example 69

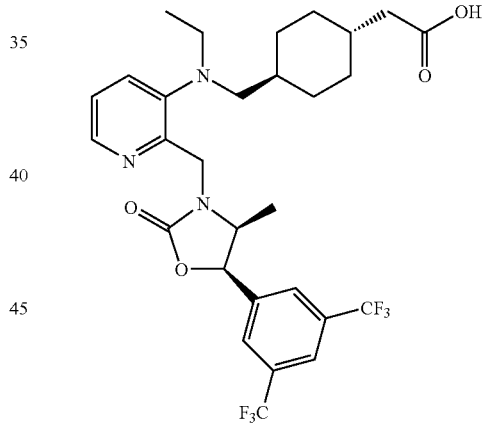

(trans)-4-{[[2-({(4S,5R)-5-[3,5-Bis(trifluoromethyl)
phenyl]-4-methyl-2-oxo-1,3-oxazolidin-3-yl}methyl)
pyridin-3-yl](ethyl)amino]methyl}cyclohexyl)acetic
acid Step A: 3-fluoropyridine-2-carbaldehyde n-Butyl lithium (1.6 M in hexanes, 6.86 mL, 11.0 mmol) was added to a stirred solution of 1,4-diazobicyclo[2.2.2]-octane (1.23 g, 11.0 mmol) in dry $Et_2O$ (55 mL) at −78° C. under $N_2$. The reaction was warmed to −20° C. and stirred for 1 h. The reaction was cooled to −78° C. and a solution of 3-fluoropyridine (1.07 g, 11.0 mmol) in $Et_2O$ (5.5 mL) was added dropwise via cannula. The reaction was warmed to −60° C. and stirred for 1 h after which time a yellow precipitate appeared. DMF (803 mg, 847 μL, 12.1 mmol) was added dropwise and the reaction was gradually warmed to −20° C.

over 4 h. Water (20 mL) was added and the mixture was extracted with Et₂O (3×40 mL). The combined extracts were dried (Na₂SO₄) and concentrated in vacuo to give the crude product. This was purified by flash chromatography (Si, 25×160 mm, 0-60% EtOAc in hexanes gradient) to afford 3-fluoropyridine-2-carbaldehyde (152.3 mg, 11%). $R_f$=0.23 (20% EtOAc/hexanes). LCMS calc.=126.0; found=125.9 $(M+1)^+$. ¹H NMR (500 MHz, CDCl₃): δ 10.14 (d, J=2.4 Hz, 1H); 8.57 (m, 1H); 7.57-7.53 (m, 2H).

Step B: ethyl (trans-4-{[ethyl(2-formylpyridin-3-yl)amino]methyl}cyclohexyl)acetate A mixture of 3-fluoropyridine-2-carbaldehyde (122.7 mg, 0.981 mmol), ethyl{trans-4-[(ethylamino)methyl]cyclohexyl}acetate (202.7 mg, 0.892 mmol), potassium carbonate (369.7 mg, 2.67 mmol) and dry toluene (13 mL) was heated at reflux under N₂ overnight. The reaction mixture was diluted with water (10 mL) and extracted with EtOAc (3×20 mL). The combined extracts were dried (Na₂SO₄) and concentrated in vacuo to give the crude product. This was purified by flash chromatography (Si, 12×160 mm, 0-50% EtOAc in hexanes gradient) to afford ethyl (trans-4-{[ethyl(2-formylpyridin-3-yl)amino]methyl}cyclohexyl)acetate as a yellow oil. $R_f$=0.79 (50% EtOAc/hexanes). LCMS calc.=333.2; found=333.3 $(M+1)^+$. ¹H NMR (600 MHz, CDCl₃): δ 10.13 (s, 1 H); 8.29 (d, J=4.1 Hz, 1 H); 7.41 (d, J=8.5 Hz, 1 H); 7.29 (dd, J=4.1, 8.4 Hz, 1 H); 4.08 (q, J=7.1 Hz, 2 H); 3.26 (q, J=7.0 Hz, 2 H); 3.05 (d, J=7.1 Hz, 2 H); 2.12 (d, J=6.9 Hz, 2 H); 1.71 (m, 4 H); 1.66 (m, 1 H); 1.41 (m, 1 H); 1.22-1.20 (t, J=7.1 Hz, 3 H); 1.06 (t, J=7.1 Hz, 3 H); 0.91-0.82 (m, 4 H).

Step C: ethyl [trans-4-({ethyl[2-(hydroxymethyl)pyridin-3-yl]amino}methyl)cyclohexyl]acetate Sodium borohydride (62.3 mg, 1.65 mmol) was added to a stirred solution of ethyl (trans-4-{[ethyl(2-formylpyridin-3-yl)amino]methyl}cyclohexyl)acetate (136.9 mg, 0.412 mmol) in EtOH (10 mL) at room temperature. The reaction was stirred at room temperature for 1 h, then diluted with water and most of the EtOH was removed in vacuo. The resulting aqueous slurry was extracted with EtOAc (3×20 mL) and the combined extracts were washed with brine (5 mL), dried (Na₂SO₄) and concentrated in vacuo to afford ethyl [trans-4-({ethyl[2-(hydroxymethyl)pyridin-3-yl]amino}methyl)cyclohexyl]acetate. LCMS calc.=335.2; found=335.3 $(M+1)^+$.

Step D: ethyl (trans-4-{[[2-(chloromethyl)pyridin-3-yl](ethyl)amino]methyl}cyclohexyl)acetate Thionyl chloride (470 mg, 288 μL, 3-95 mmol) was added to a stirred solution of ethyl [trans-4-({ethyl[2-(hydroxymethyl)pyridin-3-yl]amino}methyl)cyclohexyl]acetate (132.2 mg, 0.395 mmol) in dry CH₂Cl₂ (10 mL) at room temperature. The reaction was stirred overnight at room temperature then quenched with pyridine (425 μL) and washed with water. The aqueous layer was extracted with CH₂Cl₂ (2×20 mL) an the combined extracts were dried (Na₂SO₄) and concentrated in vacuo to afford ethyl (trans-4-{[[2-(chloromethyl)pyridin-3-yl](ethyl)amino]methyl}cyclohexyl)acetate. ¹H NMR (500 MHz, CDCl₃): δ 8.37 (dd, J=1.2, 4.5 Hz, 1 H); 7.51 (dd, J=1.4, 8.1 Hz, 1 H); 7.23 (dd, J 3.7, 8.3 Hz, 1 H); 4.86 (s, 2 H); 4.10 (q, J=7.1 Hz, 2 H); 3.03 (q, J=7.1 Hz, 2 H); 2.81 (d, J=7.1 Hz, 2 H); 2.14 (d, J=6.8 Hz, 2 H); 1.80-1.67 (m, 5 H); 1.42-1.29 (m, 1 H); 1.23 (t, J=7.1 Hz, 3 H); 0.99 (t, J=7.1 Hz, 3H); 0.94-0.86 (m, 4 H).

Step E: ethyl (trans-4-{[[2-({(4S,5R)-5-[3,5-bis(trifluoromethyl)phenyl]-4-methyl-2-oxo-1,3-oxazolidin-3-yl}methyl)pyridin-3-yl](ethyl)amino]methyl}cyclohexyl)acetate Potassium t-butoxide (55.3 mg, 0.493 mmol) was added to a stirred solution of (4S,5R)-5-[3,5-bis(trifluoromethyl)phenyl]-4-methyl-1,3-oxazolidin-2-one (180.2 mg, 0.575 mmol) in dry DMF (5 mL) at room temperature under N₂. The solution was stirred for 5 min at room temperature. A solution of ethyl (trans-4-{[[2-(chloromethyl)pyridin-3-yl](ethyl)amino]methyl}cyclohexyl)acetate (145.0 mg, 0.411 mmol) in dry DMF (2 mL) was added via cannula and the reaction was stirred at room temperature for 3 h. Saturated aqueous NH₄Cl (5 mL) and water (5 mL) were added and the mixture was extracted with EtOAc (3×20 mL). The combined extracts were dried (Na₂SO₄) and concentrated in vacuo to give the crude product. This was purified by flash chromatography (Si, 25×160 mm, 0-50% EtOAc in hexanes gradient) to afford ethyl (trans-4-{[[2-({(4S,5R)-5-[3,5-bis(trifluoromethyl)phenyl]-4-methyl-2-oxo-1,3-oxazolidin-3-yl}methyl)pyridin-3-yl](ethyl)amino]methyl}cyclohexyl)acetate. $R_f$=0.77 (50% EtOAc/hexanes). LCMS calc.=630.3; found=630.3 $(M+1)^+$. ¹H NMR (600 MHz, CDCl₃): i 8.31 (dd, J=1.3, 4.6 Hz, 1 H); 7.85 (s, 1 H); 7.80 (s, 2 H); 7.43 (dd, J=1.3, 8.1 Hz, 1 H); 7.17 (dd, J=4.7, 8.1 Hz, 1 H); 5.78 (d, J=8.5 Hz, 1 H); 4.91 (d, J=16.7 Hz, 1 H); 4.45 (d, J=16-7 Hz, 1 H); 4.36-4.30 (m, 1 H); 4.06 (q, J=7.1 Hz, 2 H); 2.96-2.90 (m, 2 H); 2.82-2.74 (m, 2 H); 2.11 (d, J=6.8 Hz, 2 H); 1.80-1.75 (m, 2 H); 1.73-1.67 (m, 3 H); 1.30 (m, 1 H); 1.20 (t, J=7.1 Hz, 3 H); 0.96 (t, J=7.0 Hz, 3H); 0.93-0.77 (m, 4 H); 0.66 (d, J=6.7 Hz, 3 H).

Step F: (trans)-4-{[[2-({(4S,5R)-5-[3,5-bis(trifluoromethyl)phenyl]-4-methyl-2-oxo-1,3-oxazolidin-3-yl}methyl)pyridin-3-yl](ethyl)amino]methyl}cyclohexyl)acetic acid Aqueous potassium hydroxide (4N, 100 μL) was added to a stirred solution of ethyl (trans-4-{[[2-({(4S,5R)-5-[3,5-bis(trifluoromethyl)phenyl]-4-methyl-2-oxo-1,3-oxazolidin-3-yl}methyl)pyridin-3-yl](ethyl)amino]methyl}cyclohexyl)acetate (8.0 mg, 0.0127 mmol) in EtOH (0.8 mL) and water (0.6 mL) at room temperature. A few extra drops of EtOH were added to re-dissolve the slight precipitate formed. After 7 h the reaction was acidified with 1 N HCl (5 mL) and extracted with EtOAc (20 mL). The pH was adjusted to 4-5 with 7.5 N aqueous KOH and the mixture was extracted with EtOAc (2×20 mL). The combined extracts were dried (Na₂SO₄) and concentrated in vacuo to afford the crude product. This was purified by flash chromatography (Si, 12×160 mm, 1% AcOH, 0-50% EtOAc in hexanes gradient) to afford (trans)-4-{[[2-({(4S,5R)-5-[3,5-bis(trifluoromethyl)phenyl]-4-methyl-2-oxo-1,3-oxazolidin-3-yl}methyl)pyridin-3-yl](ethyl)amino]methyl}cyclohexyl)acetic acid. $R_f$=0.22 (1% AcOH, 1:2 EtOAc/hexanes). LCMS calc.=602.3; found=602.3 $(M+1)^+$. ¹H NMR (600 MHz, CDCl₃): δ 8.34 (d, J=3.8 Hz, 1 H); 7.86 (s, 1 H); 7.80 (s, 2 H); 7.45 (d, J=7.4 Hz, 1 H); 7.20 (dd, J=4.7, 8.0 Hz, 1 H); 5.79 (d, J=8.4 Hz, 1 H); 4-93 (d, J=16.6 Hz, 1 H); 4.47 (d, J=16.6 Hz, 1 H); 4.34-4.28 (m, 1 H); 2.99-2.89 (m, 2 H); 2.83-2.75 (m, 2 H); 2.15 (d, J=6.2 Hz, 2 H); 1.82-1.64 (m, 5 H); 1.31 (m, 1 H); 1.25 (s, 2 H); 0-97 (t, J=7.0 Hz, 3 H); 0.91-0.85 (m, 4 H); 0.66 (d, J=6.6 Hz, 3 H).

Example 70

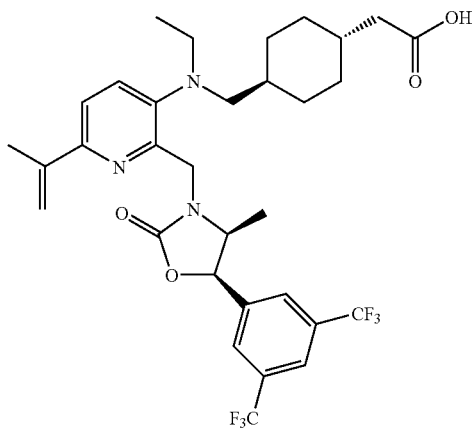

(trans-4-{[[2-({(4S,5R)-5-[3,5-Bis(trifluoromethyl)
phenyl]-4-methyl-2-oxo-1,3-oxazolidin-3-yl}methyl-
6-isopropenylpyridin-3-yl](ethyl)amino]
methyl}cyclohexyl)acetic acid Step A: ethyl (trans-4-{[[2-({(4S,5R)-5-[3,5-bis(trif-
luoromethyl)phenyl]-4-methyl-2-oxo-1,3-oxazolidin-
3-yl}methyl)-1-oxidopyridin-3-yl](ethyl)amino]
methyl}cyclohexyl)acetate 3-Chloroperbenzoic acid (77%, 120 mg, 0.486 mmol) was added to a solution of ethyl (trans-4-{[[2-({(4S,5R)-5-[3,5-bis(trifluoromethyl)phenyl]-4-methyl-2-oxo-1,3-oxazolidin-3-yl}methyl)pyridin-3-yl](ethyl)amino]methyl}cyclohexyl)acetate (152.9 mg, 0.243 mmol) in dry $CH_2Cl_2$ (10 mL) at 0° C. under $N_2$. After 15 min at 0° C., the reaction was stirred at room temperature for 5 h. The reaction mixture was diluted with $CH_2Cl_2$ (20 mL) and washed with saturated $Na_2SO_3$ (10 mL) and saturated $K_2CO_3$ (2×20 mL). The organic layers were dried ($Na_2SO_4$) and concentrated in vacuo to afford ethyl (trans-4-{[[2-({(4S,5R)-5-[3,5-bis(trif-luoromethyl)phenyl]-4-methyl-2-oxo-1,3-oxazolidin-3-yl}methyl)-1-oxidopyridin-3-yl](ethyl)amino]methyl}cyclohexyl)acetate. LCMS calc.=646.3; found=646.3 (M+1)$^+$.

Step B: ethyl (trans-4-{[[2-({(4S,5R)-5-[3,5-bis(trif-
luoromethyl)phenyl]-4-methyl-2-oxo-1,3-oxazolidin-
3-yl}methyl)-6-chloropyridin-3-yl](ethyl)amino]
methyl}cyclohexyl)acetate Triphosgene (360 mg, 1.21 mmol) and diisopropylamine (123 mg, 170 μL, 1.21 mol) were added successively to a stirred solution of ethyl (trans-4-{[[2-({(4S,5R)-5-[3,5-bis(trifluoromethyl)phenyl]-4-methyl-2-oxo-1,3-oxazolidin-3-yl}methyl)-1-oxidopyridin-3-yl](ethyl)amino]methyl}cyclohexyl)acetate (156.6 mg, 0.243 mmol) in dry $CH_2Cl_2$ (9 mL) at –20° C. under $N_2$. The reaction was stirred at room temperature for 6 h. Additional triphosgene (360 mg, 1.21 mmol) and diisopropylamine (123 mg, 170 μL, 1.21 mmol) were added successively and the reaction was stirred at room temperature overnight. The reaction was diluted with saturated $NaHCO_3$ (10 mL) and extracted with $CH_2Cl_2$ (3×20 mL). The combined extracts were dried ($Na_2SO_4$) and concentrated in vacuo to give the crude product. This was purified by flash chromatography (Si, 25×160 mm, 0-60% EtOAc in hexanes gradient) to afford ethyl (trans-4-{[[2-({(4S,5R)-5-[3,5-bis(trifluoromethyl)phenyl]-4-methyl-2-oxo-1,3-oxazolidin-3-yl}methyl)-6-chloropyridin-3-yl](ethyl)amino]methyl}cyclohexyl)acetate. $R_f$=0.32 (20% EtOAc/hexanes). LCMS calc.=664.2; found=664.4 (M+1)$^+$. $^1$H NMR (500 MHz, CDCl$_3$): δ 7.87 (s, 1 H); 7.81 (s, 2 H); 7.41 (d, J=8.4 Hz, 1 H); 7.19 (d, J=8.4 Hz, 1 H); 5.83 (d, J=8.4 Hz, 1 H); 4.97 (d, J=16.9 Hz, 1 H); 4.47-4.43 (m, 1 H); 4.29 (d, J=16.9 Hz, 1 H); 4.12-4.06 (m, 2 H); 2.98-2.88 (m, 2 H); 2.81-2.74 (m, 2H); 2.13 (d, J=6.8 Hz, 2 H); 1.84-1.68 (m, 5 H); 1.36-1.24 (m, 1 H); 1.22 (t, J=7.1 Hz, 3 H); 0.99 (t, J=7.0 Hz, 3 H); 0.95-0.81 (m, 4 H); 0.73 (d, J=6.6 Hz, 3 H).

Step C: ethyl (trans-4-{[[2-({(4S,5R)-5-[3,5-bis(trif-
luoromethyl)phenyl]-4-methyl-2-oxo-1,3-oxazolidin-
3-yl}methyl)-6-isopronenylpyridin-3-yl](ethyl)
amino]methyl}cyclohexyl)acetate A mixture of ethyl (trans-4-{[[2-({(4S,5R)-5-[3,5-bis(trifluoromethyl)phenyl]-4-methyl-2-oxo-1,3-oxazolidin-3-yl}methyl)-6-chloropyridin-3-yl](ethyl)amino]methyl}cyclohexyl)acetate, cyclopropylboronic acid and 1,1'-bis(di-t-butylphosphinoferrocene) palladium dichloride in 1N aqueous potassium carbonate and THF was heated at 85° C. in a sealed tube overnight. The reaction was diluted with water (10 mL) and extracted with EtOAc (3×20 mL). The combined extracts were dried ($Na_2SO_4$) and concentrated in vacuo to give the crude product. This was purified by flash chromatography (Si, 12×160 mm, 0-30% EtOAc in hexanes gradient) to afford ethyl (trans-4-{[[2-({(4S,5R)-5-[3,5-bis(trifluoromethyl)phenyl]-4-methyl-2-oxo-1,3-oxazolidin-3-yl}methyl)-6-isopropenylpyridin-3-yl](ethyl)amino]methyl}cyclohexyl)acetate. $R_f$=0.44 (20% EtOAc/hexanes). LCMS calc.=670.3; found=670.4 (M+1)$^+$. $^1$H NMR (600 MHz, CDCl$_3$): δ 7.87 (s, 1 H); 7.78 (s, 2 H); 7.40 (s, 2 H); 5.85 (s, 1 H); 5.75 (d, J=8.6 Hz, 1 H); 5.25 (s, 1 H); 4.96 (d, J=16.7 Hz, 1 H); 4.42-4.36 (m, 2 H); 4.08 (q, J=7.1 Hz, 2 H); 2.98-2.92 (m, 2 H); 2.85 (dd, J=6.5, 13.0 Hz, 1 H); 2.76 (dd, J=7.5, 13.0 Hz, 1H); 2.20 (s, 3 H); 2.12 (d, J=6.8 Hz, 2 H); 1.83-1.65 (m, 5 H); 1.36-1.30 (m, 1 H); 1.22 (t, J=7.1 Hz, 3 H); 0.99 (t, J=7.0 Hz, 3 H); 0.95-0.83 (m, 4 H); 0.72 (d, J=6.7 Hz, 3 H).

Stet D: (trans-4-{[[2-({(4S,5R)-5-[3,5-bis(trifluo-
romethyl)phenyl]4-methyl-2-oxo-1,3-oxazolidin-3-
yl}methyl)-6-isopropenylpyridin-3-yl](ethyl)amino]
methyl}cyclohexyl)acetic acid Aqueous potassium hydroxide (4N, 100 μL) was added to a stirred solution of ethyl (trans-4-{[[2-({(4S,5R)-5-[3,5-bis(trifluoromethyl)phenyl]-4-methyl-2-oxo-1,3-oxazolidin-3-yl}methyl)-6-isopropenylpyridin-3-yl](ethyl)amino]methyl}cyclohexyl)acetate (7.3 mg, 0.0109 mmol) in EtOH (0.9 mL) and water (0.35 mL) at room temperature. After 8 h the reaction was acidified to pH 5 with 1 N HCl and then diluted with brine (10 mL). The mixture was extracted with EtOAc (3×20 mL) and the combined extracts were dried ($Na_2SO_4$) and concentrated in vacuo to afford the crude product. This was purified by flash chromatography (Si, 12×160 mm, 1% AcOH, 0-65% EtOAc in hexanes gradient) to afford (trans)-4-{[[2-({(4S,5R)-5-[3,5-bis(trifluoromethyl)phe-nyl]-4-methyl-2-oxo-1,3-oxazolidin-3-yl}methyl)pyridin-3- yl](ethyl)amino]methyl}cyclohexyl)acetic acid. $R_f$=0.59 (1% AcOH, 1:2 EtOAc/hexanes). LCMS calc.=642.3; found=642.2 (M+1)$^+$. $^1$H NMR (500 MHz, CDCl$_3$): δ 7.87 (s, 1H); 7.78 (s, 2 H); 7.40 (s, 2 H); 5.85 (s, 1 H); 5.75 (d, J=8.6 Hz, 1 H); 5.25 (s, 1 H); 4.97 (d, J=16.7 Hz, 1 H); 4.43-4.35 (m, 2 H); 2.98-2.90 (m, 2 H); 2.84 (dd, J=8.5, 12.9 Hz, 1 H); 2.76 (dd, J=7.4, 12.9 Hz, 1 H); 2.20 (br s, 5 H); 1.80-1.64 (m, 5 H); 1.35-1.24 (m, 1 H); 0.99 (t, J=7.0 Hz, 3 H); 0.95-0.83 (m, 4 H); 0.72 (d, J=6.6 Hz, 3 H).

Example 71

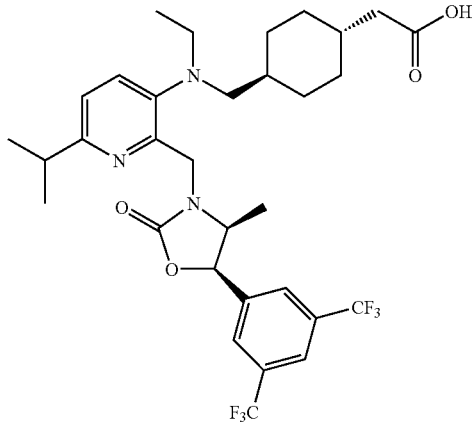

(trans-4-{[[2-({(4S,5R)-5-[3,5-Bis(trifluoromethyl)phenyl]-4-methyl-2-oxo-1,3-oxazolidin-3-yl}methyl)-6-isopropylpyridin-3-yl](ethyl)amino]methyl}cyclohexyl)acetic acid Step A: ethyl (trans-4-{[[2-({(4S,5R)-5-[3,5-bis(trifluoromethyl)phenyl]-4-methyl-2-oxo-1,3-oxazolidin-3-yl}methyl)-6-isopropylpyridin-3-yl](ethyl)amino]methyl}cyclohexyl)acetate A suspension of 10% palladium on carbon (2.0 mg) in a solution of ethyl (trans-4-{[[2-({(4S,5R)-5-[3,5-bis(trifluoromethyl)phenyl]-4-methyl-2-oxo-1,3-oxazolidin-3-yl}methyl)-6-isopropenylpyridin-3-yl](ethyl)amino]methyl}cyclohexyl)acetate (19.0 mg, 0.0284 mmol) in EtOAc (5 mL) was stirred under H$_2$ (double balloon pressure) for 4 h. The reaction mixture was filtered through a plug of Celite and the filtrate was concentrated in vacuo to afford ethyl (trans-4-{[[2-({(4S,5R)-5-[3,5-bis(trifluoromethyl)phenyl]-4-methyl-2-oxo-1,3-oxazolidin-3-yl}methyl)-6-isopropylpyridin-3-yl](ethyl)amino]methyl}cyclohexyl)acetate as a colorless oil. LCMS calc.=672.3; found=672.3 (M+1)$^+$. $^1$H NMR (600 MHz, CDCl$_3$): δ 7.87 (s, 1 H); 7.78 (s, 2 H); 7.36 (d, J=7.6 Hz, 1 H); 7.03 (d, J=7.8 Hz, 1 H); 5.77 (d, J=8.2 Hz, 1 H); 4.95 (d, J=16.6 Hz, 1 H); 4.41-4.35 (m, 2 H); 4.08 (q, J—7.1 Hz, 2 H); 3.01 (s, 1 H); 2.90 (s, 2 H); 2.79-2.71 (m, 2 H); 2.12 (d, J=6.5 Hz, 2 H); 1.84-1.65 (m, 5H); 1.30-1.20 (m, 10 H); 0.98-0.86 (m, 7 H); 0.71 (d, J=6.3 Hz, 3 H).

Step B: (trans-4-{[[2-({(4S,5SR)-5-[3,5-bis(trifluoromethyl)phenyl]-4-methyl-2-oxo-1,3-oxazolidin-3-yl}methyl)-6-isopropylpyridin-3-yl](ethyl)amino]methyl}cyclohexyl)acetic acid Aqueous potassium hydroxide (4N, 200 μL) was added to a stirred solution of ethyl (trans-4-{[[2-({(4S,5R)-5-[3,5-bis(trifluoromethyl)phenyl]-4-methyl-2-oxo-1,3-oxazolidin-3-yl}methyl)-6-isopropenylpyridin-3-yl](ethyl)amino]methyl}cyclohexyl)acetate (7.3 mg, 0.0109 mmol) in EtOH (2.8 mL) and water (0.65 mL) at room temperature. After 8 h the reaction was acidified to pH 5 with 1 N HCl and then diluted with brine (10 mL). The mixture was extracted with EtOAc (3×20 mL) and the combined extracts were dried (Na$_2$SO$_4$) and concentrated in vacuo to afford the crude product. This was purified by flash chromatography (Si, 12×160 mm, 1% AcOH, 0-65% EtOAc in hexanes gradient) to afford (trans)-4-{[[2-({(4S,5R)-5-[3,5-bis(trifluoromethyl)phenyl]-4-methyl-2-oxo-1,3-oxazolidin-3-yl}methyl)pyridin-3-yl](ethyl)amino]methyl}cyclohexyl)acetic acid $R_f$=0.44 (1% AcOH, 1:2 EtOAc/hexanes). LCMS calc.=644.3; found=644.2 (M+1)$^+$. $^1$H NMR (600 MHz, CDCl$_3$): δ 7.87 (s, 1H); 7.78 (s, 2 H); 7.36 (d, J=8.3 Hz, 1 H); 7.03 (d, J=8.3 Hz, 1 H); 5.77 (d, J=8.6 Hz, 1 H); 4.95 (d, J=16.7 Hz, 1 H); 4.42-4.36 (m, 2 H); 3.04-2.98 (m, 1 H); 2.95-2.83 (m, 2 H); 2.78-2.72 (m, 2 H); 2.16 (br s, 2 H); 1.83-1.65 (m, 5 H); 1.33-1.26 (m, 7 H); 0.96 (t, J=7.1 Hz, 3 H); 0.94-0.86 (m, 4 H); 0.71 (d, J=6.6 Hz, 3 H).

The following compounds were synthesized using methods analogous to those described in Example 70 from the aryl chloride described in Example 70, Step B and the corresponding alkyl boronic acid.

| EXAMPLE | MOLECULAR STRUCTURE | LCMS (M + 1)$^+$ |
|---|---|---|
| 72 | 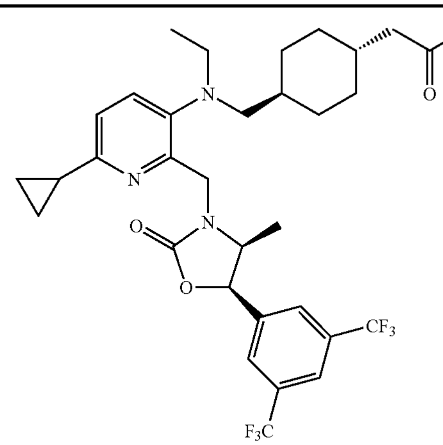 | 642.3 |

Example 73

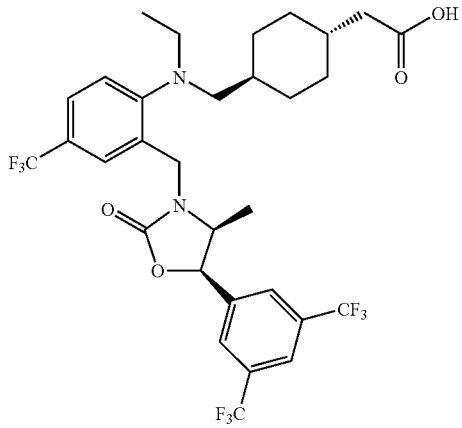

(trans-4-{[[2-({(4S,5R)-5-[3,5-bis(trifluoromethyl)
phenyl]-4-methyl-2-oxo-1,3-oxazolidin-3-
yl}methyl)-4-(trifluoromethyl)phenyl](ethyl)amino]
methyl}cyclohexyl)acetic acid Step A: ethyl [trans-4-({ethyl[2-formyl-4-(trifluoromethyl)phenyl]amino}methyl)cyclohexyl]acetate A stirred mixture of ethyl{trans-4-[(ethylamino)methyl]cyclohexyl}acetate (Intermediate 7; 130 mg; 0.57 mmol), 2-fluoro-5-(trifluoromethyl)benzaldehyde (100 mg; 0.52 mmol) and potassium carbonate (215 mg; 1.56 mmol) in toluene (4 mL) was heated at reflux for 14 h. The reaction was washed with $H_2O$ and sat. $KHSO_4$ (10 mL each) and the aqueous layers were re-extracted with toluene (10 mL). The combined organic layers were washed with brine (10 mL), dried ($MgSO_4$), filtered and concentrated in vacuo to afford ethyl [trans-4-({ethyl[2-formyl-4-(trifluoromethyl)phenyl]amino}methyl)cyclohexyl]acetate as a yellow oil. LCMS=400.2 $(M+1)^+$.

Step B: ethyl [trans-4-({ethyl[2-(hydroxymethyl)-4-(trifluoromethyl)phenyl]amino}methyl)cyclohexyl]acetate To a stirred solution of ethyl [trans-4-({ethyl[2-formyl-4-(trifluoromethyl)phenyl]amino}methyl)cyclohexyl]acetate (Step A; 153 mg; 0.38 mmol) in EtOH (1 mL) was added sodium borohydride (7.3 mg; 0.19 mmol). The reaction stirred at room temperature for 1 h and was concentrated in vacuo. The residue was redissolved in EtOAc (10 mL) and washed with sat. $NH_4Cl$ (10 mL). The aqueous layer was re-extracted with EtOAc (2×10 mL) and the combined organic layers were washed with $H_2O$ and brine (10 mL each), dried ($MgSO_4$), filtered and concentrated in vacuo. The residue was purified by flash silica gel chromatography (0-25% EtOAc/hexanes gradient) to afford ethyl [trans-4-({ethyl[2-(hydroxymethyl)-4-(trifluoromethyl)phenyl]amino}methyl)cyclohexyl]acetate as a yellow oil. LCMS=402.2 $(M+1)^+$. $^1$H NMR ($CDCl_3$, 500 MHz): δ 7.56-7.54 (m, 2 H), 7.29-7.26 (m, 1 H), 4.85 (s, 2 H), 4.13 (q, J=7.1 Hz, 2 H), 3.10-3.02 (m, 2 H), 2.91-2.85 (m, 2 H), 2.17 (d, J=6.9 Hz, 2 H), 1.84-1.70 (m, 4 H), 1.57-1.44 (m, 2 H), 1.39-1.31 (m, 1 H), 1.26 (t, J=7.1 Hz, 3 H), 1.08-1.04 (m, 3 H), 1.01-0.93 (m, 3 H).

Step C: ethyl (trans-4-{[[2-({(4S,5R)-5-[3,5-bis(trifluoromethyl)phenyl]-4-methyl-2-oxo-1,3-oxazolidin-3-yl}methyl)-4-(trifluoromethyl)phenyl](ethyl)amino]methyl}cyclohexyl)acetate A solution of ethyl [trans-4-({ethyl[2-(hydroxymethyl)-4-(trifluoromethyl)phenyl]amino}methyl)cyclohexyl]acetate (Step B; 60 mg; 0.149 mmol) in toluene (1 mL) was added dropwise to a stirred solution of thionyl chloride (12.3 µL; 0.169 mmol) in toluene (300 µL) at 0° C. The reaction stirred at room temperature for 1.5 h. Pyridine (27 mL) was added and the reaction was partitioned between toluene (10 mL) and $H_2O$ (10 mL). The aqueous layer was re-extracted with toluene (10 mL) and the combined organic layers were washed with brine (10 mL), dried ($Na_2SO_4$), filtered and concentrated in vacuo. The residue was dissolved in DMF (1 mL) and (4S,5R)-5-[3,5-bis(trifluoromethyl)phenyl]-4-methyl-1,3-oxazolidin-2-one (intermediate 17; 56 mg; 0.179 mmol) and potassium tert-butoxide (23.5 mg; 0.209 mmol) were added successively. The reaction stirred for 72 h and was quenched with sat. $NH_4Cl$. The reaction was partitioned between sat. $NH_4Cl$ (10 mL) and EtOAc (10 mL). The aqueous layer was re-extracted with EtOAc (3×10 mL) and the combined organic layers were washed with brine (10 mL), dried ($Na_2SO_4$), filtered and concentrated in vacuo. The residue was purified by flash silica gel chromatography (0-20% EtOAc/hexanes gradient) and chiral HPLC (1.5% IPA/heptane; ChiralPak IA column) to afford ethyl (trans-4-{[[2-({(4S,5R)-5-[3,5-bis(trifluoromethyl)phenyl]-4-methyl-2-oxo-1,3-oxazolidin-3-yl}methyl)-4-(trifluoromethyl)phenyl](ethyl)amino]methyl}cyclohexyl)acetate as a clear glass. LCMS=697.3 $(M+1)^+$. $^1$H NMR ($CDCl_3$, 500 MHz): δ 7.92 (s, 1 H), 7.81 (s, 2 H), 7.65 (s, 1 H), 7.58 (d, J=8.4 Hz, 1H), 7.30-7.27 (m, 1 H), 5.78 (d, J=8.1 Hz, 1 H), 4.88 (d, J=16.5 Hz, 1 H), 4.74-4.69 (m, 1 H), 4.11 (q, J=7.1 Hz, 2 H), 3.17-3.10 (m, 2 H), 3.05-2.97 (m, 2 H), 2.15 (d, J=6.8 Hz, 2 H), 1.80-1.68 (m, 4 H), 1.66-1.50 (m, 1 H), 1.46-1.39 (m, 1 H), 1.25 (t, J=7.1 Hz, 3 H), 1.07 (t, J=7.0 Hz, 3 H), 1.03-0.85 (m, 4H), 0.71 (d, J=6.6 Hz, 3 H).

Step D: (trans-4-{[[2-({(4S,5R)-5-[3,5-bis(trifluoromethyl)phenyl]-4-methyl-2-oxo-1,3-oxazolidin-3-yl}methyl)-4-(trifluoromethyl)phenyl](ethyl)amino]methyl}cyclohexyl acetic acid To a stirred solution of ethyl (trans-4-{[[2-({(4S,5R)-5-[3,5-bis(trifluoromethyl)phenyl]-4-methyl-2-oxo-1,3-oxazolidin-3-yl}methyl)-4-(trifluoromethyl)phenyl](ethyl)amino]methyl}cyclohexyl)acetate (Step C; 29 mg; 0.042 mmol) in EtOH (2 mL) was added 4 M KOH (400 µL). The reaction was stirred for 90 min, neutralized with aq. citric acid and partitioned between EtOAc (10 mL) and $H_2O$ (10 mL). The aqueous layer was re-extracted with EtOAc (10 mL) and the combined organic layers were washed with brine (10 mL), dried (Na2SO4), filtered, and concentrated in vacuo. The residue was purified by preparatory silica gel chromatography (eluted with 2:1 Hexanes:EtOAc+1% AcOH) to afford (trans-4-{[[2-({(4S,5R)-5-[3,5-bis(trifluoromethyl)phenyl]-4-methyl-2-oxo-1,3-oxazolidin-3-yl}methyl)-4-(trifluoromethyl)phenyl](ethyl)amino]methyl}cyclohexyl)acetic acid as a clear glass. LCMS=669.2 $(M+1)^+$. $^1$H NMR ($CDCl_3$, 500 MHz): δ 7.91 (s, 1 H), 7.80 (s, 2 H), 7.57 (s, 1 H), 7.52 (d, J=8.3 Hz, 1H), 7.22 (d, J=8.5 Hz, 1 H), 5.77 (d, J=8.0 Hz, 1 H), 4.79 (d, J=16.2 Hz, 1 H), 4.57 (d, J=16.2 Hz, 1H), 4.02-3.99 (m, 1 H), 3.05-2.95 (m, 2 H), 2.93-2.84 (m, 2 H), 2-19 (d, J=6.9 Hz, 2

H), 1.82-1.75 (m, 4H), 1.74-1.68 (m, 1 H), 1.43-1.37 (m, 1 H), 1.01 (t, J=7.0 Hz, 3 H), 0.99-0.88 (m, 4 H), 0.66 (d, J=6.4 Hz, 3 H).

Example 74

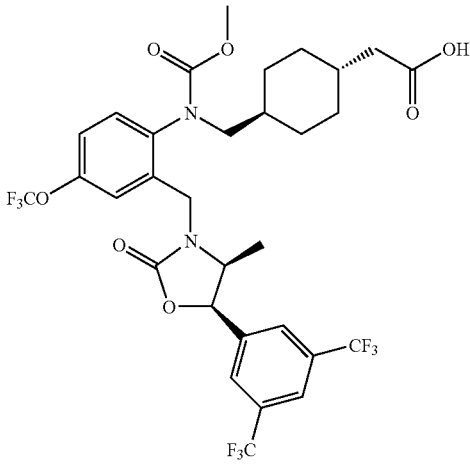

(trans-4-{[[2-({(4S,5R)-5-[3,5-bis(trifluoromethyl)phenyl]-4-methyl-2-oxo-1,3-oxazolidin-3-yl}methyl)-4-(trifluoromethoxy)phenyl](methoxycarbonyl)amino]methyl}cyclohexyl)acetic acid Step A: ethyl [trans-4-({[2-({(4S,5R)-5-[3,5-bis(trifluoromethyl)phenyl]-4-methyl-2-oxo-1,3-oxazolidin-3-yl}methyl)-4-(trifluoromethoxy)phenyl]amino}methyl)cyclohexyl]acetate A stirred solution of (4S,5R)-3-[2-amino-5-(trifluoromethoxy)benzyl]-5-[3,5-bis(trifluoromethyl)phenyl]-4-methyl-1,3-oxazolidin-2-one (Intermediate 16; 820 mg; 1.63 mmol) and ethyl (trans-4-formylcyclohexyl)acetate (Intermediate 14; 270 mg; 1.36 mmol) in toluene (8 mL) was heated at reflux for 3 h. The reaction was concentrated in vacuo and redissolved in EtOH (8 mL). Sodium borohydride (103 mg; 2.72 mmol) was added and the reaction stirred at room temperature for 14 h. The reaction was quenched with sat. NH$_4$Cl and partitioned between EtOAc (25 mL) and H$_2$O (25 mL). The aqueous layer was re-extracted with EtOAc (3×25 mL) and the combined organic layers were washed with brine (25 mL), dried (Na$_2$SO$_4$), filtered and concentrated in vacuo. The residue was purified by flash silica gel chromatography (0-25% EtOAc/hexanes gradient) to afford ethyl [trans-4-({[2-({(4S,5R)-5-[3,5-bis(trifluoromethyl)phenyl]-4-methyl-2-oxo-1,3-oxazolidin-3-yl}methyl)-4-(trifluoromethoxy)phenyl]amino}methyl)cyclohexyl]acetate as a yellow gum. LCMS=685.1 (M+1)$^+$. $^1$H NMR (CDCl$_3$, 500 MHz): δ 7.89 (s, 1 H), 7.73 (s, 2 H), 7.13 (d, J=8.7 Hz, 1 H), 6.92 (d, J=2.3 Hz, 1 H), 6.72 (d, J=9.0 Hz, 1 H), 5.66 (d, J=8.2 Hz, 1 H), 4.74 (d, J=15.6 Hz, 1 H), 4.14-4.02 (m, 4 H), 3.05-2.97 (m, 2 H), 2.19 (d, J=6.9 Hz, 2 H), 1.96-1.90 (m, 2 H), 1.85-1.78 (m, 2 H), 1.71-1.62 (m, 1 H), 1.51-1.39 (m, 2 H), 1.25 (t, J=7.1 Hz, 3 H), 1.12-1.03 (m, 3 H), 0.80 (d, J=6.4 Hz, 3 H).

Step B: ethyl (trans-4-{[[2-({(4S,5R)-5-[3,5-bis(trifluoromethyl)phenyl]-4-methyl-2-oxo-1,3-oxazolidin-3-yl}methyl)-4-(trifluoromethoxy)phenyl](methoxycarbonyl)amino]methyl}cyclohexyl)acetate To a stirred solution of ethyl [trans-4-({[2-({(4S,5R)-5-[3,5-bis(trifluoromethyl)phenyl]-4-methyl-2-oxo-1,3-oxazolidin-3-yl}methyl)-4-(trifluoromethoxy)phenyl]amino}methyl)cyclohexyl]acetate (Step A; 50 mg; 0.73 mmol) in CH$_2$Cl$_2$ (3 mL) was added methyl chloroformate (50 μL) followed by diisopropylethylamine (102 μL; 0.585 mmol). The reaction stirred at 40° C. for 24 h. The reaction was diluted with EtOAc (25 mL) and washed successively with sat. NaHCO$_3$, brine, 1N HCl and brine (15 mL each), dried (MgSO$_4$), filtered and concentrated in vacuo. The residue was purified by flash silica gel chromatography (0-25% EtOAc/hexanes gradient) and chiral HPLC (4% IPA/heptane; AD column) to afford ethyl (trans-4-{[[2-({(4S,5R)-5-[3,5-bis(trifluoromethyl)phenyl]-4-methyl-2-oxo-1,3-oxazolidin-3-yl}methyl)-4-(trifluoromethoxy)phenyl](methoxycarbonyl)amino]methyl}cyclohexyl)acetate as a clear glass. LCMS=743.2 (M+1)$^+$. $^1$H NMR (CDCl$_3$, 500 MHz): δ 7.90-7.85 (m, 1 H), 7.78 (s, 1 H), 7.75 (s, 1 H), 7.27-7.17 (m, 3 H), 5.71 (d, J=8.0 Hz, 1 H), 5.00-4.54 (m, 1 H), 4.12 (q, J=7.1 Hz, 2 H), 4.10-4.02 (m, 1 H), 3.98-3.82 (m, 2 H), 3.80-3.58 (m, 3 H), 3.14-3.00 (m, 1 H), 2.17 (d, J=6.9 Hz, 2 H), 1.87-1.66 (m, 4 H), 1.52-1.41 (m, 2 H), 1.25 (t, J=7.1 Hz, 3 H), 1.13-0.94 (m, 4 H), 0.69 (d, J=6.4 Hz, 3 H).

Step C: (trans-4-{[[2-({(4S,5R)-5-[3,5-bis(trifluoromethyl)phenyl]-4-methyl-2-oxo-1,3-oxazolidin-3-yl}methyl)-4-(trifluoromethoxy)phenyl](methoxycarbonyl)amino]methyl}cyclohexyl)acetic acid To a stirred solution of ethyl (trans-4-f{[[2-({(4S,5R)-5-[3,5-bis(trifluoromethyl)phenyl]-4-methyl-2-oxo-1,3-oxazolidin-3-yl}methyl)-4-(trifluoromethoxy)phenyl](methoxycarbonyl)amino]methyl}cyclohexyl)acetate (Step C; 28 mg; 0.038 mmol) in EtOH (3 mL) was added 4 M KOH (400 μL). The reaction was stirred for 2.5 h, neutralized with aq. citric acid and partitioned between EtOAc (10 mL) and H$_2$O (10 mL). The aqueous layer was re-extracted with EtOAc (10 mL) and the combined organic layers were washed with brine (10 mL), dried (Na$_2$SO$_4$), filtered, and concentrated in vacuo. The residue was purified by preparatory silica gel chromatography (eluted with 2:1 Hexanes:EtOAc+1% AcOH) to afford (trans-4-{[[2-({(4S,5R)-5-[3,5-bis(trifluoromethyl)phenyl]-4-methyl-2-oxo-1,3-oxazolidin-3-yl}methyl)-4-(trifluoromethoxy)phenyl](methoxycarbonyl)amino]methyl}cyclohexyl)acetic acid as a white solid. LCMS=715.1 (M+1)$^+$. $^1$H NMR (CDCl$_3$, 500 MHz): δ 7.92-7.88 (m, 1 H), 7.80 (s, 1 H), 7.77 (s, 1 H), 7.29-7.21 (m, 2 H), 7.19 (s, 1 H), 5.73 (d, J=8.4 Hz, 1 H), 5.02-4.74 (m, 1 H), 4.16-3.61 (m, 6 H), 3.10-3.03 (m, 1 H), 2.27 (d, J=6.9 Hz, 2 H), 1.92-1.72 (m, 4 H), 1.54-1.44 (m, 2 H), 1.18-0.98 (m, 4 H), 0.71 (d, J=6.4 Hz, 3 H).

In a similar manner the following compounds were synthesized:

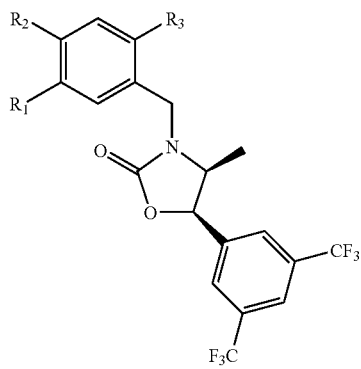
| EXAMPLE | R₁ | R₂ | R₃ | LCMS (M + 1)⁺ |
|---|---|---|---|---|
| 75 | CF₃ | H | | 669.2 |
| 76 | CF₃ | H | | 683.4 |
| 77 | CF₃ | CH₃ | | 697.4 |
| 78 | OCF₃ | H | | 612.9 |
| 79 | OCF₃ | H | | 729.2 |
| 80 | OCF₃ | H | | 694.9 |
| 81 | OCF₃ | H | | 694.9 |

| EXAMPLE | R₁ | R₂ | R₃ | LCMS (M + 1)⁺ |
|---|---|---|---|---|
| 82 | OCF₃ | H | (acetamidomethyl-cyclohexyl-acetic acid) | 699.0 |
| 83 | CF3 | H | (N-ethyl-aminomethyl-cyclohexyl methyl ester) | 669.3 |
| 84 | CF3 | H | (N-ethyl-aminomethyl-cyclohexyl carboxylic acid) | 655.3 |

Example 85

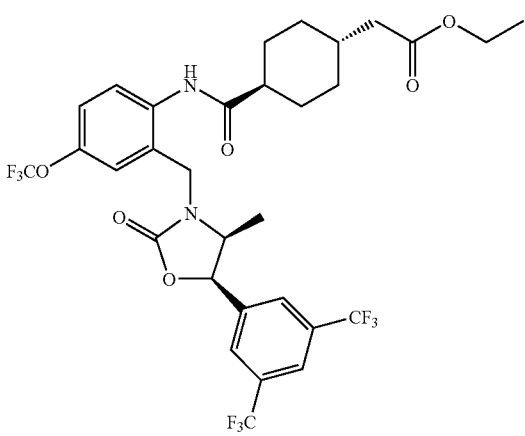

ethyl [trans-4-({[2-({(4S,5R)-5-[3,5-bis(trifluoromethyl)phenyl]-4-methyl-2-oxo-1,3-oxazolidin-3-yl}methyl)-4-(trifluoromethoxy)phenyl]amino}carbonyl)cyclohexyl]acetate A stirred solution of trans-4-(2-ethoxy-2-oxoethyl)-cyclohexanecarboxylic acid (1 g; 4.67 mmol) in anhydrous THF (25 mL) at 0° C. was treated dropwise with oxalyl chloride (1.02 mL; 11.68 mmol) followed by catalytic DMF (50 μL). The reaction was stirred at room temperature for 2 h, concentrated in vacuo, and the residue was redissolved in THF (25 mL). The resultant solution was cooled to 0° C. and treated with (4S,5R)-3-[2-amino-5-(trifluoromethoxy)benzyl]-5-[3,5-bis(trifluoromethyl)phenyl]-4-methyl-1,3-oxazolidin-2-one (2.58 g; 5.14 mmol) and triethylamine (0.716 mL; 5.14 mmol). The reaction was stirred at room temperature for 1 h, quenched with water and partitioned between EtOAc (100 mL) and H₂O (100 mL). The aqueous layer was extracted with EtOAc (3×100 mL) and the combined extracts were washed with brine (100 mL), dried (MgSO₄), filtered and concentrated in vacuo. The residue was purified by flash silica gel chromatography, eluting with EtOAc/hexanes, to afford ethyl [trans-4-({[2-({(4S,5R)-5-[3,5-bis(trifluoromethyl)phenyl]-4-methyl-2-oxo-1,3-oxazolidin-3-yl}methyl)-4-(trifluoromethoxy)phenyl]amino}carbonyl)cyclohexyl]acetate as an off-white solid. LCMS=698.9 (M+1)⁺. ¹H NMR (CDCl₃, 500 MHz): δ 8.94 (s, 1 H), 8.23 (d, J=8.9 Hz, 1 H), 7.92 (s, 1 H), 7.73 (s, 2H), 7.27-7.24 (m, 1 H), 7.02 (s, 1 H), 5.71 (d, J=8.4 Hz, 1 H), 4.78 (d, J=15.5 Hz, 1 H), 4.19-4.12 (m, 3H), 4.07 (d, J=15.6 Hz, 1 H), 2.43-2.37 (m, 1 H), 2.21 (d, J=6.9 Hz, 2 H), 2.07-1.98 (m, 2 H), 1.93-1.83 (m, 3 H), 1.67 (q, J=12.6 Hz, 2 H), 1.26 (t, J=7.2 Hz, 3 H), 1.19-1.11 (m, 2 H), 0.88 (d, J=6.6 Hz, 3 H).

Example 86

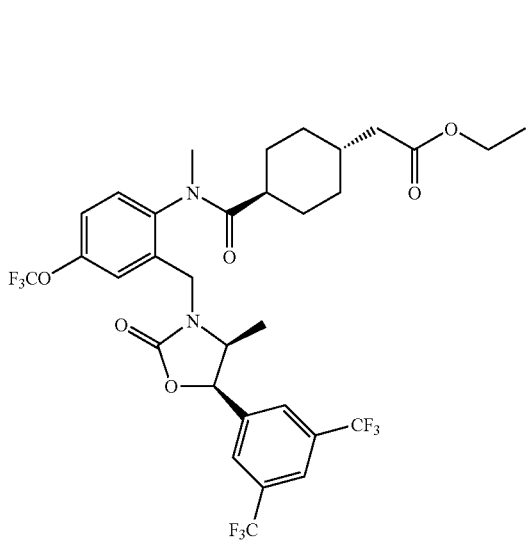

ethyl (trans-4-{[[2-({(4S,5R)-5-[3,5-bis(trifluoromethyl)phenyl]-4-methyl-2-oxo-1,3-oxazolidin-3-yl}methyl)-4-(trifluoromethoxy)phenyl](methyl)amino]carbonyl}cyclohexyl)acetate A stirred solution of ethyl [trans-4-({[2-({(4S,5R)-5-[3,5-bis(trifluoromethyl)phenyl]-4-methyl-2-oxo-1,3-oxazolidin-3-yl}methyl)-4-(trifluoromethoxy)phenyl]amino}carbonyl)cyclohexyl]acetate (500 mg; 0.716 mmol) in anhydrous THF (10 mL) was cooled to 0° C. and treated with sodium hydride (60% in oil; 31.5 mg; 0.788 mmol). The resultant mixture was stirred at 0° C. for 30 min prior to addition of iodomethane (58 µL; 0.931 mmol). The reaction was stirred at room temperature for 14 h and quenched with H$_2$O. The reaction was partitioned between EtOAc (50 mL) and H$_2$O (50 mL) and the aqueous layer was extracted with EtOAc (3×50 mL). The combined extracts were washed with brine (50 mL), dried (MgSO$_4$), filtered and concentrated in vacuo. The residue was purified by flash silica gel chromatography, eluting with EtOAc/hexanes, and by chiral HPLC (chiralPak IA column, 10% $^i$PrOH/heptane) to afford ethyl (trans-4-{[[2-({(4S,5R)-5-[3,5-bis(trifluoromethyl)phenyl]-4-methyl-2-oxo-1,3-oxazolidin-3-yl}methyl)-4-(trifluoromethoxy)phenyl](methyl)amino]carbonyl}cyclohexyl)acetate as a clear oil. LCMS=713.0 (M+1)$^+$. $^1$H NMR (CDCl$_3$, 500 MHz, mixture of atropisomers): δ 7.92 (s, 1 H), 7.80 (s, 1 H), 7.73 (s, 1H), 7.29-7.20 (m, 2 H), 7.17-7.15 (m, 1 H), 5.66 (d, J=8.3 Hz, 1 H), 4.95 (d, J=14.8 Hz, 1 H), 4.22 (d, J=16.7 Hz, 1 H), 4.14-4.06 (m, 2 H), 3.897 (d, J=14.7 Hz, 1 H), 3.39 (s, 3 H), 2.70-2.63 (m, 1 H), 2.22-2.18 (m, 1 H), 2.10-2.07 (m, 1 H), 2.00-1.52 (m, 8 H), 1.27-1.19 (m, 3 H), 1.16-1.08 (m, 1 H), 0.76-0.68 (m, 3 H).

Example 87

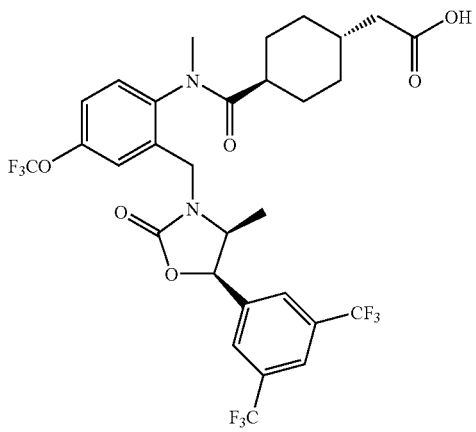

(trans-4-{[[2-({(4S,5R)-5-[3,5-bis(trifluoromethyl)phenyl]-4-methyl-2-oxo-1,3-oxazolidin-3-yl}methyl)-4-(trifluoromethoxy)phenyl](methyl)amino]carbonyl}cyclohexyl)acetic acid A stirred solution of ethyl (trans-4-{[[2-({(4S,5R)-5-[3,5-bis(trifluoromethyl)phenyl]-4-methyl-2-oxo-1,3-oxazolidin-3-yl}methyl)-4-(trifluoromethoxy)phenyl](methyl)amino]carbonyl}cyclohexyl)acetate (100 mg; 0.14 mmol) in EtOH (110 mL) was treated dropwise with 4 M KOH (1 mL). The reaction was stirred at room temperature and quenched with 10% citric acid after 2.5 h. The reaction was partitioned between EtOAc (50 mL) and H$_2$O (50 mL) and the aqueous layer was extracted with EtOAc (3×50 mL). The combined extracts were washed with brine (50 mL), dried (Na$_2$SO$_4$), filtered and concentrated in vacuo. The residue was purified by reverse-phase HPLC and the desired product was lyophilized to afford (trans-4-{[[2-({(4S,5R)-5-[3,5-bis(trifluoromethyl)phenyl]-4-methyl-2-oxo-1,3-oxazolidin-3-yl}methyl)-4-(trifluoromethoxy)phenyl](methyl)amino]carbonyl}cyclohexyl)acetic acid as a white solid. LCMS=685.0 (M+1)$^+$. $^1$H NMR (CDCl$_3$, 500 MHz, mixture of atropisomers): δ 7.92 (s, 1 H), 7.80 (s, 1 H), 7.74 (s, 1 H), 7.29-7.21 (m, 2 H), 7.17-7.15 (m, 1 H), 5.67 (d, J=8.2 Hz, 1 H), 4.96 (d, J=14.7 Hz, 1 H), 4.22 (d, J=16.5 Hz, 1 H), 3.88 (d, J=15.1 Hz, 1 H), 3.41 (s, 3 H), 2.73-2.66 (m, 1 H), 2.28-2.24 (m, 1 H), 2.15-2.12 (m, 1 H), 2.01-1.50 (m, 8 H), 1.18-1.10 (m, 1 H), 0.76-0.68 (m, 3 H).

Example 88

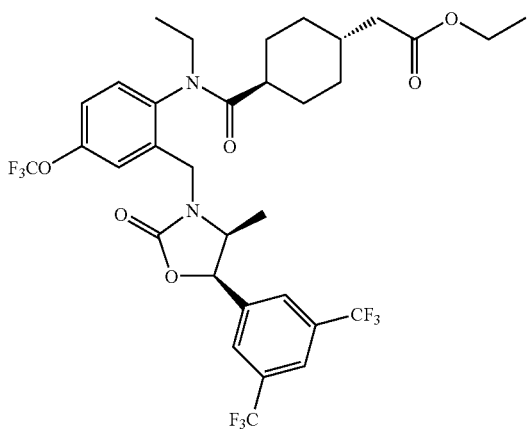

ethyl (trans-4-{[[2-({(4S,5R)-5-[3,5-bis(trifluoromethyl)phenyl]-4-methyl-2-oxo-1,3-oxazolidin-3-yl}methyl)-4-(trifluoromethoxy)phenyl](ethyl)amino]carbonyl}cyclohexyl)acetate Ethyl [trans-4-({[2-({(4S,5R)-5-[3,5-bis(trifluoromethyl)phenyl]-4-methyl-2-oxo-1,3-oxazolidin-3-yl}methyl)-4-(trifluoromethoxy)phenyl]amino}carbonyl)cyclohexyl]acetate (637 mg; 0-913 mmol) was treated with sodium hydride (60% in oil; 40 mg; 1.0 mmol) and iodoethane (110 mL; 1.37 mmol) as described in EXAMPLE 86 to afford ethyl (trans-4-{[[2-({(4S,5R)-5-[3,5-bis(trifluoromethyl)phenyl]-4-methyl-2-oxo-1,3-oxazolidin-3-yl}methyl)-4-(trifluoromethoxy)phenyl](ethyl)amino]carbonyl}cyclohexyl) acetate as a yellow oil. LCMS=727.0 (M+1)$^+$. $^1$H NMR (CDCl$_3$, 500 MHz, mixture of atropisomers): δ 7.92 (s, 1 H), 7.80 (s, 1 H), 7.74 (s, 1 U), 7.28-7.22 (m, 1 H), 7.19-7.16 (m, 1 H), 7.14-7.11 (m, 1 H), 5.66 (d, J=8.0 Hz, 1 H), 4.92 (d, J=14.9 Hz, 1 H), 4.25 (d, J=16.9 Hz, 1 H), 4.23-4.05 (m, 4 H), 3.54-3.46 (m, 1 H), 3.08-3.00 (m, 1 H), 2.66-2.58 (m, 1 H), 2.22-2.18 (m, 1 H), 2.09-2.06 (m, 1 H), 1.92-1.52 (m, 6 H), 1.26-1.12 (m, 7 H), 0.81-0.66 (m, 4 H).

Example 89

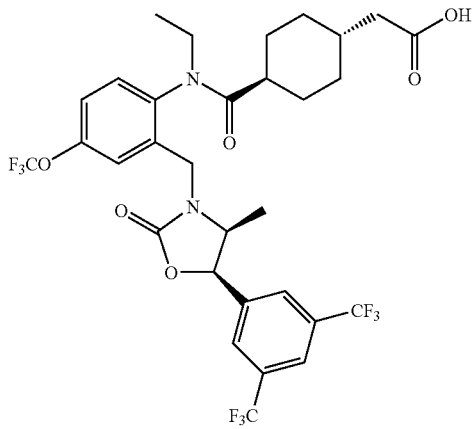

(trans-4-{[[2-({(4S,5R)-5-[3,5-bis(trifluoromethyl)phenyl]-4-methyl-2-oxo-1,3-oxazolidin-3-yl}methyl)-4-(trifluoromethoxy-phenyl](ethyl)amino]carbonyl}cyclohexyl)acetic acid Ethyl (trans-4-{[[2-({(4S,5R)-5-[3,5-bis(trifluoromethyl)phenyl]-4-methyl-2-oxo-1,3-oxazolidin-3-yl}methyl)-4-(trifluoromethoxy)phenyl](ethyl)amino]carbonyl}cyclohexyl)acetate (100 mg; 0.138 mmol) was treated with 4 M KOH (1 mL) as in EXAMPLE 87 to afford (trans-4-{[[2-({(4S,5R)-5-[3,5-bis(trifluoromethyl)phenyl]-4-methyl-2-oxo-1,3-oxazolidin-3-yl}methyl)-4-(trifluoromethoxy)phenyl](ethyl)amino]carbonyl}cyclohexyl)acetic acid as a white solid. LCMS=699.0 (M+1)$^+$. $^1$H NMR (CDCl$_3$, 500 MHz, mixture of atropisomers): δ 7.92 (s, 1 H), 7.80 (s, 1 H), 7.75 (s, 1H), 7.29-7.22 (m, 1 H), 7.19-7.17 (m, 1 H), 7.15-7.11 (m, 1 H), 5.67 (d, J=8.3 Hz, 1 H), 4.93 (d, J=14.9 Hz, 1 H), 4.25-4.10 (m, 2 H), 3.91 (d, J=14.9 Hz, 1 H), 3.54-3.46 (m, 1 H), 3.09-3.01 (m, 1 H), 2.68-2.61 (m, 1 H), 2.27-2.24 (m, 1 H), 2.15-2.11 (m, 1 H), 1.96-1.51 (m, 6 H), 1.26-1.21 (m, 1 H), 1.17-1.12 (m, 3 H), 0.83-0.67 (m, 4 H).

Example 90

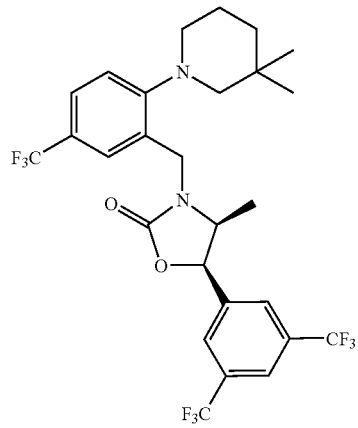

(4S,5R)-5-[3,5-bis(trifluoromethyl)phenyl]-3-[2-(3,3-dimethylpiperidin-1-yl)-5-(trifluoromethyl)benzyl]-4-methyl-1,3-oxazolidin-2-one (4S,5R)-5-[3,5-bis(trifluoromethyl)phenyl]-3-[2-iodo-5-(trifluoromethyl)benzyl]-4-methyl-1,3-oxazolidin-2-one (500 mg, 0.837 mmol), 3,3-dimethylpiperidine (142.5 mg, 1.26 mmol), Bis(tri-t-butylphosphine)palladium (0) (43 mg, 0.084 mmol), cesium carbonate (685 mg, 2.10 mmol) and 1,4-dioxane (5 mL) were sealed in a microwave vessel. The reaction mixture was irradiated by microwave at 170° C. for 30 minutes. Reaction crude was purified by SiO$_2$ to afford (4S,5R)-5-[3,5-bis(trifluoromethyl)phenyl]-3-[2-(3,3-dimethylpiperidin-1-yl)-5-(trifluoromethyl)benzyl]-4-methyl-1,3-oxazolidin-2-one. LCMS calc.=582.19; found=583.44 (M+1)$^+$. $^1$H NMR signals are doubled because of atropoisomerism $^1$H NMR (CDCl$_3$, 500 MHz) δ 7.88 (s, 1H), 7.77 (s, 2H), 7.58 (s, 1H), 7.52 (d, J=8.0 Hz, 1H), 7.16 (d, J=8.5 Hz, 1H), 5.72 (d, J=8.0 Hz, 1H), 4.76 (d, J=16 Hz, 1H), 4.57 (d, J=15.5 Hz, 1H), 3.94-3.87 (m, 1H), 2.84 (br s, 1H), 2.68 (br s, 1H), 2.63 (d, J=11 Hz, 1H), 2.52 (d, J=11 Hz, 1H), 1.81 (br s, 1H), 1.71 (br s, 1H), 1.38 (br s, 2H), 1.06 (s, 3H), 0.99 (s, 3H), 0.67, 0.66 (s, 3H).

The compounds in the following table were prepared as described in the preceding example.

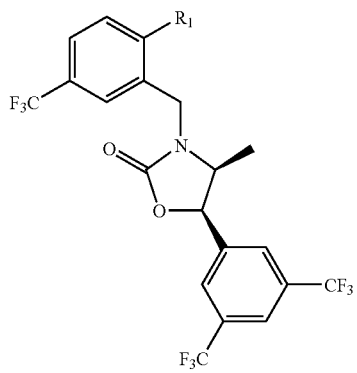

| Example | R¹ | LC/MS Data |
|---|---|---|
| 91 | 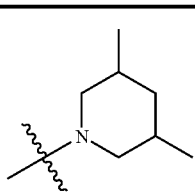 | 583.54 |
| 92 | 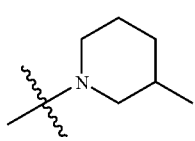 | 569.41 |
| 93 | 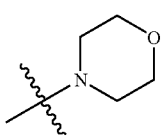 | 557.13 |
| 94 | 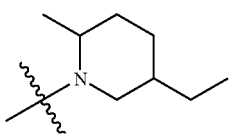 | 596.24 |
| 95 | 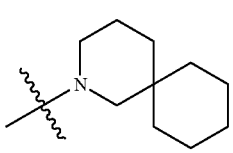 | 623.39 |

Example 96

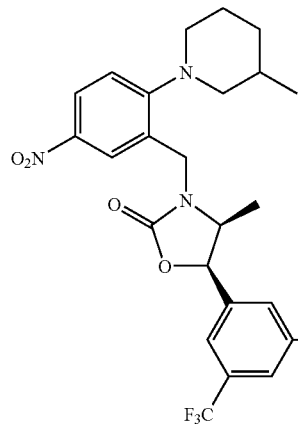

(4S,5R)-5-[3,5-bis(trifluoromethyl)phenyl]-4-methyl-3-[2-(3-methylpiperidin-1-yl)-5-nitrobenzyl]-1,3-oxazolidin-2-one (4S,5R)-5-[3,5-bis(trifluoromethyl)phenyl]-3-(2-bromo-5-nitrobenzyl)-4-methyl-1,3-oxazolidin-2-one (42 mg, 0.083 mmol), 3-methylpiperidine (13 mg, 0.126 mmol), palladium (II) acetate (1.0 mg, 5%), (±)-2,2'-bis(diphenylphosphino)-1,1'-binaphthalene (2-6 mg, 7.5%), cesium carbonate (55 mg, 0.17 mmol) and THF (1 mL) were sealed in a microwave vessel. The reaction mixture was irradiated by microwave at 150° C. for 1 hour. Reaction crude was purified by SiO₂ to afford (4S,5R)-5-[3,5-bis(trifluoromethyl)phenyl]-4-methyl-3-[2-(3-methylpiperidin-1-yl)-5-nitrobenzyl]-1,3-oxazolidin-2-one. LCMS calc.=546.17; found=546.23 (M+1)⁺. ¹H NMR signals are doubled because of atropoisomerism ¹H NMR (CDCl₃, 500 MHz) δ 8.22 (d, J=2.5 Hz, 1H), 8.16 (d, J=3 Hz, 0.5H), 8.14 (d, J=2.5 Hz, 0.5H), 7.89 (s, 1H), 7.78 (s, 2H), 7.14 (d, J=4 Hz, 0.5H), 7.12 (d, J=4.0 Hz, 0.5H), 5.76 (d, J=8 Hz, 1H), 4.84 (d, J=4.5 Hz, 0.5H), 4.81 (d, J=4.5 Hz, 0.5H), 4.40 (d, J=3.5 Hz, 0.5H), 4.36 (d, J=3.5 Hz, 0.5H), 3.87-3.83 (m, 1H), 7.14 (s, 1H), 3.09 (s, 2H), 3.02 (d, J=12.5 Hz, 1H), 2.84 (t, J=10 Hz, 1H), 2.60 (t, J=12.5 Hz, 1H), 2.54 (t, J=11 Hz, 0.5H), 2.33 (t, J=11 Hz, 1H), 1.16-1.07 (m, 1H), 0.96 (d, J=6.5 Hz, 0.5H), 0.94 (d, J=6.5 Hz, 1.5H), 0.70 (s, 1.5H), 0.69 (s, 1.5H).

The compounds in the following table were prepared as described in the preceding example.

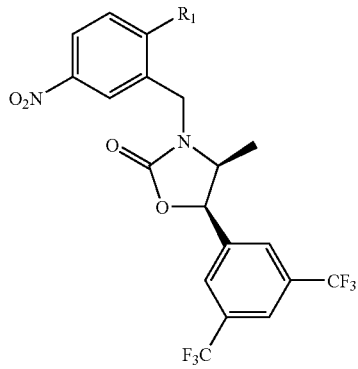

| Example | R¹ | LC/MS Data |
|---|---|---|
| 97 | 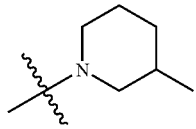 | 546.23 |
| 98 | 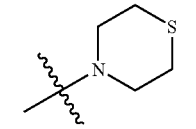 | 550.12 |
| 99 | 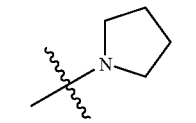 | 518.13 |
| 100 | 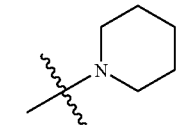 | 532.39 |
| 101 | 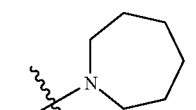 | 546.44 |
| 102 | 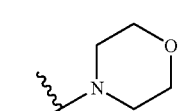 | 534.19 |
| 103 | 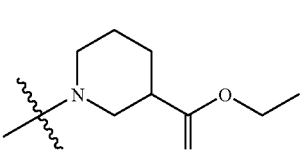 | 604.26 |
| 104 | 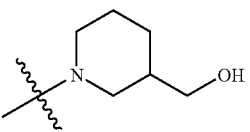 | 562.24 |

-continued

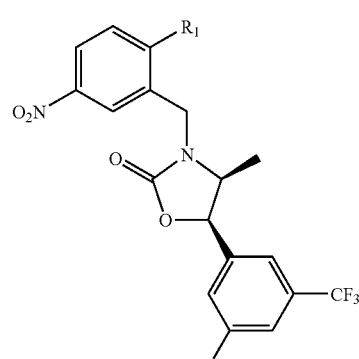

| Example | R¹ | LC/MS Data |
|---|---|---|
| 105 | 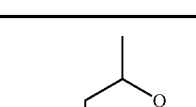 | 562.34 |
| 106 | 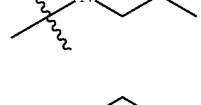 | 547.36 |

What is claimed is:

1. A compound having Formula I, or a pharmaceutically acceptable salt thereof, wherein

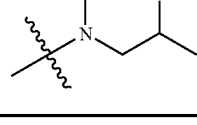

Y is selected from the group consisting of —C(=O)— and —(CRR¹)—;

X is —O—;

Z is —C(=O)—;

R and R¹ are each independently selected from the group consisting of H, —$C_1$-$C_5$ alkyl, and halogen, wherein —$C_1$-$C_5$ alkyl is optionally substituted with 1-11 halogens;

R⁵ is selected from the group consisting of H, —OH, —$C_1$-$C_5$ alkyl, and halogen, wherein —$C_1$-$C_5$ alkyl is optionally substituted with 1-11 halogens;

B and R² are each selected from the group consisting of A¹ and A², wherein A¹ has the structure:

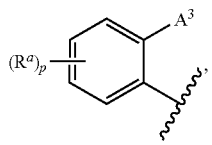

wherein one of the =CH— groups of the phenyl ring of $A^1$ that are optionally unsubstituted may optionally be replaced by =N—, so that $A^1$ comprises a pyridine ring;

Wherein one of B and $R^2$ is $A^1$, and the other of B and $R^2$ is $A^2$, so that the compound of Formula I comprises one group $A^1$ and one group $A^2$;

$A^3$ is —$(CR^{10}R^{11})_q NR^7R^8$;

$A^2$ is phenyl, wherein $A^2$ is optionally substituted with 1-5 substituent groups independently selected from $R^a$;

Each $R^a$ is independently selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —$OC_1$-$C_6$alkyl, —$OC_2$-$C_6$ alkenyl, —$OC_2$-$C_6$ alkynyl, —$OC_3$-$C_8$ cycloalkyl optionally having 1-3 double bonds, —C(=O)$C_1$-$C_6$alkyl, —C(=O)$C_3$-$C_8$ cycloalkyl, —C(=O)H, —$CO_2$H, —$CO_2C_1$-$C_6$alkyl, —C(=O)S$C_1$-$C_6$alkyl, —OH, —$NR^3R^4$, —C(=O)$NR^3R^4$, —$NR^3$C(=O)O$C_1$-$C_6$ alkyl, —$NR^3$C(=O)$NR^3R^4$, —S(O)$_x$$C_1$-$C_6$ alkyl, —S(O)$_y$$NR^3R^4$, —$NR^3$S(O)$_y$$NR^3R^4$, halogen, —CN, —$NO_2$, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which $R^a$ is attached is a carbon atom, wherein said heterocyclic ring is optionally substituted with 1-5 substituent groups independently selected from halogen, —$C_1$-$C_3$ alkyl, and —$OC_1$-$C_3$ alkyl, wherein —$C_1$-$C_3$ alkyl and —$OC_1$-$C_3$ alkyl are optionally substituted with 1-7 halogens;

wherein for compounds in which $R^a$ is selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —$OC_1$-$C_6$alkyl, —$OC_2$-$C_6$ alkenyl, —$OC_2$-$C_6$ alkynyl, —$OC_3$-$C_8$ cycloalkyl optionally having 1-3 double bonds, —C(=O)$C_1$-$C_6$alkyl, —C(=O)$C_3$-$C_8$ cycloalkyl, —$CO_2C_1$-$C_6$alkyl, —C(=O)S$C_1$-$C_6$alkyl, —$NR^3$C(=O)O$C_1$-$C_6$ alkyl, and —S(O)$_x$$C_1$-$C_6$ alkyl, $R^a$ is optionally substituted with 1-15 halogens and is optionally substituted with 1-3 substituent groups independently selected from (a) —OH, (b) —CN, (c) —$NR^3R^4$, (d) —$C_3$-$C_8$ cycloalkyl optionally having 1-3 double bonds and optionally substituted with 1-15 halogens, (e) —$OC_1$-$C_4$alkyl optionally substituted with 1-9 halogens and optionally substituted with 1-2 substituent groups independently selected from —$OC_1$-$C_2$ alkyl and phenyl, (f) —$OC_3$-$C_8$ cycloalkyl optionally having 1-3 double bonds and optionally substituted with 1-15 halogens, (g) —$CO_2$H, (h) —C(=O)$CH_3$, (i) —$CO_2C_1$-$C_4$alkyl which is optionally substituted with 1-9 halogens, and (j) phenyl which is optionally substituted with 1-3 groups independently selected from halogen, —$CH_3$, —$CF_3$, —$OCH_3$, and —$OCF_3$;

p is an integer from 0-4;
q is 0 or 1;
x is 0, 1, or 2;
y is 1 or 2;

$R^3$ and $R^4$ are each independently selected from H, —$C_1$-$C_5$ alkyl, —C(=O)$C_1$-$C_5$ alkyl and —S(O)$_y$$C_1$-$C_5$ alkyl, wherein —$C_1$-$C_5$ alkyl in all instances is optionally substituted with 1-11 halogens;

$R^7$ and $R^8$ are each independently selected from the group consisting of H, —$C_1$-$C_6$ alkyl, —$C_2$-$C_6$ alkenyl, —$C_2$-$C_6$ alkynyl, —C(=O)$C_1$-$C_6$alkyl, —$CO_2$H, —$CO_2C_1$-$C_6$alkyl, —$C_3$-$C_8$ cycloalkyl which optionally comprises 1-2 double bonds, —C(=O)$C_3$-$C_8$ cycloalkyl which optionally comprises 1-2 double bonds, —C(=O)phenyl, —C(=O)$NR^3R^4$, —S(O)$_2$$C_1$-$C_6$ alkyl, and —S(O)$_2$$NR^3R^4$, wherein —$C_1$-$C_6$ alkyl in all instances is optionally substituted with 1-11 halogens and is optionally substituted with 1-2 substituents independently selected from —$CO_2$H, —$CO_2C_1$-$C_6$alkyl which is optionally substituted with 1-11 halogens, —$NR^3R^4$, —OH, —C(=O)H—, a 5-7 membered heterocycle comprising 1-3 heteroatoms independently selected from N, O and S, —$C_3$-$C_8$ cycloalkyl, and phenyl, wherein said —$C_3$-$C_8$ cycloalkyl and phenyl groups are optionally substituted with (a) 1-5 substituents independently selected from (i) halogen, (ii) —$C_1$-$C_3$ alkyl optionally substituted with 1-5 halogens, and (iii) —$OC_1$-$C_3$ alkyl optionally substituted with 1-5 halogens, and (b) optionally 1-2 groups independently selected from —$CO_2$H, —$CO_2C_1$-$C_4$alkyl, —$CH_2CO_2$H, —$CH_2CO_2C_1$-$C_4$alkyl, —$CH_2CH_2CO_2$H, —$CH_2CH_2CO_2C_1$-$C_4$alkyl, —$NR^3R^4$, —CN, —$NO_2$, —C(=O)$NR^3R^4$, —$CH_2$C(=O)$NR^3R^4$, —S(O)$_2$$C_1$-$C_3$ alkyl, and —$C_1$-$C_5$ alkyl optionally substituted with 1-2 groups independently selected from —$NR^3R^4$, —OH, —C(=O)H—, and a 5-7 membered heterocycle comprising 1-3 heteroatoms independently selected from N, O and S, and optionally 1-5 halogens; wherein said 5-7 membered heterocycle in all uses as a substituent on —$C_1$-$C_6$ alkyl is optionally substituted with 1-5 substituents independently selected from halogen, —$C_1$-$C_3$ alkyl and —$OC_1$-$C_3$ alkyl, said —$C_1$-$C_3$ alkyl and —$OC_1$-$C_3$ alkyl being optionally substituted with 1-7 halogens;

wherein when $R^7$ or $R^8$ is —$C_3$-$C_8$ cycloalkyl which optionally comprises 1-2 double bonds, then said —$C_3$-$C_8$ cycloalkyl which optionally comprises 1-2 double bonds is optionally substituted with (a) 1-5 substituents independently selected from halogen, —$C_1$-$C_3$ alkyl optionally substituted with 1-5 halogen, and —$OC_1$-$C_3$ alkyl optionally substituted with 1-5 halogens, and (b) optionally also 1 group selected from —$CO_2$H, —$CO_2C_1$-$C_4$alkyl, —$CH_2CO_2$H, —$CH_2CO_2C_1$-$C_4$alkyl, —$CH_2CH_2CO_2$H, —$CH_2CH_2CO_2C_1$-$C_4$alkyl, —C(=O)$NR^3R^4$, —$CH_2$C(=O)$NR^3R^4$, —$CH_2CH_2$C(=O)$NR^3R^4$, —CN, —$NO_2$, and —S(O)$_2$$C_1$-$C_3$ alkyl;

and when $R^7$ or $R^8$ is —C(=O)phenyl or —C(=O)$C_3$-$C_8$ cycloalkyl which optionally comprises 1-2 double bonds, said phenyl or cycloalkyl which optionally comprises 1-2 double bonds is optionally substituted with (a) 1-5 substituents independently selected from halogen, —$C_1$-$C_3$ alkyl optionally substituted with 1-5 halogens, and —$OC_1$-$C_3$ alkyl optionally substituted with 1-5 halogens, and (b) optionally 1 group selected from —$CO_2$H, —$CO_2C_1$-$C_4$alkyl, —$CH_2CO_2$H, —$CH_2CO_2C_1$-$C_4$alkyl, —$CH_2CH_2CO_2$H, —$CH_2CH_2CO_2C_1$-$C_4$alkyl, —C(=O)$NR^3R^4$, —$CH_2$C(=O)$NR^3R^4$, —$CH_2CH_2$C(=O)$NR^3R^4$, —CN, —$NO_2$, and —S(O)$_2$$C_1$-$C_3$ alkyl;

wherein alternatively $R^7$ and $R^8$ are joined to form a monocyclic 5-7-membered heterocycle optionally having 1-2 heteroatoms independently selected from N, O and $S(O)_x$ in addition to the N to which $R^7$ and $R^8$ are connected or a bicyclic or tricyclic heterocycle having 5-16 atoms and optionally having 1-5 heteroatoms independently selected from N, O and $S(O)_x$ in addition to the N to which $R^7$ and $R^8$ are connected, said heterocycle being saturated, partly unsaturated or aromatic, said heterocycle being optionally substituted with (a) 1-5 substituent groups independently selected from halogen, —$C_1$-$C_3$ alkyl optionally substituted with 1-5 halogens, and —$OC_1$-$C_3$ alkyl optionally substituted with 1-5 halogens and optionally one —OH group, and (b) optionally 1 substituent selected from —$CO_2H$, —$CO_2C_1$-$C_4$alkyl, —$CH_2CO_2H$, —$CH_2CO_2C_1$-$C_4$alkyl, —$CH_2CH_2CO_2H$, and —$CH_2CH_2CO_2C_1$-$C_4$alkyl; and $R^{10}$ and $R^{11}$ are each independently selected from the group consisting of H and —$C_1$-$C_5$ alkyl, wherein —$C_1$-$C_5$ alkyl is optionally substituted with 1-11 halogens.

2. The compound of claim 1, which is selected from the group consisting of compounds having Formula Ia and Ib, or a pharmaceutically acceptable salt thereof:

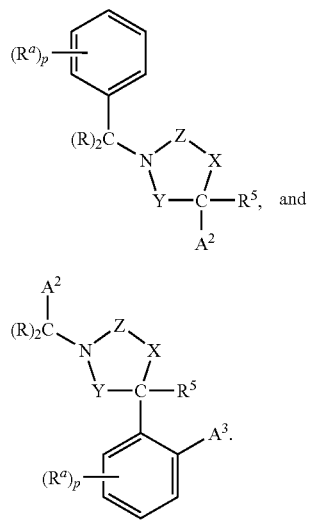

3. The compound of claim 1, or a pharmaceutically acceptable salt thereof, wherein:

Y is —$(CRR^1)$—;

R, $R^5$, and $R^{10}$ are H;

$R^1$ is selected from the group consisting of H and —$C_1$-$C_2$ alkyl;

B is $A^1$, and $R^2$ is $A^2$;

$A^2$ is phenyl which is optionally substituted with 1-3 substituent groups independently selected from $R^a$;

p is an integer from 0-2; and

Each $R^a$ is independently selected from the group consisting of —$C_1$-$C_3$ alkyl optionally substituted with 1-3 halogens, —$OC_1$-$C_3$alkyl optionally substituted with 1-3 halogens, —$C_2$-$C_4$ alkenyl, halogen, —CN, —$NO_2$, $C_3$-$C_6$ cycloalkyl, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which $R^a$ is attached is a carbon atom, wherein said heterocyclic ring and $C_3$-$C_6$ cycloalkyl are optionally substituted with 1-3 substituent groups independently selected from halogen, —$CH_3$, —$OCH_3$, —$CF_3$, and —$OCF_3$.

4. The compound of claim 3, or a pharmaceutically acceptable salt thereof, wherein One of $R^7$ and $R^8$ is optionally H, and $R^7$ and $R^8$ are each independently selected from the group consisting of —$C_1$-$C_6$ alkyl, —$C(=O)C_1$-$C_6$alkyl, —$CO_2H$, —$CO_2C_1$-$C_6$alkyl, —$C_3$-$C_6$ cycloalkyl, —$C(=O)C_3$-$C_6$ cycloalkyl, —$C(=O)$phenyl, —$C(=O)NR^3R^4$, —$S(O)_2C_1$-$C_3$ alkyl, and —$S(O)_2NR^3R^4$, wherein —$C_1$-$C_6$ alkyl in all instances is optionally substituted with 1-3 F atoms and is optionally substituted with one substituent selected from —$CO_2H$, —$CO_2C_1$-$C_6$alkyl which is optionally substituted with 1-3 F atoms, —$NR^3R^4$, —OH, —$C(=O)H$—, a 5-6 membered heterocycle comprising 1-2 heteroatoms independently selected from N, O and S, —$C_3$-$C_6$ cycloalkyl, and phenyl, wherein said —$C_3$-$C_6$ cycloalkyl and phenyl groups are optionally substituted with (a) 1-2 substituents independently selected from (i) fluorine, (ii) —$C_1$-$C_3$ alkyl optionally substituted with 1-3 F atoms, and (iii) —$OC_1$-$C_3$ alkyl optionally substituted with 1-3 F atoms, and (b) optionally one group selected from —$CO_2H$, —$CO_2C_1$-$C_4$alkyl, —$CH_2CO_2H$, —$CH_2CO_2C_1$-$C_4$alkyl, —$CH_2CH_2CO_2H$, —$CH_2CH_2CO_2C_1$-$C_4$alkyl, —$NR^3R^4$, —CN, —$NO_2$, —$C(=O)NR^3R^4$, —$CH_2C(=O)NR^3R^4$, —$S(O)_2C_1$-$C_3$ alkyl, and —$C_1$-$C_5$ alkyl optionally substituted with 1-2 groups independently selected from —$NR^3R^4$, —OH, —$C(=O)H$—, and a 5-6 membered heterocycle comprising 1-2 heteroatoms independently selected from N, O and S, and optionally 1-5 F atoms; wherein said 5-6 membered heterocycle in all uses as a substituent on —$C_1$-$C_6$ alkyl is optionally substituted with 1-3 substituents independently selected from F, —$CH_3$, —$CF_3$, —$OCH_3$, and —$OCF_3$, wherein when $R^7$ or $R^8$ is —$C_3$-$C_6$ cycloalkyl, said cycloalkyl is optionally substituted with (a) 1-5 substituents independently selected from F, —$CH_3$, and —$CF_3$; and (b) optionally 1 group selected from —$CO_2H$, —$CO_2C_1$-$C_4$alkyl, —$CH_2CO_2H$, —$CH_2CO_2C_1$-$C_4$alkyl, —$CH_2CH_2CO_2H$, —$CH_2CH_2CO_2C_1$-$C_4$alkyl, —$C(=O)NR^3R^4$, —$CH_2C(=O)NR^3R^4$, —$CH_2CH_2C(=O)NR^3R^4$, —CN, —$NO_2$, and —$S(O)_2C_1$-$C_3$ alkyl;

and when $R^7$ or $R^8$ is —$C(=O)$phenyl or —$C(=O)C_3$-$C_6$ cycloalkyl, said phenyl or cycloalkyl is optionally substituted with (a) 1-2 substituents independently selected from F, —$CH_3$, —$CF_3$, —$OCH_3$, and —$OCF_3$; and (b) optionally 1 group selected from —$CO_2H$, —$CO_2C_1$-$C_4$alkyl, —$CH_2CO_2H$, —$CH_2CO_2C_1$-$C_4$alkyl, —$CH_2CH_2CO_2H$, —$CH_2CH_2CO_2C_1$-$C_4$alkyl, —$C(=O)NR^3R^4$, —$CH_2C(=O)NR^3R^4$, —$CH_2CH_2C(=O)NR^3R^4$, —CN, —$NO_2$, and —$S(O)_2C_1$-$C_3$ alkyl;

wherein alternatively $R^7$ and $R^8$ are joined to form a monocyclic 5-7-membered heterocycle optionally having 1-2 heteroatoms independently selected from N, O and $S(O)_x$ in addition to the N to which $R^7$ and $R^8$ are connected or a bicyclic heterocycle having 6-12 atoms and optionally having 1-2 heteroatoms independently selected from N, O and $S(O)_x$ in addition to the N to which $R^7$ and $R^8$ are connected, said heterocycle being optionally substituted with (a) 1-3 substituent groups independently selected from F, —$CH_3$, —$CF_3$, —$OCH_3$, and —$OCF_3$; and (b) optionally 1 substituent selected from —$CO_2H$, —$CO_2C_1$-$C_4$alkyl, —CH₂CO₂H, —CH₂CO₂C₁-C₄alkyl, —CH₂CH₂CO₂H, and —CH₂CH₂CO₂C₁-C₄alkyl.

5. The compound of claim 4, or a pharmaceutically acceptable salt thereof, wherein R³ and R⁴ are each independently selected from H and C₁-C₃alkyl;

A² is phenyl which is optionally substituted with 1-3 groups independently selected from halogen, C₁-C₃alkyl optionally substituted with 1-3 halogens, and —OC₁-C₃alkyl optionally substituted with 1-3 halogens;

p is an integer from 0-2; and

Each Rᵃ is selected from the group consisting of halogen, C₁-C₃alkyl optionally substituted with 1-3 halogens, —OC₁-C₃alkyl optionally substituted with 1-3 halogens, C₂-C₄alkenyl, and C₃-C₆cycloalkyl.

6. A pharmaceutical composition comprising the compound of claim 1, or a pharmaceutically acceptable salt thereof, and a pharmaceutically acceptable carrier.

7. The compound of claim 1, which is selected from the group consisting of the following compounds, or a pharmaceutically acceptable salt thereof:

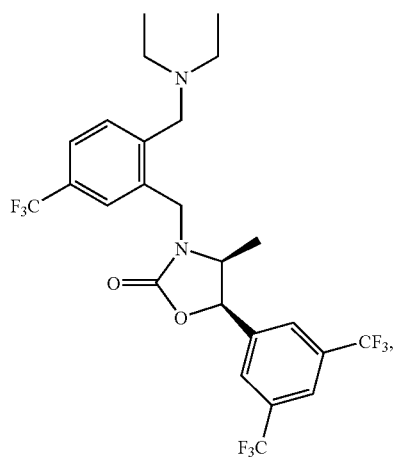

Ex. 1

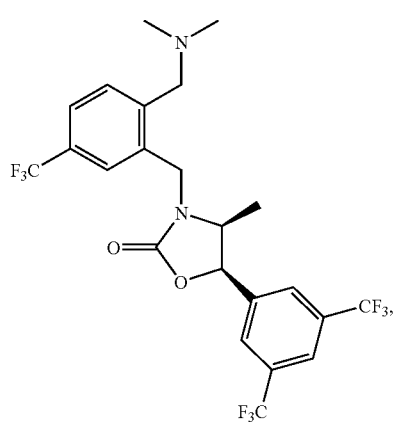

Ex. 2

-continued

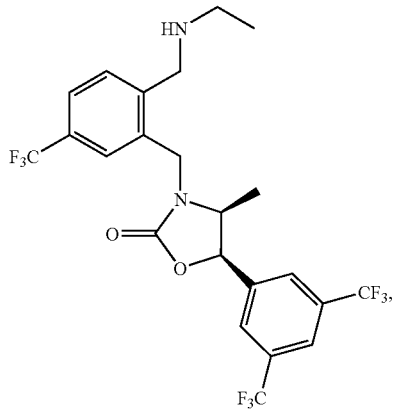

Ex. 3

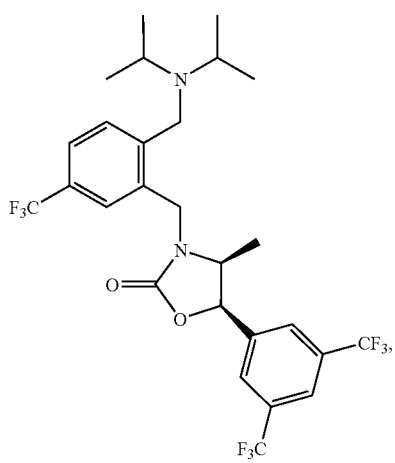

Ex. 4

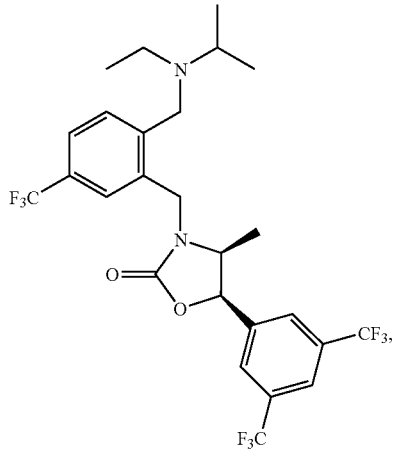

Ex. 5

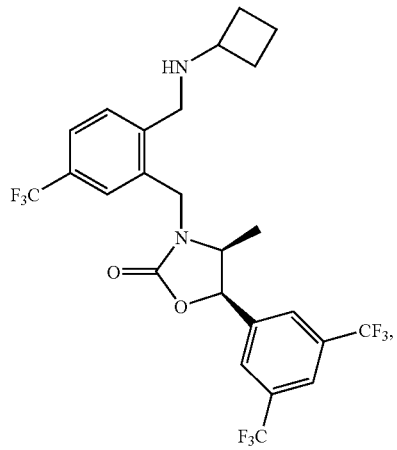
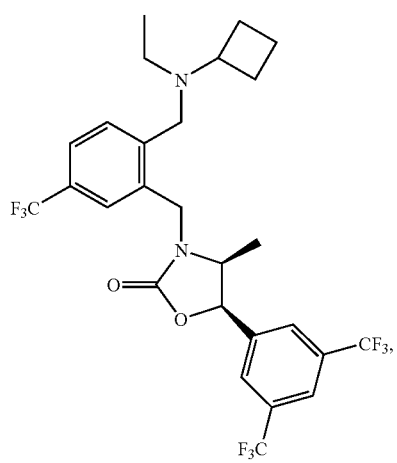
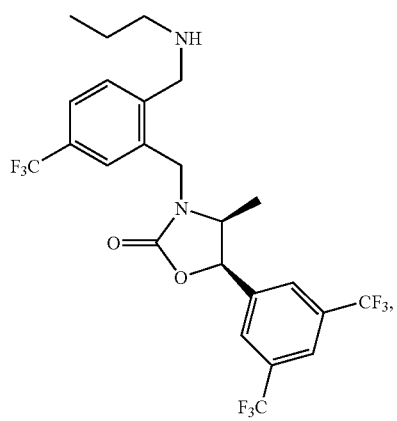
Ex. 6
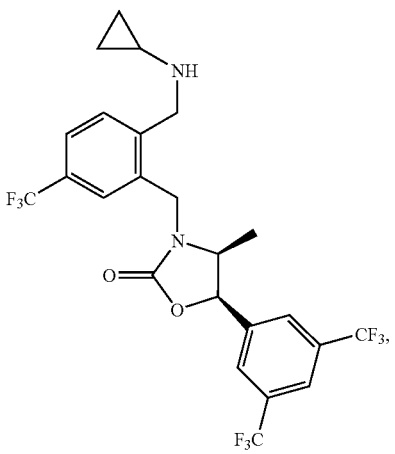
Ex. 7
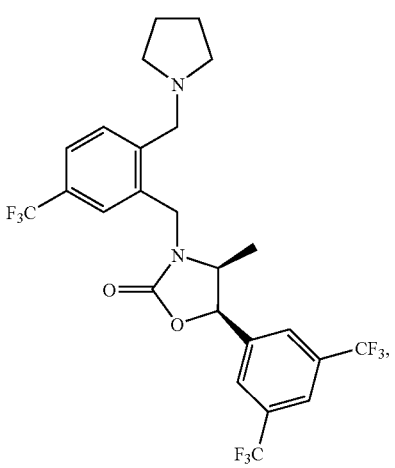
Ex. 8
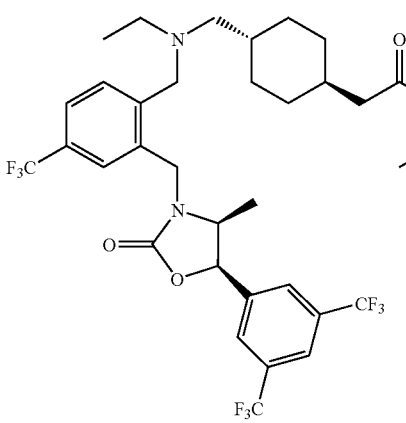
Ex. 9
Ex. 10
Ex. 11

Ex. 12
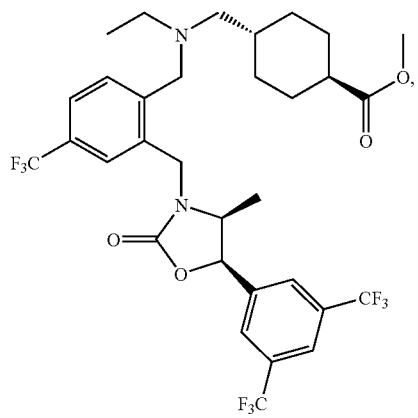
Ex. 15
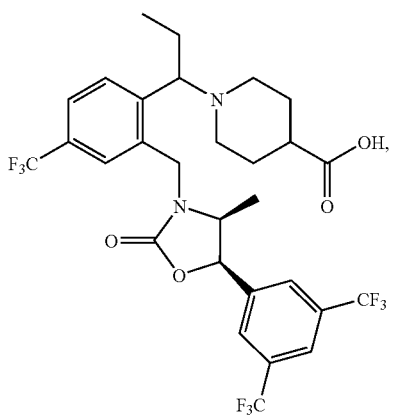
Ex. 13
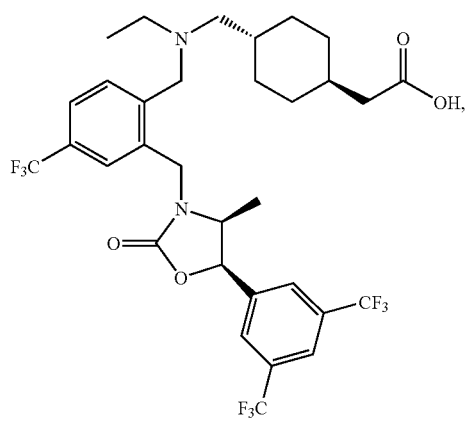
Ex. 16
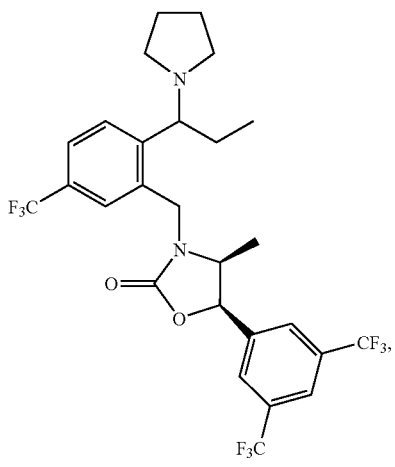
Ex. 14
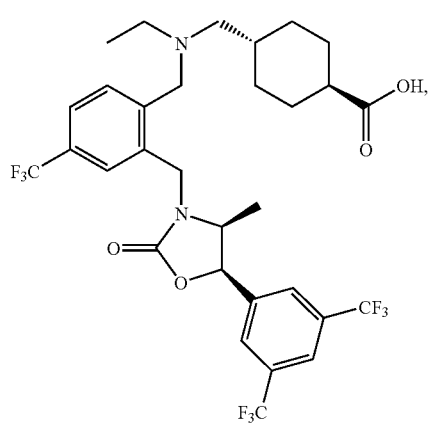
Ex. 17
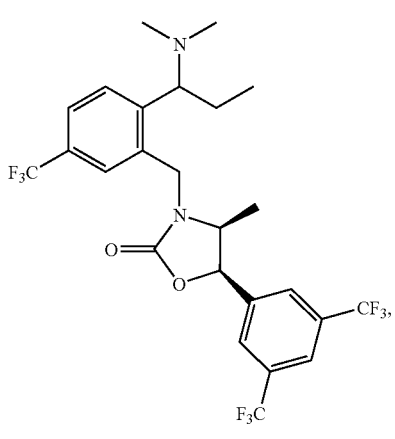

-continued
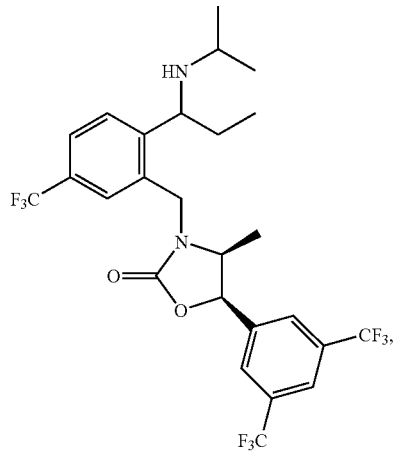
Ex. 18
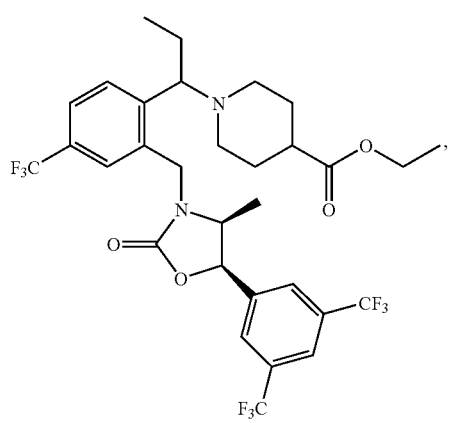
Ex. 19
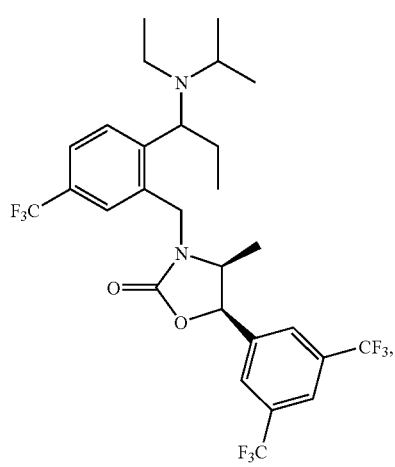
Ex. 20
-continued
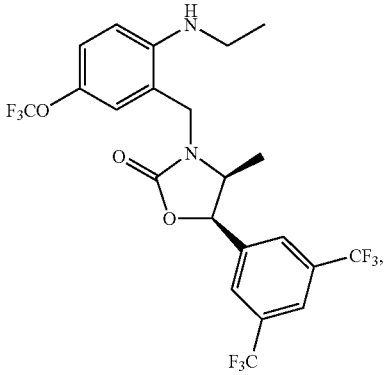
Ex. 21
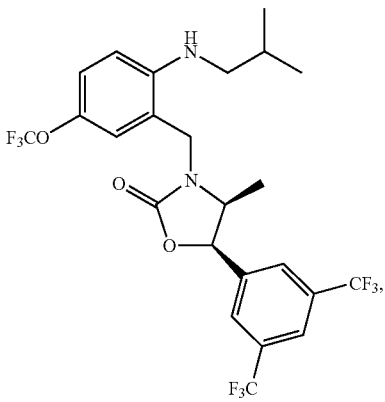
Ex. 22
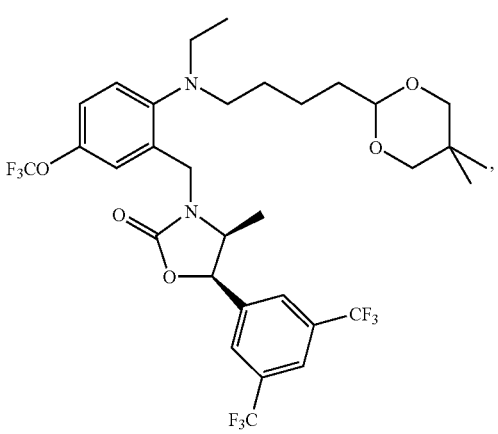
Ex. 31

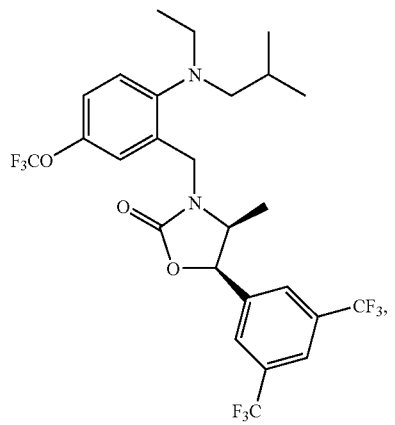
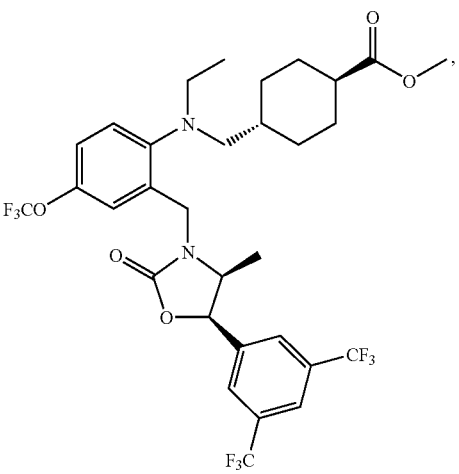

Ex. 38
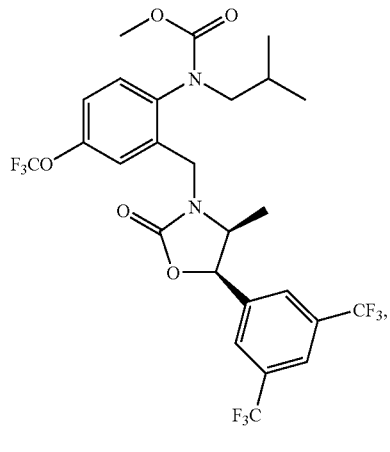
Ex. 41
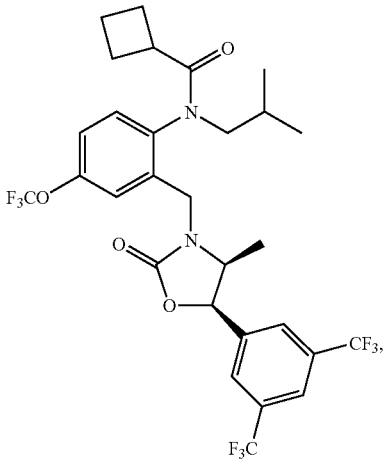
Ex. 39
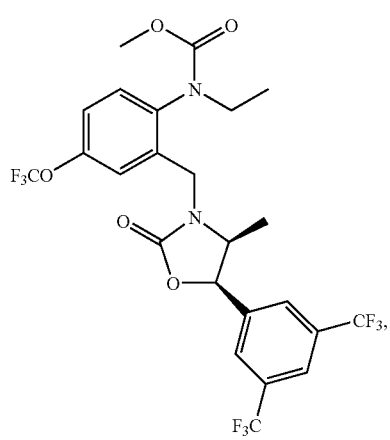
Ex. 42
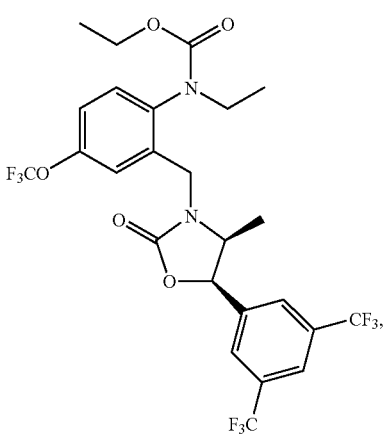
Ex. 40
Ex. 43
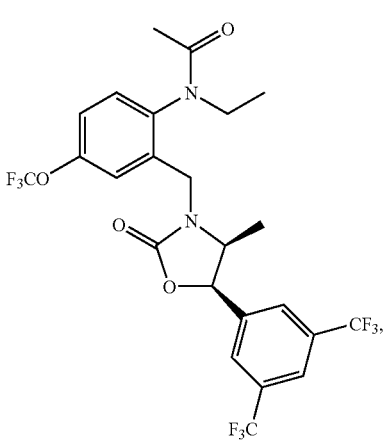

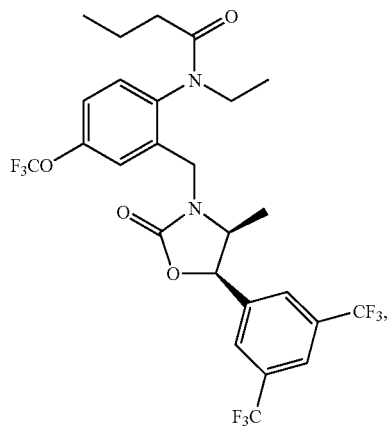
Ex. 44
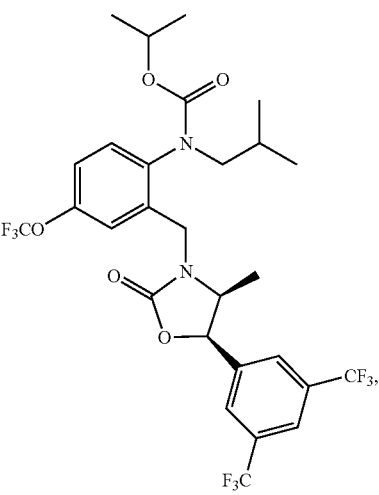
Ex. 47
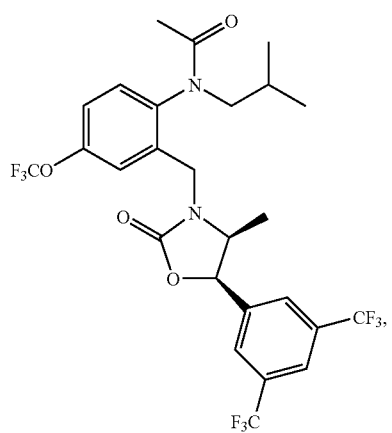
Ex. 45
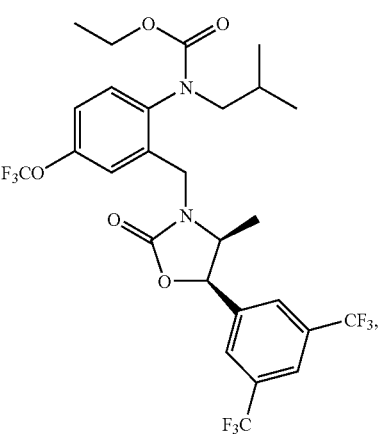
Ex. 48
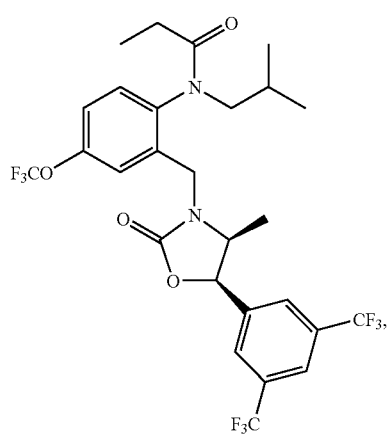
Ex. 46
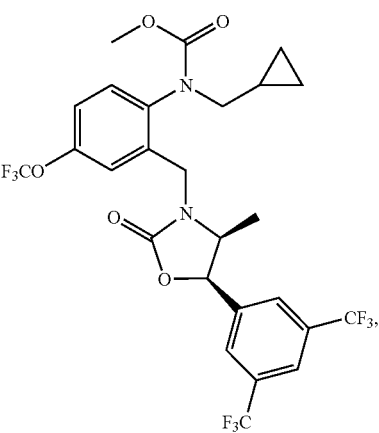
Ex. 49

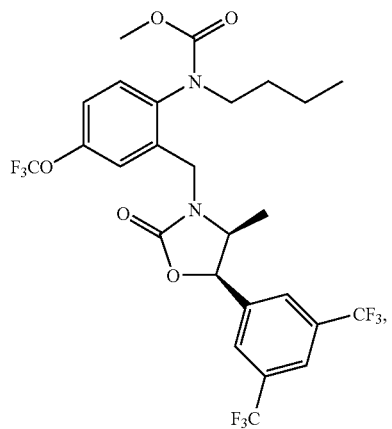
Ex. 50
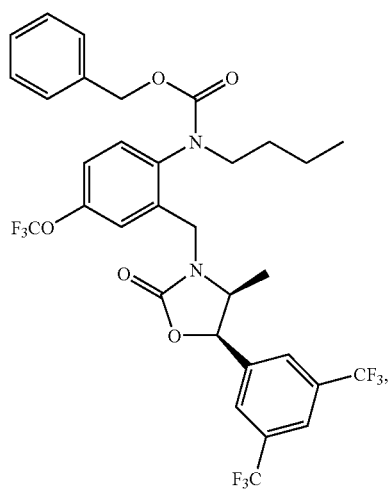
Ex. 51
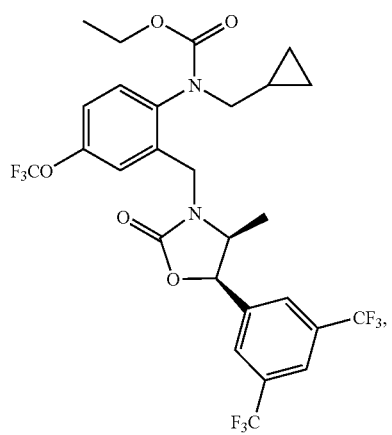
Ex. 52
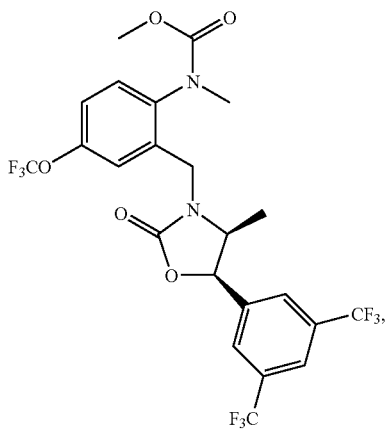
Ex. 53
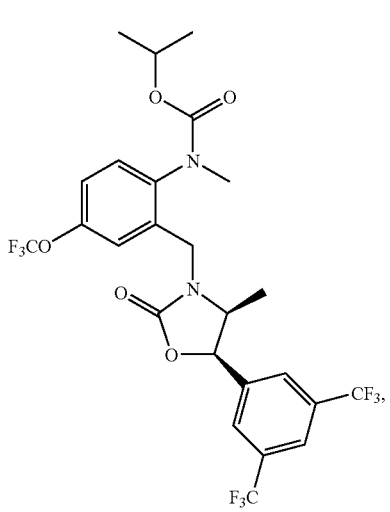
Ex. 54
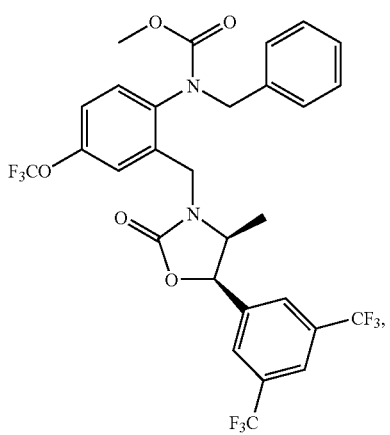
Ex. 55

Ex. 56 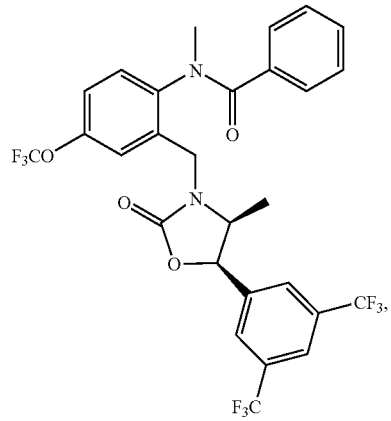
Ex. 59 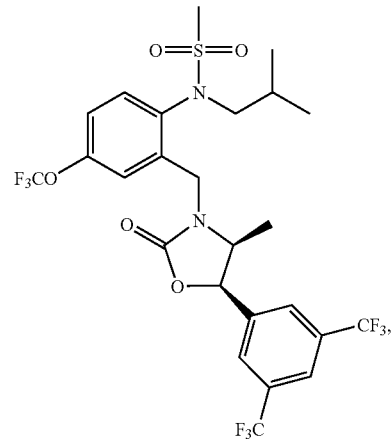
Ex. 57 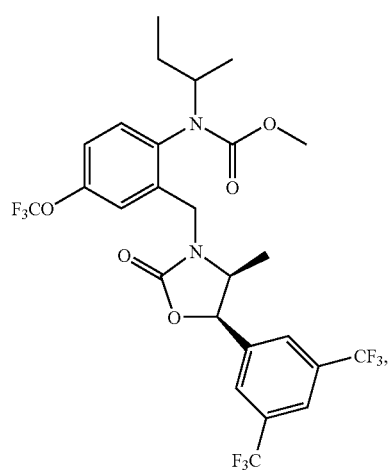
Ex. 60 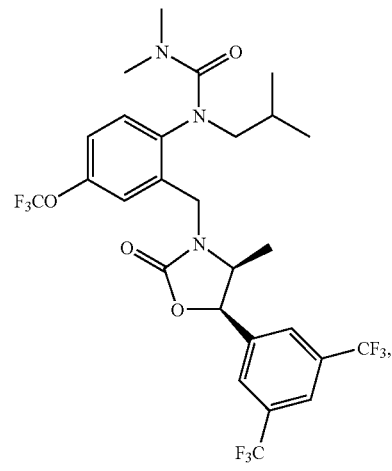
Ex. 58 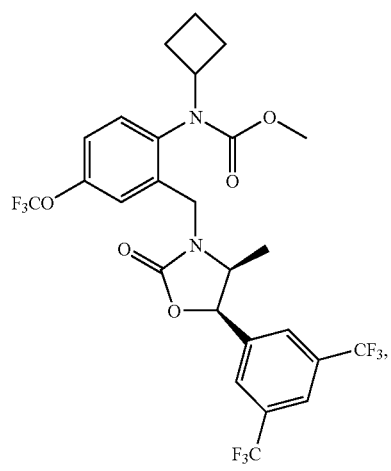
Ex. 61

Ex. 62
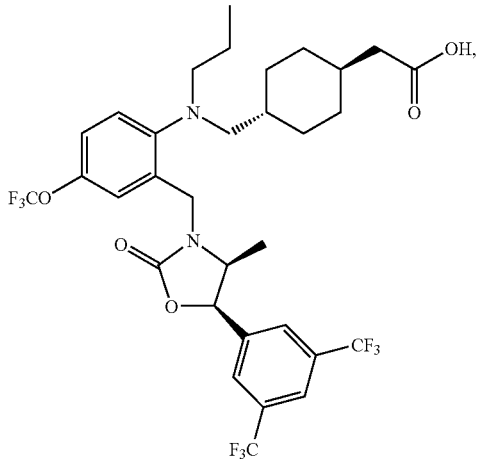
Ex. 63
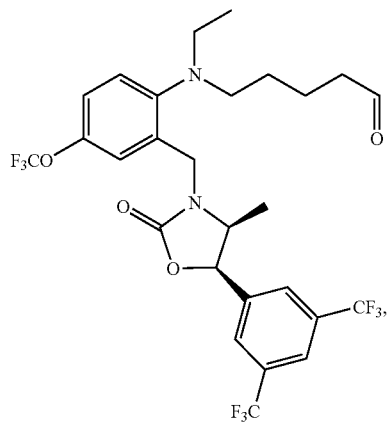
Ex. 64
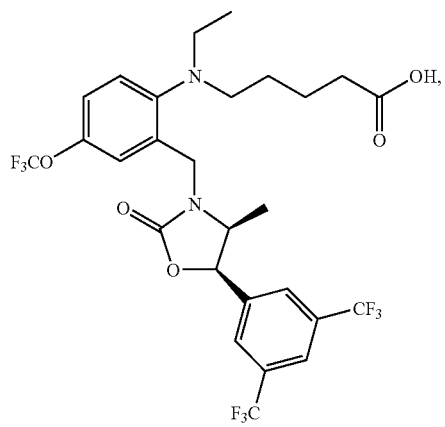
Ex. 65
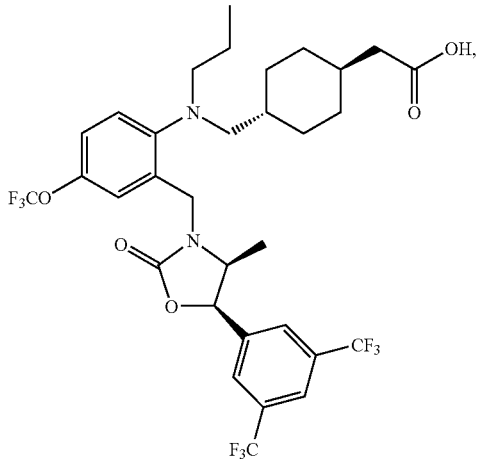
Ex. 66
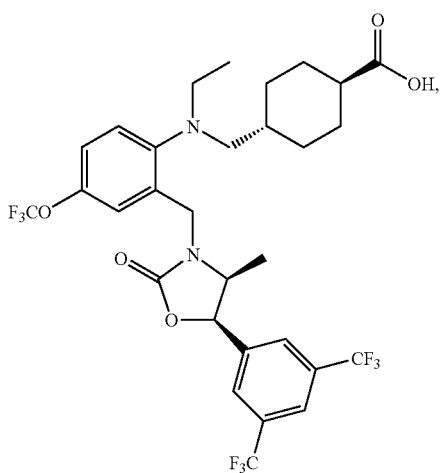
Ex. 67
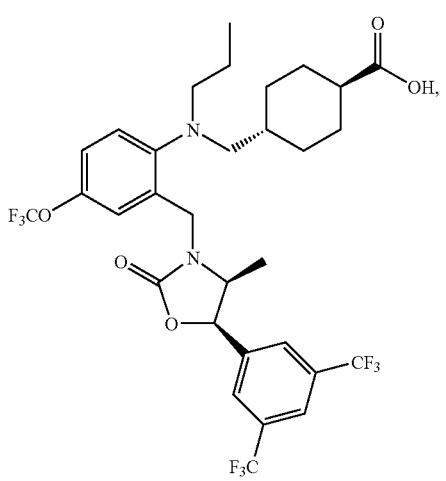

Ex. 68
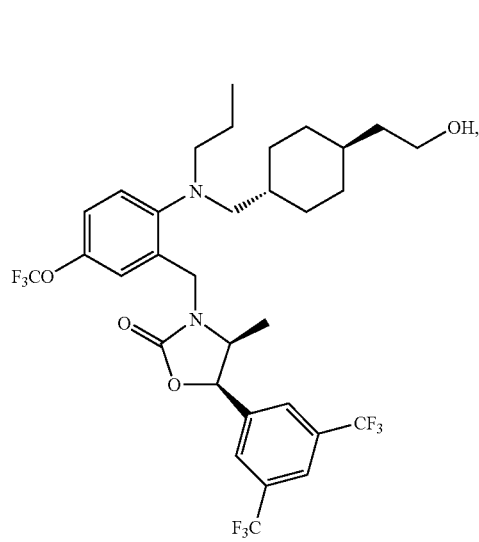
Ex. 69
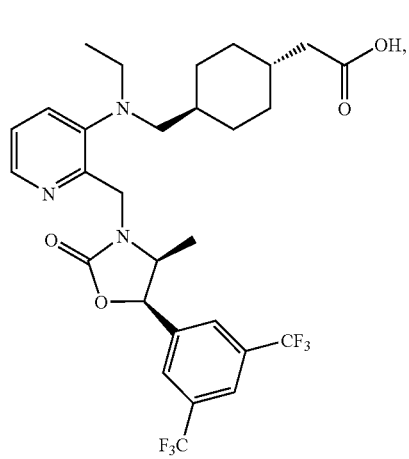
Ex. 70
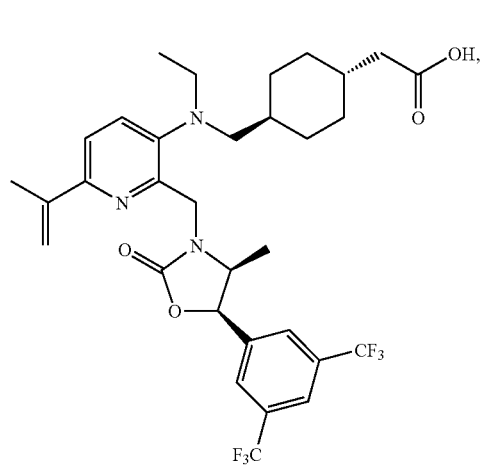
Ex. 71
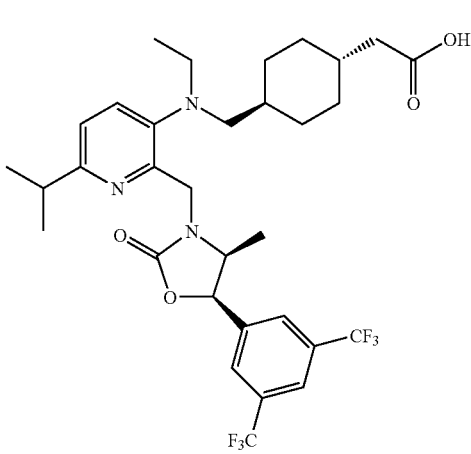
Ex. 72
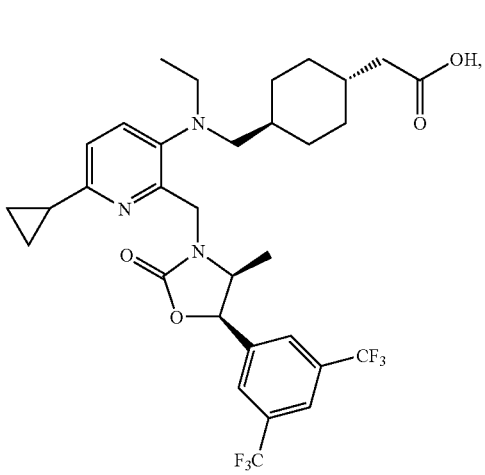
Ex. 73
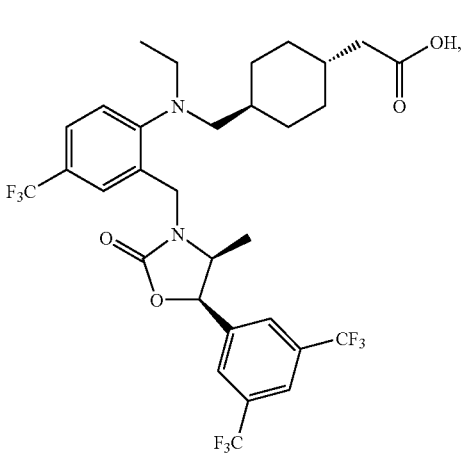

-continued
Ex. 74
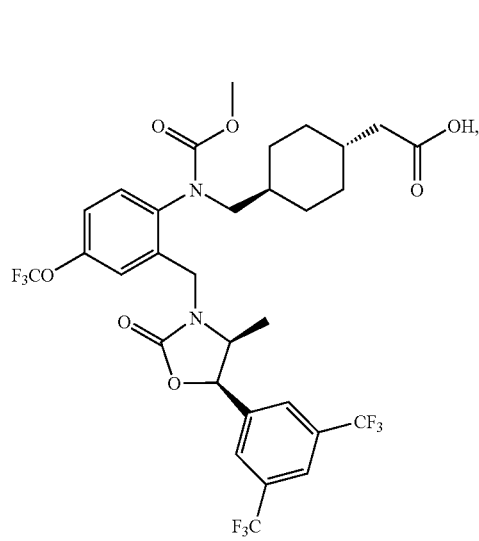
Ex. 85
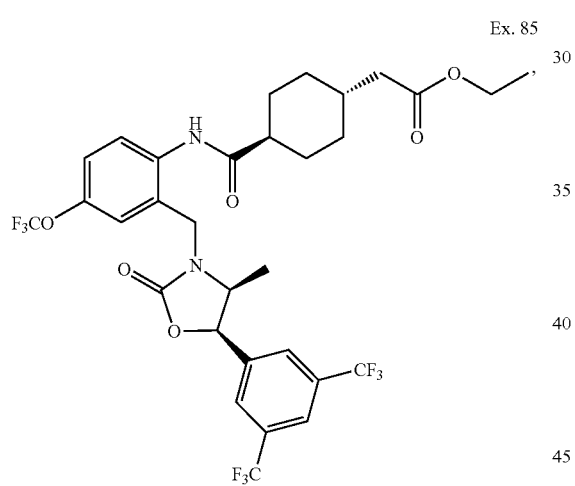
Ex. 86
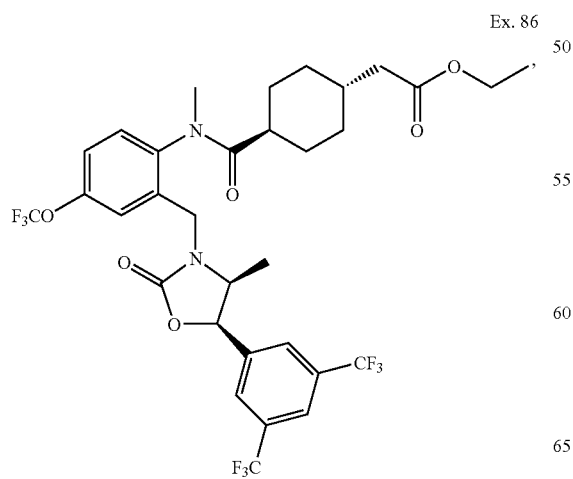
-continued
Ex. 87
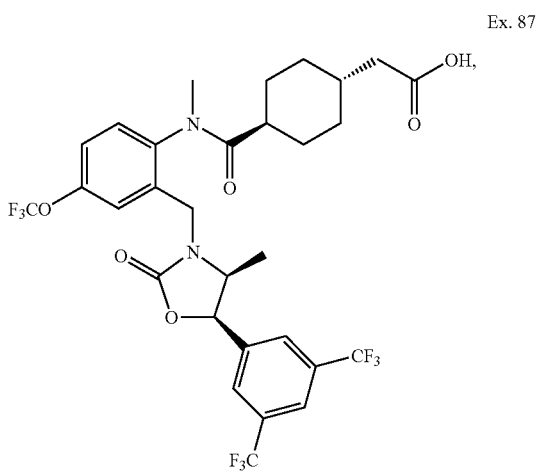
Ex. 88
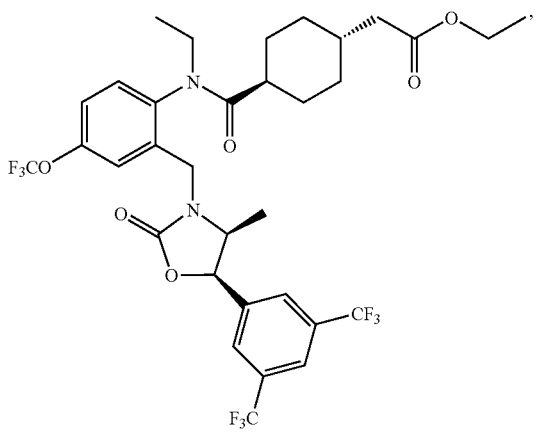
Ex. 89
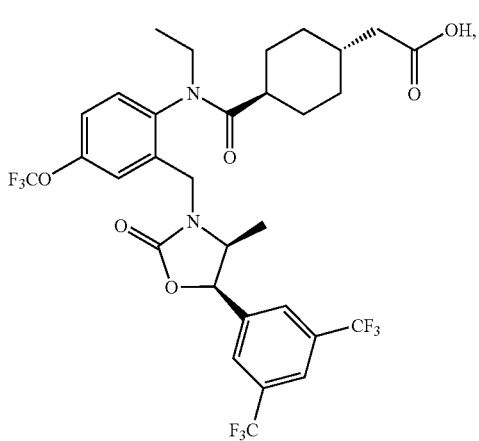

-continued

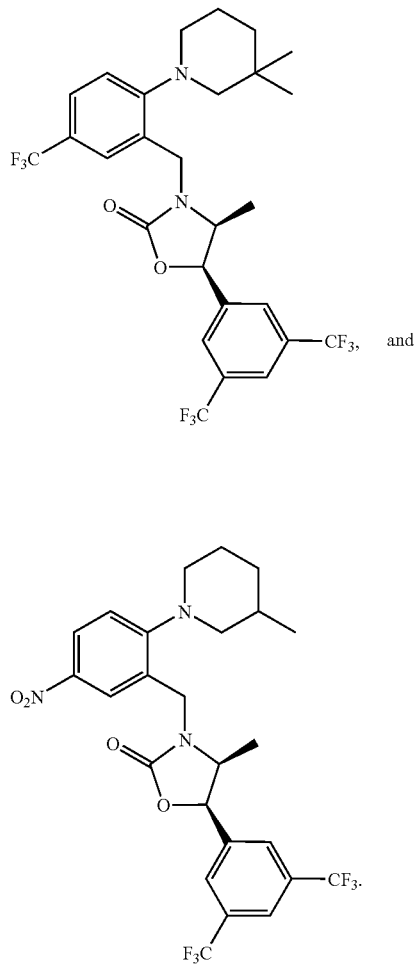

Ex. 90

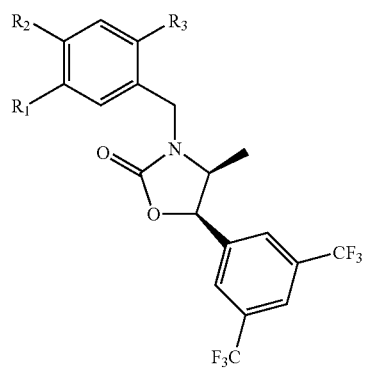

Ex. 96

8. The compound of claim 1, which is selected from the following compounds, or a pharmaceutically acceptable salt thereof:

(a)

wherein $R^1$, $R^2$, and $R^3$ for each compound are defined as follows:

| EXAMPLE | $R_1$ | $R_2$ | $R_3$ |
|---|---|---|---|
| 75 | $CF_3$ | H | (ethyl-N-cyclohexyl-CH2-COOH) |
| 76 | $CF_3$ | H | (propyl-N-cyclohexyl-CH2-COOH) |
| 77 | $CF_3$ | $CH_3$ | (propyl-N-cyclohexyl-CH2-COOH) |
| 78 | $OCF_3$ | H | (ethyl-N-CH2-cyclopentyl) |
| 79 | $OCF_3$ | H | (ethoxycarbonyl-N-cyclohexyl-CH2-COOH) |
| 80 | $OCF_3$ | H | (methoxycarbonyl-N-CH2-phenyl-3-COOH) |
| 81 | $OCF_3$ | H | (methoxycarbonyl-N-CH2-phenyl-4-COOH) |
| 82 | $OCF_3$ | H | (acetyl-N-cyclohexyl-CH2-COOH) |
| 83 | CF3 | H | (ethyl-N-cyclohexyl-COOCH3), and |

-continued
| EXAMPLE | R₁ | R₂ | R₃ |
|---|---|---|---|
| 84 | CF3 | H | 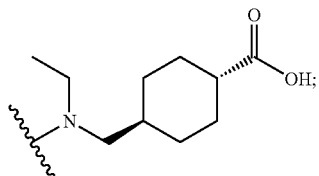 |
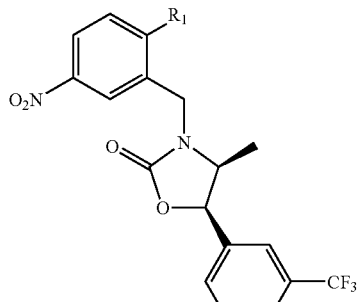  (c)
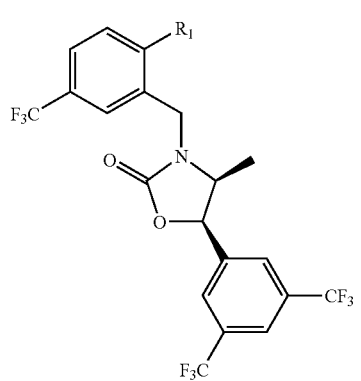  (b)
wherein R¹ is selected from the group consisting of:
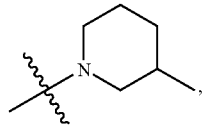  97
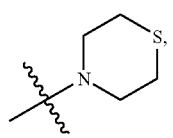  98
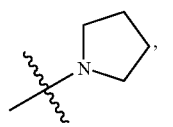  99
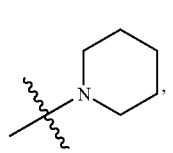  100
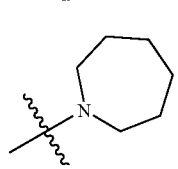  101
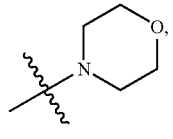  102
wherein R¹ is selected from the group consisting of:
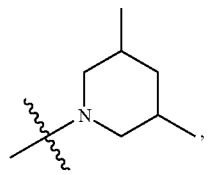  Ex 91
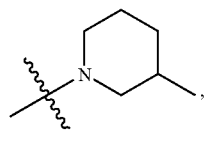  Ex 92
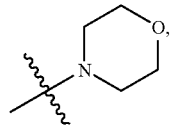  Ex 93
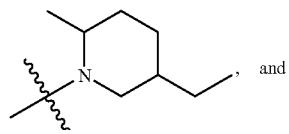  Ex 94, and
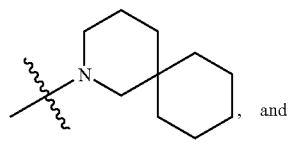  Ex 95, and
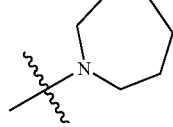  103

-continued

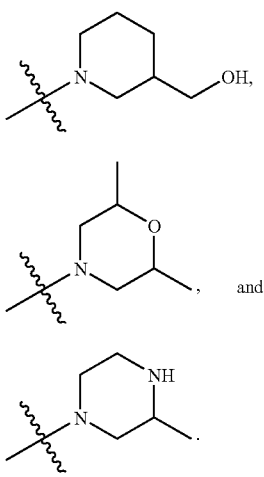

9. A method of treating atherosclerosis in a patient in need of treatment comprising the administration of a therapeutically effective amount of the compound of claim 1 to said patient, or a pharmaceutically acceptable salt thereof.

10. A method of raising HDL-C in a patient in need of treatment comprising the administration of a therapeutically effective amount of the compound of claim 1 to said patient, or a pharmaceutically acceptable salt thereof.

11. A method of lowering LDL-C in a patient in need of treatment comprising the administration of a therapeutically effective amount of the compound of claim 1 to said patient, or a pharmaceutically acceptable salt thereof.

12. A pharmaceutical composition comprising the compound of claim 1 or a pharmaceutically acceptable salt thereof, a pharmaceutically acceptable carrier, and one or more active ingredients selected from the group consisting of:
   (i) HMG-CoA reductase inhibitors;
   (ii) bile acid sequestrants;
   (iii) niacin and related compounds;
   (iv) PPARα agonists;
   (v) cholesterol absorption inhibitors;
   (vi) acyl CoA:cholesterol acyltransferase (ACAT) inhibitors;
   (vii) phenolic anti-oxidants;
   (viii) microsomal triglyceride transfer protein (MTP)/ApoB secretion inhibitors;
   (ix) anti-oxidant vitamins;
   (x) thyromimetics;
   (xi) LDL (low density lipoprotein) receptor inducers;
   (xii) platelet aggregation inhibitors;
   (xiii) vitamin B12 (also known as cyanocobalamin);
   (xiv) folic acid or a pharmaceutically acceptable salt or ester thereof;
   (xv) FXR and LXR ligands;
   (xvi) agents that enhance ABCA1 gene expression; and
   (xvii) ileal bile acid transporters.

* * * * *